US006949649B2

(12) United States Patent
Bonk et al.

(10) Patent No.: US 6,949,649 B2
(45) Date of Patent: Sep. 27, 2005

(54) THIOETHER SUBSTITUTED IMIDAZOQUINOLINES

(75) Inventors: Jason D. Bonk, Centerville, MN (US); Joseph F. Dellaria, Woodbury, MN (US); Bryon A. Merrill, River Falls, WI (US); Matthew R. Radmer, Robbinsdale, MN (US)

(73) Assignee: 3M Innovative Properties Co., St. Paul, MN (US)

( * ) Notice: Subject to any disclaimer, the term of this patent is extended or adjusted under 35 U.S.C. 154(b) by 0 days.

(21) Appl. No.: 10/696,477

(22) Filed: Oct. 29, 2003

(65) Prior Publication Data

US 2004/0097736 A1 May 20, 2004

Related U.S. Application Data

(63) Continuation of application No. 10/165,222, filed on Jun. 7, 2002, now Pat. No. 6,667,312, which is a continuation-in-part of application No. 10/013,059, filed on Dec. 6, 2001, now Pat. No. 6,664,264.
(60) Provisional application No. 60/254,218, filed on Dec. 8, 2000.

(51) Int. Cl.$^7$ ............... C07D 471/04; A61K 31/4745; A61P 37/02
(52) U.S. Cl. ............ 546/82; 546/84; 544/316; 514/293; 514/274
(58) Field of Search ................. 514/274, 293; 546/82, 84; 544/316

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gester | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,693,811 A | 12/1997 | Lindstrom | |
| 5,741,908 A | 4/1998 | Gerster et al. | |
| 5,756,747 A | 5/1998 | Gerster et al. | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,245,776 B1 | 6/2001 | Skwierczynski et al. | |
| 6,331,539 B1 | 12/2001 | Crooks et al. | |
| 6,376,669 B1 | 4/2002 | Rice et al. | |
| 6,451,810 B1 | 9/2002 | Coleman et al. | |
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,656,938 B2 | 12/2003 | Crooks et al. | |
| 6,660,735 B2 | 12/2003 | Crooks et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 2002/0055517 A1 | 5/2002 | Smith | |
| 2002/0058674 A1 | 5/2002 | Hedenstrom et al. | |

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46193 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |

OTHER PUBLICATIONS

Sof'ina et al. Experimental Evaluation of Antitumor Drugs in the USA and USSR and Clinical Correlations. NCI Monograph 55. NIH Publication No. 80–1933 (1980), pp. 76–78.*
Strandtmann et al. J. Med. Chem. (1967), 10(6):1063–1065.*
Wozniak, et al, "The Amination of 3–nitro–1, 5–naphthyridines by Liquid Ammonia/Potassium Permanganate$^{1,2}$. A New and Convenient Amination Method.", *Journal of the Royal Netherlands Chemical Society*, 102, pp 511–513, Dec. 12, 1983.
Brennan, et al, "Automated Bioassay of Interferons in Micro–test Plates", *Biotechniques*, Jun./Jul., 78, 1983.

(Continued)

Primary Examiner—Evelyn Mei Huang
(74) Attorney, Agent, or Firm—Dean A. Ersfeld

(57) ABSTRACT

Imidazoquinoline and tetrahydroimidazoquinoline compounds that contain thioether functionality at the 1-position are useful as immune response modifiers. The compounds and compositions of the invention can induce the biosynthesis of various cytokines and are useful in the treatment of a variety of conditions including viral diseases and neoplastic diseases.

1 Claim, No Drawings

OTHER PUBLICATIONS

Testerman, et al., "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline", *J. Org. Chem*, 15, pp 1278–1284 (1950).

Jain, et al, "Chemical and Pharmacological Investigations of Some ω–Substituted Alkylamino–3–aminopyridines", *J. Med. Chem.*, 11, pp 87–92 (1968).

Baranov, et al., *Chem. Abs.* 85, 94362, (1976).

Berényi, et al, "Ring Transformation of Condensed Dihydro–as–triazines", *J. Heterocyclic Chem.*, 18, pp. 1537–1540 (1981).

Chollet, et al, "Development of a Topically Active Imiquimod Formulation", *Pharmaceutical Development and Technology*, 4(1), pp 35–43 (1999).

Izumi, et al., "1H–Imidazo[4,5–c]quinoline Derivatives as Novel Potent TNF–αSuppressors: Synthesis and Structure–Activity Relationship of 1–, 2– and 4–Substituted 1H–imidazo[4,5–c]pyridines", *Bioorganic & Medicinal Chemistry*, pp 2541–2550 (2003).

Sidky etal., "Inhibition of Murine Tumor Growth by an Interferon–Inducing Imidazoquinolinamine", *Cancer Research*, 52, 3528–3533, Jul. 1, 1992.

R.L. Miller et al., "Imiquimod applied topically: a novel immune response modifier and new class of drug", *International Journal of Immunopharmacology*, 21, 1–14 (1999).

Karl R. Beutner, MD, et al., "Therapeutic response of basal cell carcinoma to the immune response modifier imiquimod 5% cream", *J.Am.Acad.Dermatol.*, vol. 41, No. 6, 1002–1007 (Dec. 1999).

Davis et al., "Self–Administered Topical Imiquimod Treatment of Vulvar Intraepithelial Neoplasia", *Journal of Reproductive Medicine*, vol. 45, No. 8, 619–623, (Aug. 2000).

Alexander Steinmann et al., "Topical Imiquimod Treatment of a Cutaneous Melanoma Metastasis", *J.Am.Acad.Dermtol.*, Letters, 555–556 (Sep. 2000).

* cited by examiner

THIOETHER SUBSTITUTED IMIDAZOQUINOLINES

CROSS REFERENCE TO RELATED APPLICATIONS

This application is a continuation of U.S. application Ser. No. 10/165,222, filed Jun. 7, 2002, now U.S. Pat. No. 6,667,312, which is a continuation-in-part of U.S. application Ser. No. 10/013,059, filed Dec. 6, 2001, now U.S. Pat. No. 6,664,264, which claims the benefit of U.S. Provisional Application No. 60/254,218, filed Dec. 8, 2000.

FIELD OF THE INVENTION

This invention relates to imidazoquinoline compounds that have thioether functionality at the 1-position, and to pharmaceutical compositions containing such compounds. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c] quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system.

Certain 1H-imidazo[4,5-c] naphthyridine-4-amines, 1H-imidazo [4,5-c] pyridin-4-amines, and 1H-imidazo[4,5-c] quinolin-4-amines having an ether containing substituent at the 1 position are known. These are described in U.S. Pat. Nos. 5,268,376; 5,389,640; 5,494,916; and WO 99/29693.

Despite these attempts to identify compounds that are useful as immune response modifiers, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazoquinoline-4-amine and tetrahydroimidazoquinoline-4-amine compounds that have a thioether containing substituent at the 1-position. The compounds are defined by Formulas (I) and (II), which are defined in more detail infra. These compounds share the general structural formula:

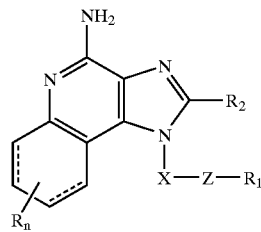

wherein X, Z, $R_1$, $R_2$, and R are as defined herein for each class of compounds having Formulas (I) and (II).

The compounds of formulas (I) and (II) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I) or (II) to the animal.

In addition, the invention provides methods of synthesizing the compounds of the invention.

DETAILED DESCRIPTION OF THE INVENTION

As mentioned earlier, we have found certain compounds that induce cytokine biosynthesis and modify the immune response in animals. Such compounds are represented by Formulas (I) and (II) as shown below.

Imidazoquinoline compounds of the invention, which have thioether functionality at the 1-position are represented by Formula (I):

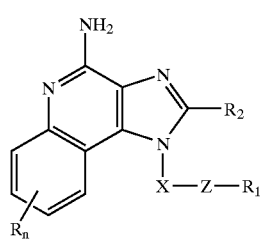

(I)

wherein: X is —$CHR_3$—, —$CHR_3$-alkyl-, or —$CHR_3$-alkenyl-;

Z is —S—, —SO—, or —$SO_2$—;

$R_1$ is selected from the group consisting of:
  -alkyl;
  -aryl;
  -heteroaryl;
  -heterocyclyl;
  -alkenyl;
  —$R_4$-aryl;
  —$R_4$-heteroaryl;
  —$R_4$-heterocyclyl;

—$R_2$ is selected from the group consisting of:
  -hydrogen;
  -alkyl;
  -alkenyl;

-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

each $R_3$ is independently H or $C_{1-10}$ alkyl;

$R_4$ is alkyl or alkenyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;
or a pharmaceutically acceptable salt thereof.

The invention also includes tetrahydroimidazoquinoline compounds that bear a thioether containing substituent at the 1-position. Such tetrahydroimidazoquinoline compounds are represented by Formula (II):

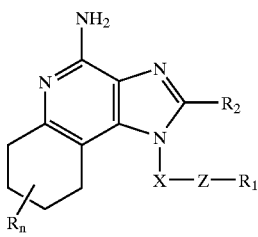

(II)

wherein: X is —CHR$_3$—, —CHR$_3$-alkyl-, or —CHR$_3$-alkenyl-;

Z is —S—, —SO—, or —SO$_2$—;

$R_1$ is selected from the group consisting of:
-alkyl;
-aryl;
-heteroaryl;
-heterocyclyl;
-alkenyl;
—$R_4$-aryl;
—$R_4$-heteroaryl; and
—$R_4$-heterocyclyl;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

each $R_3$ is independently H or $C_{1-10}$ alkyl;

$R_4$ is alkylene or alkenylene;

Y is —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;
or a pharmaceutically acceptable salt thereof.

Preparation of the Compounds

Compounds of the invention can be prepared according to Reaction Scheme I where R, $R_1$, $R_2$, X and n are as defined above.

In step (1) of Reaction Scheme I a 4-chloro-3-nitroquinoline of Formula X is reacted with an amine of formula HO—X—NH$_2$ to provide a 3-nitroquinolin-4-amine of Formula XI. The reaction can be carried out by adding the amine to a solution of a compound of Formula X in a suitable solvent such as chloroform or dichloromethane in the presence of triethylamine and optionally heating. Many quinolines of Formula X are known compounds (see for example, U.S. Pat. No. 4,689,338 and references cited therein). Many amines of formula HO—X—NH$_2$ are commercially available; others can be readily prepared using known synthetic routes.

In step (2) of Reaction Scheme I a 3-nitroquinolin-4-amine of Formula XI is chlorinated to provide a 3-nitroquinolin-4-amine of Formula XII. Conventional chlorinating agents can be used. Preferably the reaction is carried out by combining a compound of Formula XI with thionyl chloride in a suitable solvent such as dichloromethane. The reaction may be run at ambient temperature or it may be heated. Alternatively the reaction may be run neat.

In step (3) of Reaction Scheme I a 3-nitroquinolin-4-amine of Formula XII is reduced to provide a quinoline-3,4-diamine of Formula XIII. Preferably, the reduction is carried out using a conventional heterogeneous hydrogenation catalyst such as platinum on carbon. The reaction can conveniently be carried out on a Parr apparatus in a suitable solvent such as toluene.

In step (4) of Reaction Scheme I a quinoline-3,4-diamine of Formula XIII is reacted with a carboxylic acid or an equivalent thereof to provide a 1H-imidazo[4,5-c]quinoline of Formula XIV. Suitable equivalents to a carboxylic acid include orthoesters, and 1,1-dialkoxyalkyl alkanoates. The carboxylic acid or equivalent is selected such that it will provide the desired $R_2$ substituent in a compound of Formula XIV. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (4) can be carried out by (i) reacting the diamine of Formula XIII with an acyl halide of Formula $R_2C(O)Cl$ or $R_2C(O)Br$ and then (ii) cyclizing. In part (i) the acyl halide is added to a solution of the diamine in a suitable solvent such as pyridine. The reaction can be carried out at ambient temperature. In part (ii) the product of part (i) is heated in pyridine in the presence of pyridine hydrochloride.

In step (5) of Reaction Scheme I a 1H-imidazo[4,5-c]quinoline of Formula XIV is oxidized to provide a 1H-imidazo[4,5-c]quinoline-5N-oxide of Formula XV using a conventional oxidizing agent capable of forming N-oxides. Preferably a solution of a compound of Formula XIV in a suitable solvent such as chloroform or dichloromethane is treated with 3-chloroperoxybenzoic acid at ambient temperature.

In step (6) of Reaction Scheme I a 1H-imidazo[4,5-c]quinoline-5N-oxide of Formula XV is aminated to provide a 1H-imidazo[4,5-c]quinolin-4-amine of Formula XVI. Step (6) involves (i) reacting a compound of Formula XV with an acylating agent and then (ii) reacting the product with an aminating agent. Part (i) of step (6) involves reacting an N-oxide of Formula XV with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (6) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula XV in an inert solvent such as dichloromethane or chloroform, adding the aminating agent to the solution, and then slowly adding the acylating agent.

In step (7) of Reaction Scheme I a 1H-imidazo[4,5-c]quinolin-4-amine of Formula XVI is reacted with a compound of Formula $R_1$—SNa to provide a 1H-imidazo[4,5-c]quinolin-4-amine of Formula XVII which is a subgenus of Formula I. The reaction can be carried out by combining a compound of Formula XVI with a compound of formula $R_1SNa$ in a suitable solvent such as N,N-dimethylformamide or dimethyl sulfoxide. The reaction may be run at ambient temperature or it may be heated (60–80° C.). The product or a pharmaceutically acceptable salt thereof can be isolated using conventional methods.

In step (8) of Reaction Scheme I a 1H-imidazo[4,5-c]quinolin-4-amine of Formula XVII is oxidized using a conventional oxidizing agent to provide a 1H-imidazo[4,5-c]quinolin-4-amine of Formula XVIII which is a subgenus of Formula I. Preferably a solution of a compound of Formula XVII in a suitable solvent such as chloroform or dichloromethane is treated with 3-chloroperoxybenzoic acid at ambient temperature. The degree of oxidation is controlled by adjusting the amount of 3-chloroperoxybenzoic acid used in the reaction; i.e., using approximately one equivalent will provide the sulfoxide whereas using two equivalents will provide the sulfone. The product or a pharmaceutically acceptable salt thereof can be isolated using conventional methods.

Reaction Scheme I

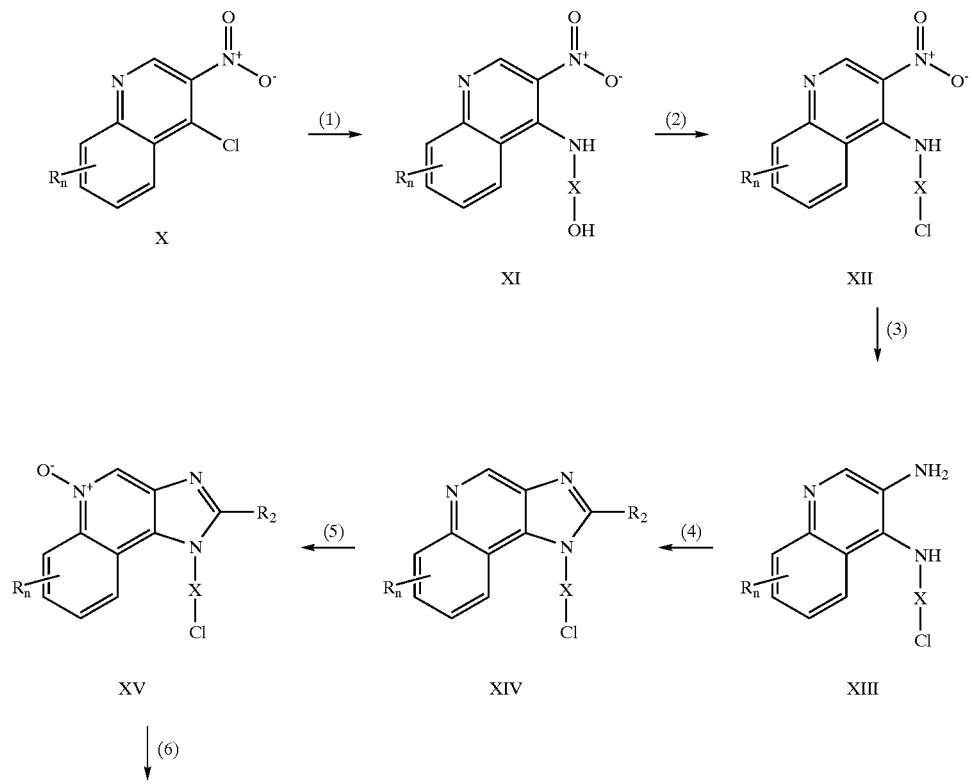

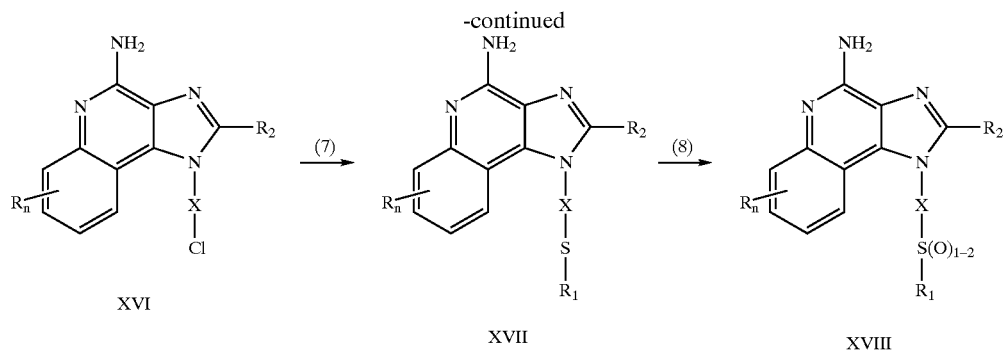

Compounds of the invention can be prepared according to Reaction Scheme II where R, $R_1$, $R_2$, X and n are as defined above.

In step (1) of Reaction Scheme II a 3-nitroquinolin-4-amine of Formula XIII is reacted with a compound of the Formula $R_1$—SNa using the method of step (7) of Reaction Scheme I to provide a 3-nitroquinolin-4-amine of Formula XIX.

In step (2) of Reaction Scheme II a 3-nitroquinolin-4-amine of Formula XIX is reduced using the method of step (3) of Reaction Scheme I to provide a quinoline-3,4-diamine of Formula XX.

In step (3) of Reaction Scheme II a quinoline-3,4-diamine of Formula XX is cyclized using the method of step (4) of Reaction Scheme I to provide a 1H-imidazo[4,5-c]quinoline of Formula XXI.

In step (4) of Reaction Scheme II a 1H-imidazo[4,5-c]quinoline of Formula XXI is oxidized to provide a 1H-imidazo[4,5-c]quinolin-5N-oxide of Formula XXII using a conventional oxidizing agent. Preferably a solution of a compound of Formula XXI in a suitable solvent such as chloroform or dichloromethane is treated with at least three equivalents of 3-chloroperoxybenzoic acid at ambient temperature.

In step (5) of Reaction Scheme II a 1H-imidazo[4,5-c]quinolin-5N-oxide of Formula XXII is aminated using the method of step (6) of Reaction Scheme I to provide a 1H-imidazo[4,5-c]quinolin-4-amine of Formula XVIII which is a subgenus of Formula I. The product or a pharmaceutically acceptable salt thereof can be isolated using conventional methods.

Reaction Scheme II

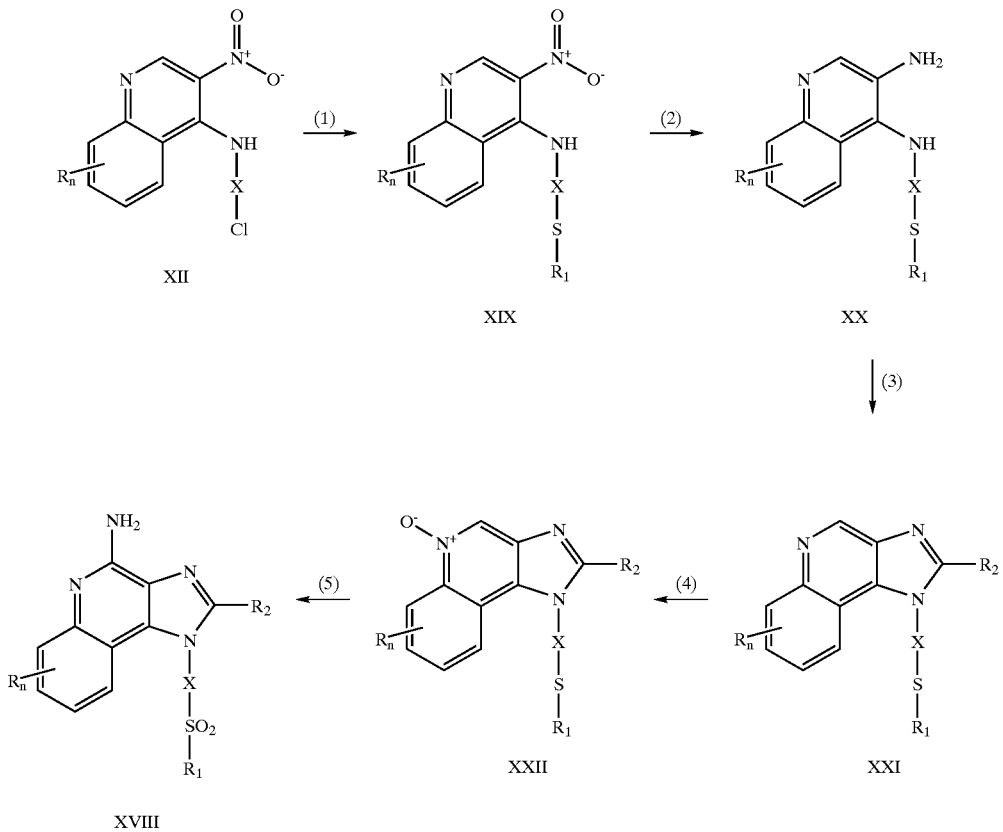

Compounds of the invention can be prepared according to Reaction Scheme III where R, $R_1$, $R_2$, X and n are as defined above.

In step (1) of Reaction Scheme III a 3-nitro-4-amino-quinolin-1-yl alcohol of Formula XI is protected with a tert-butyldimethylsilyl group using conventional methods. Preferably a compound of Formula XI is combined with tert-butyldimethylsilyl chloride in a suitable solvent such as chloroform in the presence of triethylamine and a catalytic amount of 4-dimethylaminopyridine.

In step (2) of Reaction Scheme III a protected 3-nitro-4-amino-quinolin-1-yl alcohol of Formula XXIII is reduced using the method of step (3) of Reaction Scheme I to provide a protected 3,4-diamino-quinolin-1-yl alcohol of Formula XXIV.

In step (3) of Reaction Scheme III a protected 3,4-diamino-quinolin-1-yl alcohol of Formula XXIV is cyclized using the method of step (4) of Reaction Scheme I to provide a 1H-imidazo[4,5-c]quinoline of Formula XXV.

In step (4) of Reaction Scheme III a 1H-imidazo[4,5-c]quinoline of Formula XXV is oxidized using the method of step (5) of Reaction Scheme I to provide a 1H-imidazo[4,5-c]quinolin-5N-oxide of Formula XXVI.

In step (5) of Reaction Scheme III a 1H-imidazo[4,5-c]quinolin-5N-oxide of Formula XXVI is aminated using the method of step (6) of Reaction Scheme I to provide a 1H-imidazo[4,5-c]quinolin-4-amine of Formula XXVII.

In step (6) of Reaction Scheme III the protecting group is removed from a 1H-imidazo[4,5-c]quinolin-4-amine of Formula XXVII to provide a 1H-imidazo[4,5-c]quinolin-4-amine of Formula XXVII. Preferably a solution of a compound of Formula XXVII in a suitable solvent such as tetrahydrofuran is treated with tetrabutylammonium fluoride. Some compounds of Formula XXVIII are known, see for example, Gerster, U.S. Pat. No. 4,689,338 and Gerster et al., U.S. Pat. No. 5,605,899.

In step (7) of Reaction Scheme III a 1H-imidazo[4,5-c]quinolin-4-amine of Formula XXVIII is chlorinated using conventional methods to provide a 1H-imidazo[4,5-c]quinolin-4-amine of Formula XVI. A compound of Formula XXVIII can be heated neat with thionyl chloride. Alternatively, phosphorous oxychloride can be added in a controlled fashion to a solution of a compound of Formula XXVIII in a suitable solvent such as N,N-dimethylformamide in the presence of triethylamine.

Steps (8) and (9) of Reaction Scheme III can be carried out in the same manner as steps (7) and (8), respectively, of Reaction Scheme I.

Reaction Scheme III

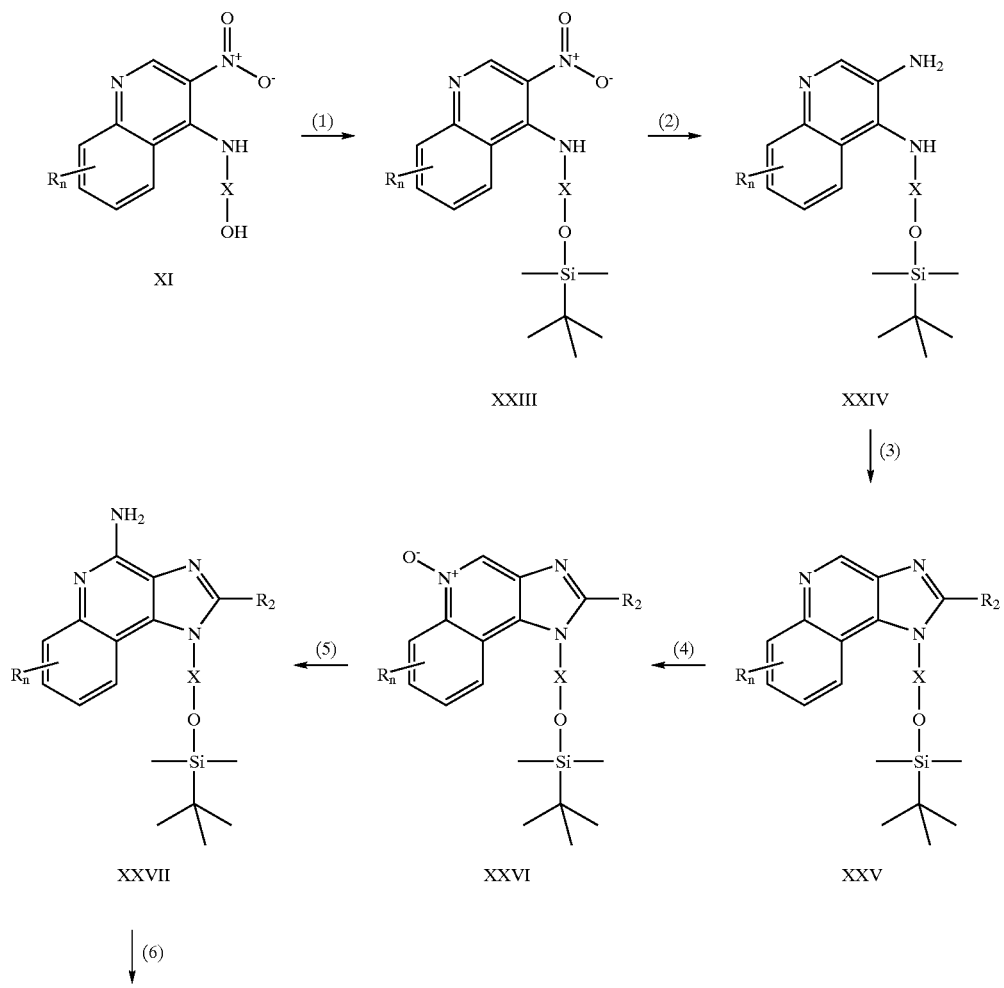

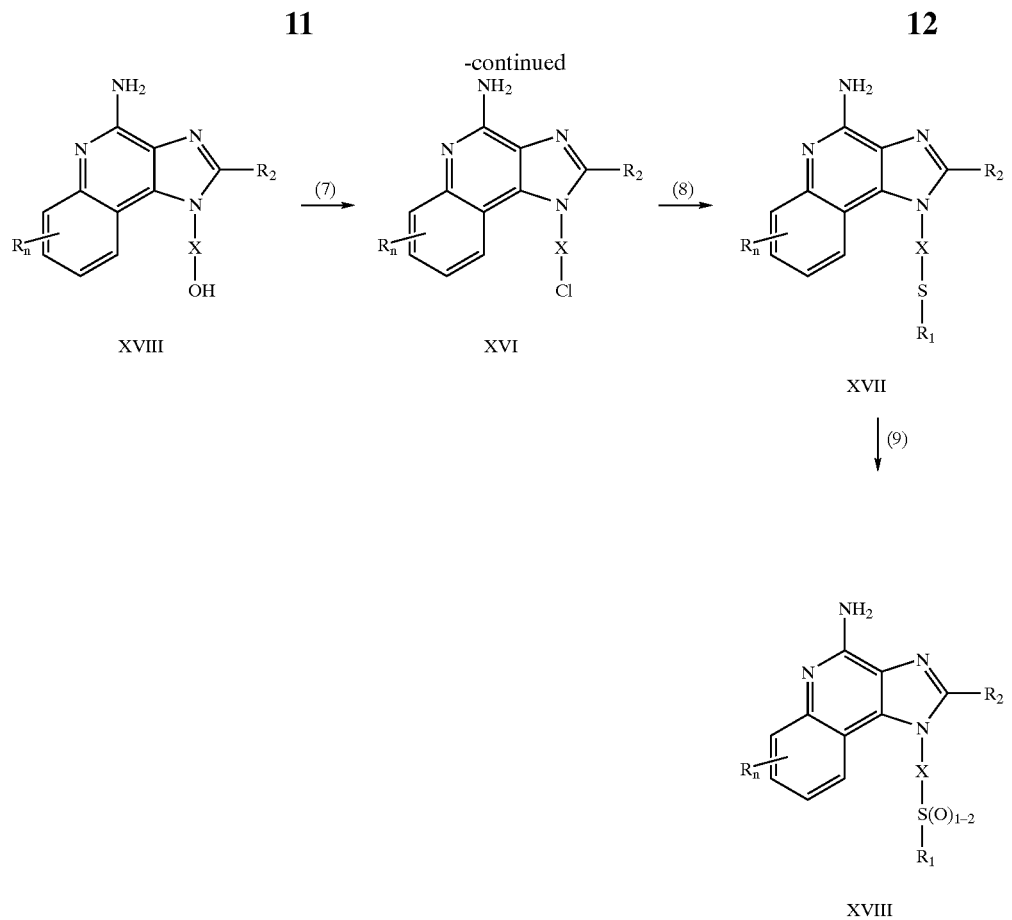

Compounds of the invention can be prepared according to Reaction Scheme IV where R, $R_1$, $R_2$, X and n are as defined above and BOC is tert-butoxycarbonyl.

In step (1) of Reaction Scheme IV the hydroxy group of a 6,7,8,9-tetrahydro-1H-imidazo[4,5-c]quinolin-1-yl alcohol of Formula XXIX is protected with a tert-butyldimethylsilyl group using the method of step (1) of Reaction Scheme III. Compounds of Formula XXIX are known or can be prepared using known synthetic methods, see for example, Nikolaides, et al., U.S. Pat. No. 5,352,784 and Lindstrom, U.S. Pat. No. 5,693,811 and references cited therein.

In step (2) of Reaction Scheme IV the amino group of a 1H-imidazo[4,5-c]quinolin-4-amine of Formula XXX is protected using conventional methods to provide a protected 1H-imidazo[4,5-c]quinoline of Formula XXXI. Preferably a compound of Formula XXX is treated with di-tert-butyl dicarbonate in a suitable solvent such as tetrahydrofuran in the presence of triethylamine and 4-dimethylaminopyridine. The reaction can be run at an elevated temperature (60° C.).

In step (3) of Reaction Scheme IV the tert-butyldimethylsilyl protecting group of a compound of Formula XXXI is removed using the method of step (6) of Reaction Scheme III to provide a 1H-imidazo[4,5-c]quinolin-1yl alcohol of Formula XXXII.

In step (4) of Reaction Scheme IV a 1H-imidazo[4,5-c]quinolin-1yl alcohol of Formula XXXII is converted to a methanesulfonate of Formula XXXIII. Preferably a solution of a compound of Formula XXXII in a suitable solvent such as dichloromethane is treated with methanesulfonyl chloride in the presence of triethylamine. The reaction can be run at a reduced temperature (−10° C.).

In step (5) of Reaction Scheme IV a methanesulfonate of Formula XXXIII is reacted with a thiol of formula $R_1SH$ to provide a thioether of Formula XXXIV. Preferably a solution of a compound of Formula XXXIII in a suitable solvent such as N, N-dimethylformamide is treated with the thiol in the presence of triethylamine. The reaction can be run at an elevated temperature (80° C.).

In step (6) of Reaction Scheme IV the tert-butoxycarbonyl protecting groups are removed by hydrolysis under acidic conditions to provide a 1H-imidazo[4,5-c]quinolin-4-amine of Formula XXXV which is a subgenus of Formula II. Preferably a solution of a compound of Formula XXXIV in a suitable solvent such as dichloromethane is treated at ambient temperature with a solution of hydrochloric acid in dioxane. The product or a pharmaceutically acceptable salt thereof can be isolated using conventional methods.

In step (7) of Reaction Scheme IV a thioether of Formula XXXV is oxidized using the method of step (8) of Reaction Scheme I to provide a sulfone or sulfoxide of Formula XXXVI which is a subgenus of Formula II. The product or a pharmaceutically acceptable salt thereof can be isolated using conventional methods.

Reaction Scheme IV

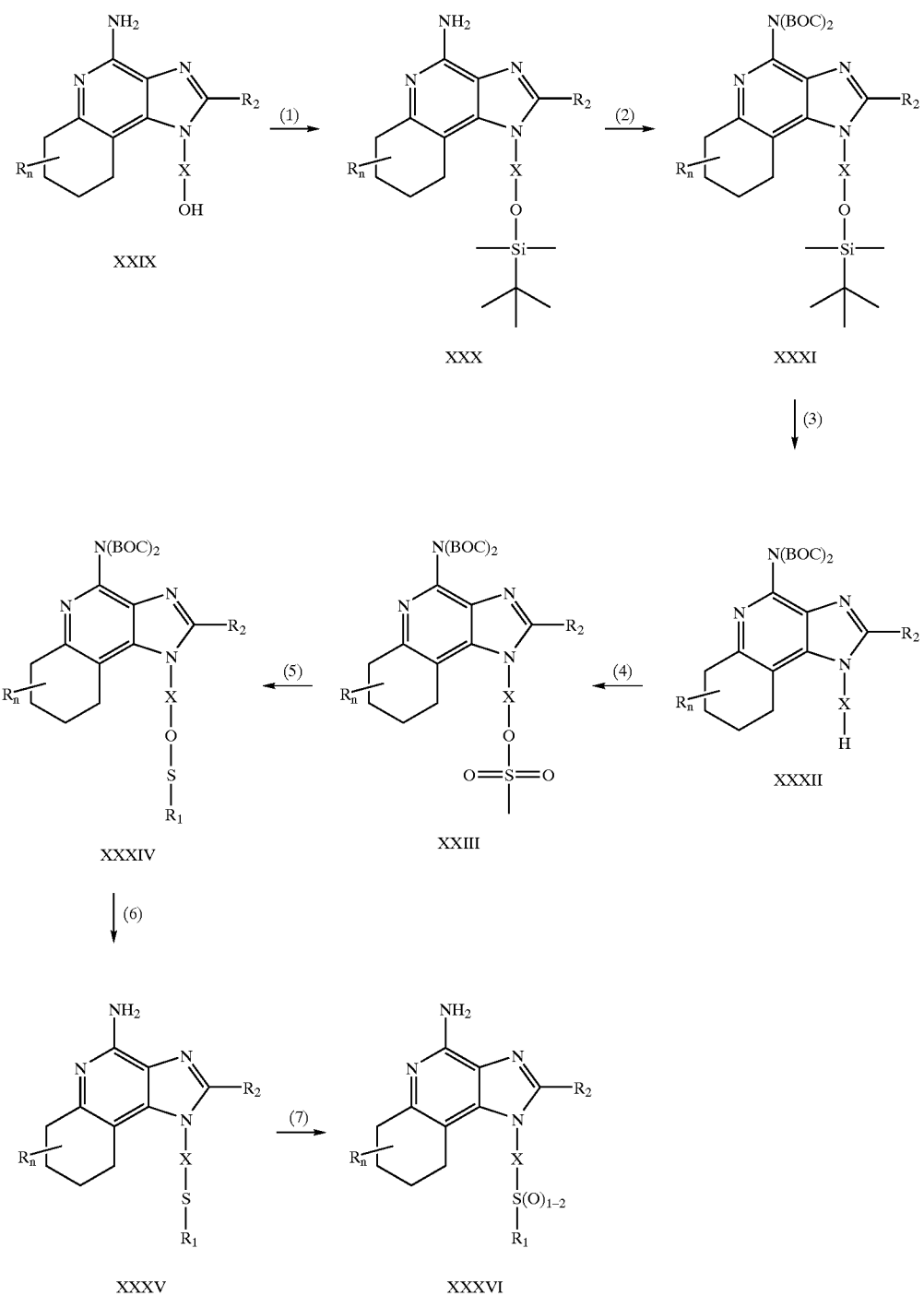

Compounds of the invention can be prepared according to Reaction Scheme V where R, $R_1$, $R_2$, X and n are as defined above.

In step (1) of Reaction Scheme V a 6,7,8,9-tetrahydro-1H-imidazo[4,5-c]quinolin-1-yl alcohol of Formula XXIX is chlorinated using the method of step (7) of Reaction Scheme III to provide a compound of Formula XXXVII.

In step (2) of Reaction Scheme V a compound of Formula XXXVII is reacted with a compound of formula $R_1$—SNa using the method of step (7) of Reaction Scheme I to provide a thioether of Formula XXXV which is a subgenus of Formula II. The product or a pharmaceutically acceptable salt thereof can be isolated using conventional methods.

In step (3) of Reaction Scheme V a thioether of Formula XXXV is oxidized using the method of step (8) of Reaction Scheme I to provide a sulfone or sulfoxide of Formula XXXVI which is a subgenus of Formula II. The product or a pharmaceutically acceptable salt thereof can be isolated using conventional methods.

Reaction Scheme V

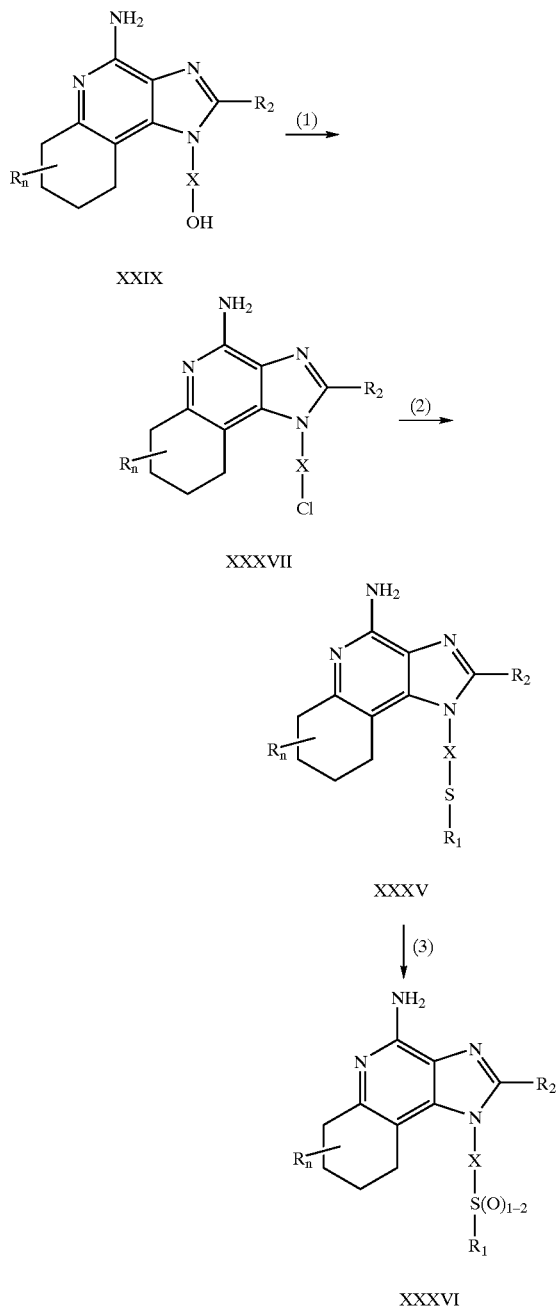

Reaction Scheme VI

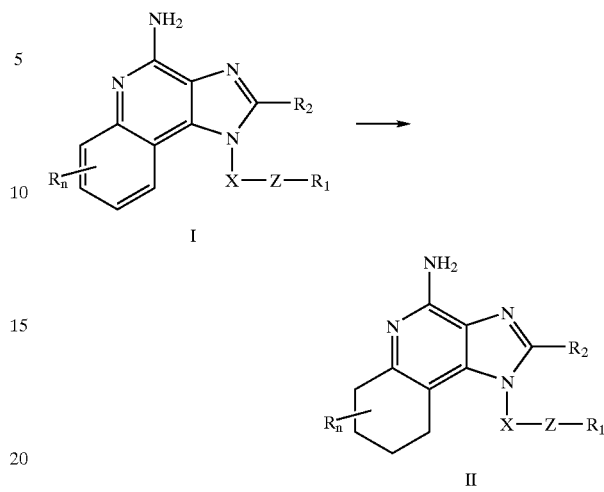

Compounds of the invention can be prepared according to Reaction Scheme VI where R, $R_1$, $R_2$, X, Z and n are as defined above.

In Reaction Scheme VI a 1H-imidazo[4,5-c]quinoline of Formula I is reduced to provide a 6,7,8,9-tetrahydro-1H-imidazo[4,5-c]quinoline of Formula II. The reduction is carried out by dissolving a compound of Formula I in trifluoroacetic acid, adding a catalytic amount of platinum (IV) oxide, then subjecting the mixture to hydrogen pressure. The reaction can conveniently be carried out on a Parr apparatus. The product or a pharmaceutically acceptable salt thereof can be isolated using conventional methods.

Compounds of the invention can be prepared according to Reaction Scheme VII where R, $R_1$, $R_2$, X and n are as defined above and Ph is phenyl.

In step (1) of Reaction Scheme VII a 2,4-dihydroxy-3-nitro-6,7,8,9-tetrahydroquinoline of Formula XXXVIII is chlorinated using conventional chlorinating agents to provide a 2,4-dichloro-3-nitro-6,7,8,9-tetrahydroquinoline of Formula XXXIX. Preferably a compound of Formula XXXVIII is combined with phosphorous oxychloride and heated. Some 2,4-dihydroxy-3-nitro-6,7,8,9-tetrahydroquinolines of Formula XXXVIII are known and others can be prepared using known synthetic methods, see for example, Nikolaides et al., U.S. Pat. No. 5,352,784 and the references cited therein.

In step (2) of Reaction Scheme VII, a 2,4-dichloro-3-nitro-6,7,8,9-tetrahydroquinoline of Formula XXXIX is reacted with an amine of formula HO—X—$NH_2$ to provide a 2-chloro-3-nitro-6,7,8,9-tetrahydroquinoline of Formula XXXX. The reaction can be carried out by adding the amine to a solution of a compound of Formula XXXIX in a suitable solvent such as N,N-dimethylformamide in the presence of triethylamine and optionally heating.

In step (3) of Reaction Scheme VII, a 2-chloro-3-nitro-6,7,8,9-tetrahydroquinoline of Formula XXXX is reacted with sodium phenoxide to provide a 3-nitro-2-phenoxy-6,7,8,9-tetrahydroquinoline of Formula XXXXI. Phenol is reacted with sodium hydride in a suitable solvent such as 1,2-dimethoxyethane to form the phenoxide. The phenoxide is then reacted at an elevated temperature with a compound of Formula XXXX.

In step (4) of Reaction Scheme VII, a 3-nitro-2-phenoxy-6,7,8,9-tetrahydroquinoline of Formula XXXXI is chlorinated using conventional chlorinating agents to provide a 3-nitro-2-phenoxy-6,7,8,9-tetrahydroquinoline of Formula XXXXII. Preferably N-chlorosuccinimide is reacted with triphenylphosphine in a suitable solvent such as tetrahydrofuran to form the phosphino chloride, which is then reacted with a compound of Formula XXXXI.

In Step (5) of Reaction Scheme VII, a 3-nitro-2-phenoxy-6,7,8,9-tetrahydroquinoline of Formula XXXXII is reduced using conventional methods to provide a 3-amino-2-phenoxy-6,7,8,9-tetrahydroquinoline of Formula XXXXIII. A preferred method involves the in situ generation of $Ni_2B$. Sodium borohydride is added to a mixture of nickel(II) chloride hexahydrate and a compound of Formula XXXXII in 50/50 methanol/chloroform.

In step (6) of Reaction Scheme VII, a 3-amino-2-phenoxy-6,7,8,9-tetrahydroquinoline of Formula XXXXIII is cyclized using the method of step (4) of Reaction Scheme I to provide a 4-phenoxy-6,7,8,9-tetrahydro-1H-imidazo[4,5-c]quinoline of Formula III.

In step (7) of Reaction Scheme VII, a 4-phenoxy-6,7,8,9-tetrahydro-1H-imidazo[4,5-c]quinoline of Formula III is reacted with a compound of Formula $R_1SNa$ to provide a 4-phenoxy-6,7,8,9-tetrahydro-6,7,8,9-1H-imidazo[4,5-c]quinoline of Formula XXXXIV which is a subgenus of Formula IV. Preferably a thiol of the Formula $R_1SH$ is reacted with sodium hydride in a suitable solvent such as N,N-dimethylformamide to generate the anion, which is then reacted with a compound of Formula III.

In step (8a) of Reaction Scheme VII, 4-phenoxy-6,7,8,9-tetrahydro-1H-imidazo[4,5-c]quinoline of Formula XXXXIV is aminated to provide a 6,7,8,9-tetrahydro-1H-imidazo[4,5-c]quinoline-4-amine of Formula XXXV which is a subgenus of Formula II. The reaction can be carried out by combining a compound of Formula XXXXIV with ammonium acetate and heating (~150° C.). Optionally, the reaction may be carried out in a pressure vessel. The product or a pharmaceutically acceptable salt thereof can be isolated using conventional methods.

In step (8b) of Reaction Scheme VII, a 4-phenoxy-6,7,8,9-tetrahydro-1H-imidazo[4,5-c]quinoline of Formula XXXXIV is oxidized using the method of step (8) of Reaction Scheme I to provide a 4-phenoxy-6,7,8,9-tetrahydro-1H-imidazo[4,5-c]quinoline of Formula XXXXV which is a subgenus of Formula IV.

In step (9) of Reaction Scheme VII, a 4-phenoxy-6,7,8,9-tetrahydro-1H-imidazo[4,5-c]quinoline of Formula XXXXV is aminated using the method of step (8a) to provide a 6,7,8,9-tetrahydro-1H-imidazo[4,5-c]quinoline-4-amine of Formula XXXVI which is a subgenus of Formula II. The product or a pharmaceutically acceptable salt thereof can be isolated using conventional methods.

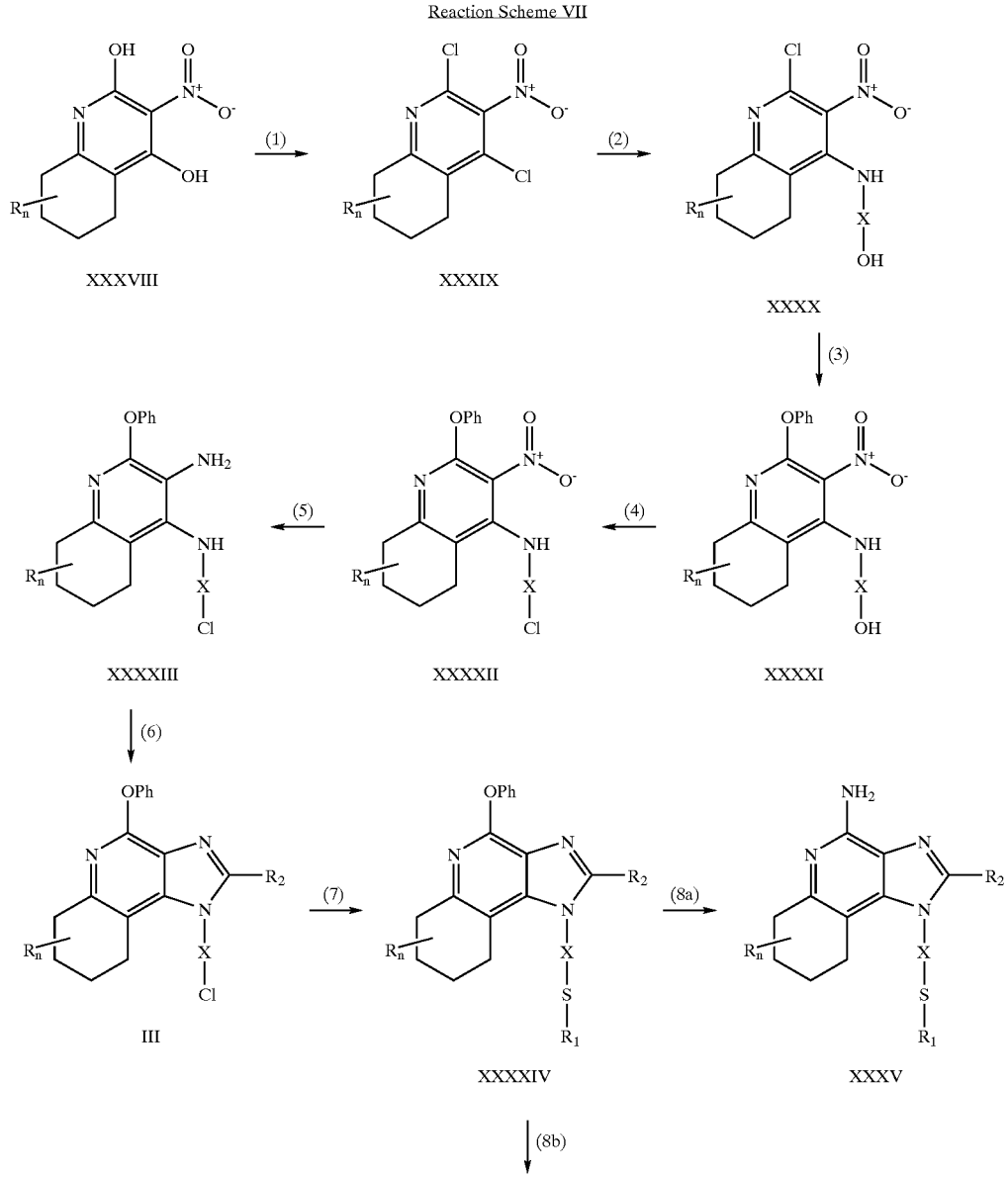

Reaction Scheme VII

The invention also provides novel compounds useful as intermediates in the synthesis of compounds of Formula II. These intermediates have structural Formulas III and IV described in more detail below.

One class of intermediate compounds has the Formula III:

III wherein: X is —CHR$_3$—, —CHR$_3$-alkyl-, or —CHR$_3$-alkenyl-;

R$_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N(R$_3$)$_2$;
  - —CO—N(R$_3$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

each R$_3$ is independently H or C$_{1-10}$ alkyl;

Y is —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

Another class of intermediates has the Formula IV:

IV wherein: X is —CHR$_3$—, —CHR$_3$-alkyl-, or —CHR$_3$-alkenyl-;

Z is —S—, —SO—, or —SO$_2$—;

R$_1$ is selected from the group consisting of:
- -alkyl;
- -aryl;
- -heteroaryl;
- -heterocyclyl;
- -alkenyl;
- —R$_4$-aryl;
- —R$_4$-heteroaryl; and
- —R$_4$-heterocyclyl;

R$_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N(R$_3$)$_2$;
  - —CO—N(R$_3$)$_2$;
  - —CO—C$_{1-10}$ alkyl;
  - —CO—O—C$_{1-10}$ alkyl;
  - —N$_3$;
  - -aryl;
  - -heteroaryl;

-heterocyclyl;
—CO-aryl; and
—CO-heteroaryl;
each $R_3$ is independently H or $C_{1-10}$ alkyl;
$R_4$ is alkylene or alkenylene;
Y is —O— or —S(O)$_{0-2}$—;
n is 0 to 4; and
each R present is independently selected from the group consisting of $C_{1-10}$ alkyl, $C_{1-10}$ alkoxy, hydroxy, halogen and trifluoromethyl;
or a pharmaceutically acceptable salt thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl and adamantyl.

In addition, the alkyl and alkenyl portions of —X— groups can be unsubstituted or substituted by one or more substituents, which subsuituents are selected from the groups consisting of alkyl, alkenyl, aryl, heteroaryl, heterocyclyl, arylalkyl, heteroarylalkyl, and heterocyclylalkyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

The aryl, heteroaryl, and heterocyclyl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylcarbonylamino, and, in the case of heterocyclyl, oxo. If any other groups are identified as being "substituted" or "optionally substituted", then those groups can also be substituted by one or more of the above enumerated substituents.

Certain substituents are generally preferred. For example, preferred X groups include ethylene and n-butylene and preferred $R_1$ groups are alkyl and aryl, with phenyl or substituted phenyl a preferred aryl group. Preferably no R substituents are present (i.e., n is 0). Preferred $R_2$ groups include hydrogen, alkyl groups having 1 to 4 carbon atoms (i.e., methyl, ethyl, propyl, isopropyl, n-butyl, sec-butyl, isobutyl, and cyclopropylmethyl), methoxyethyl, and ethoxymethyl. One or more of these preferred substituents, if present, can be present in the compounds of the invention in any combination.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; variola, particularly variola major; HIV; CMV; VZV; rhinovirus; adenovirus; influenza; and para-influenza; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of Keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLE 1

2-butyl-1-[4-(phenylthio)butyl]-1H-imidazo[4,5-c]quinolin-4-amine

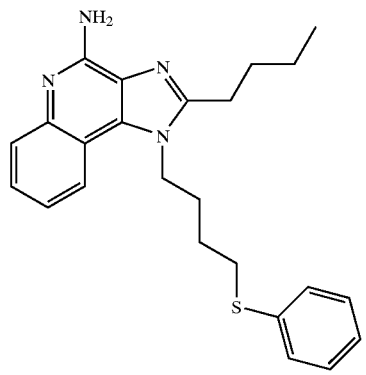

Part A

A round bottom flask was charged with a magnetic stir bar, 4-chloro-3-nitroquinoline (109.70 g, 525.87 mmol) and dichloromethane (500 mL). To the solution was added triethylamine (79.82 g, 788.81 mmol) and 4-amino-1-butanol (46.87 g, 525.87 mmol) to give a homogeneous, dark yellow solution. The reaction was judged to be complete after heating at reflux for 30 minutes. The solution was cooled and then partitioned between chloroform and saturated aqueous ammonium chloride. The layers were separated and the aqueous layer was extracted with chloroform (1×). The organic layers were combined and then concentrated under reduced pressure to afford 4-[(3-nitroquinolin-4-yl)amino]butan-1-ol (104.67 g, 400.60 mmol) as a dark yellow solid. This material was used without further purification.

Part B

A round bottom flask was charged with a magnetic stir bar, 4-[(3-nitroquinolin-4-yl)amino]butan-1-ol (5.0 g, 19.14 mmol), triethylamine (2.91 g, 28.71 mmol), tert-butyldimethylsilyl chloride (3.75 g, 24.9 mmol), 4-dimethylaminopyridine (0.10 g) and chloroform (40 mL) to give a dark yellow solution. The reaction was judged was to complete after stirring at ambient temperature for 2 hours. The solution was partitioned between ethyl acetate and saturated aqueous ammonium chloride. The layers were separated and the organic layer was washed with saturated aqueous sodium bicarbonate, dried over anhydrous sodium sulfate, filtered and then concentrated under reduced pressure to afford N-(4-{[tert-butyl(dimethyl)silyl]oxy}butyl)-3-nitroquinolin-4-amine (6.05 g, 16.11 mmol) as a yellow-green solid. This material was used without further purification. MS (CI) for $C_{19}H_{29}N_3O_3Si$ m/z 376 (MH$^+$), 342, 210.

Part C

A Parr vessel was charged with N-(4-{[tert-butyl(dimethyl)silyl]oxy}butyl)-3-nitroquinolin-4-amine (6.05 g, 16.11 mmol), 5% platinum on carbon (3.0 g), and toluene (32 mL). The vessel was placed on a Parr shaker and pressurized to 50 psi (3.5 Kg/cm$^2$) hydrogen. After shaking for one hour, more catalyst (3.0 g) and toluene (15 mL) were added and the vessel was pressurized to 50 psi (3.5 Kg/cm$^2$) hydrogen and shaking continued. The reaction was judged to be complete after one hour. The catalyst was removed by filtration through fluted paper. The filter cake was washed with toluene (50 mL) and the filtrates were combined. The volatiles were removed under reduced pressure to afford N-(4-{[tert-butyl(dimethyl)silyl]oxy}butyl)quinoline-3,4-diamine (5.57 g, 16.11 mmol) as a dark oil. The material was used without further purification.

Part D

A round bottom flask was charged with a magnetic stir bar, N-(4-{[tert-butyl(dimethyl)silyl]oxy}butyl)quinoline-3,4-diamine (5.57 g, 16.11 mmol), trimethyl orthovalerate (5.23 g, 32.22 mmol) and toluene (47 mL). The reaction was heated to maintain a reflux that brought about a slow distillation to facilitate removal of the methanol byproduct. The reaction was judged to be complete after 15 hours at reflux. The reaction was cooled and the volatiles were removed under reduced pressure to afford of 2-butyl-1-(4-{[tert-butyl(dimethyl)silyl]oxy}butyl)-1H-imidazo[4,5-c]quinoline (4.65 g, 11.30 mmol) as a thick, dark brown oil. The material was used without further purification. MS (CI) for $C_{24}H_{37}N_3OSi$ m/z 412 (MH$^+$), 298.

Part E

A round bottom flask was charged with a magnetic stir bar, 2-butyl-1-(4-{[tert-butyl(dimethyl)silyl]oxy}butyl)-1H-imidazo[4,5-c]quinoline (4.65 g, 11.30 mmol) and chloroform (57 mL). Solid 3-chloroperbenzoic acid (2.78 g, 12.43 mmol) was added portion wise to the solution over 15 minutes and the reaction was stirred at ambient temperature for 1 hour. More 3-chloroperbenzoic acid (0.5 g, 2.9 mmol) was added and after 30 minutes the starting material was completely consumed. The solution was partitioned between chloroform and aqueous saturated sodium bicarbonate. The layers were separated. The organic layer was washed with saturated aqueous sodium bicarbonate and brine, dried over anhydrous sodium sulfate, filtered and then concentrated under reduced pressure to afford 2-butyl-1-(4-{[tert-butyl(dimethyl)silyl]oxy}butyl)-1H-imidazo[4,5-c]quinoline-5N-oxide (4.83 g, 11.30 mmol) as a dark oil. The material was used without further purification.

Part F

A round bottom flask was charged with a magnetic stir bar, 2-butyl-1-(4-{[tert-butyl(dimethyl)silyl]oxy}butyl)-1H-imidazo[4,5-c]quinoline-5N-oxide (11.30 mmol) and anhydrous dimethyl formamide (57 mL) under a nitrogen atmosphere. Phosphorus oxychloride (1.91 g, 12.43 mmol) was added to the reaction mixture in a drop wise fashion to give a homogeneous solution after complete addition. The reaction was judged to be complete after stirring for 1.5 hours at ambient temperature and was then partitioned between dichloromethane and saturated aqueous sodium bicarbonate. The layers were separated and the organic portion was washed with aqueous saturated sodium bicarbonate and brine, dried over anhydrous sodium sulfate, filtered and then concentrated under reduced pressure to afford 2-butyl-4-chloro-1-(4-chlorobutyl)-1H-imidazo[4,5-c]quinoline (3.65 g, 10.42 mmol) as a dark brown solid. The material was used without further purification. MS (CI) for $C_{18}H_{21}Cl_2N_3$ m/z 350 (MH$^+$), 314.

Part G

A round bottom flask was charged with a magnetic stir bar, 2-butyl-4-chloro-1-(4-chlorobutyl)-1H-imidazo[4,5-c]quinoline (1.18 g, 3.37 mmol), benzenethiol (0.56 g, 5.05 mmol), triethylamine (0.68 g, 6.74 mmol), and dimethyl formamide (15 mL) under a nitrogen atmosphere. The reaction mixture was heated to 80° C. to give a homogeneous solution that was maintained at 80° C. for 2.5 hours. HPLC analysis indicated no starting material and a 3:1 mixture of 2-butyl-4-chloro-1-[4-(phenylthio)butyl]-1H-imidazo[4,5-c]quinoline and 2-butyl-4-(phenylthio)-1-[4-(phenylthio)butyl]-1H-imidazo[4,5-c]quinoline. The solution was cooled and then partitioned between ethyl acetate and aqueous saturated sodium bicarbonate. The layers were separated and the organic layer was washed with aqueous saturated sodium bicarbonate and brine, dried over anhydrous sodium sulfate, filtered and then concentrated under reduced pressure to afford a 3:1 mixture of the products named above (1.43 g). The material was used without further purification.

Part H

A 3:1 mixture of 2-butyl-4-chloro-1-[4-(phenylthio) butyl]-1H-imidazo[4,5-c]quinoline to 2-butyl-4-(phenylthio)-1-[4-(phenylthio)butyl]-1H-imidazo[4,5-c]quinoline (1.38 g) and a solution of 7% ammonia in methanol (30 mL) were combined in a bomb and heated to 150° C. The reaction was judged to be complete after 5 hours. The volatiles were removed under reduced pressure and the resulting residue was stirred in water and made basic (pH 10) with solid sodium carbonate. The aqueous mixture was extracted with chloroform (3x). The combined organic layers were washed with saturated aqueous sodium bicarbonate and brine, dried over anhydrous sodium sulfate, filtered and then concentrated under reduced pressure to afford a yellow crystalline solid. The solid (0.8 g) was dissolved in ethyl acetate (50 mL) and brought to reflux. Activated charcoal (0.4 g) was added; the resulting mixture was heated at reflux for 5 minutes and then the charcoal was removed by filtration through fluted paper to provide a colorless solution. The solution was concentrated under reduced pressure to give a solid that was recrystallized from ethyl acetate and hexanes to provide 2-butyl-1-[4-(phenylthio)butyl]-1H-imidazo[4,5-c]quinolin-4-amine (0.51 g, 1.25 mmol) as white needles, m.p. 118–120° C.

Analysis. Calculated for $C_{24}H_{28}N_4S$: % C 71.25; % H, 6.98; % N, 13.85. Found % C 71.12; % H, 6.81; % N, 13.62. $^1$H-NMR (300 MHz, DMSO) δ 8.02 (d, J=8.3 Hz, 1H), δ 7.61 (d, J=8.3 Hz, 1H), δ 7.41 (t, J=8.3 Hz, 1H), δ 7.16–7.30 (m, 6H), δ 6.46 (bs, 2H), δ 4.52 (t, J=7.6 Hz, 2H), δ 3.02 (t, J=7.3 Hz, 2H), δ 2.89 (t, J=7.8 Hz, 2H), δ 1.95 (m, 2H), δ 1.75 (m, 4H), δ 1.43 (sextet, J=7.3 Hz, 2H), δ 0.94 (t, J=7.3 Hz, 3H) MS (CI) for $C_{24}H_{28}N_4S$ m/z 405 (MH$^+$), 282, 241.

EXAMPLE 2

2-butyl-1-[2-(phenylthio)ethyl]-6,7,8,9-tetrahydro-1H-imidazo[4,5-c]quinolin-4-amine hydrochloride

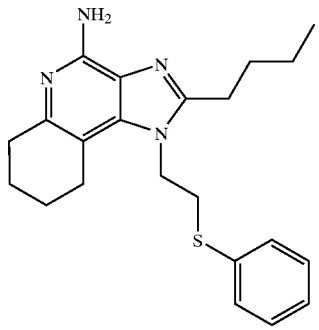

Part A

A round bottom flask was charged with a magnetic stir bar, 2-(4-amino-2-butyl-6,7,8,9-tetrahydro-1H-imidazo[4,5-c]quinolin-1-yl)ethanol (1.0 g, 3.47 mmol), tert-butyldimethylsilyl chloride (1.62 g, 10.75 mmol), triethylamine (1.58 g, 15.62 mmol), 4-dimethylaminopyridine (0.1 g), and chloroform (30 mL) to give a heterogeneous reaction mixture. The reaction was judged to be complete after stirring at 60° C. for 2 hours. The solution was partitioned between ethyl acetate and saturated aqueous ammonium chloride. The layers were separated and the organic layer was washed with aqueous saturated sodium bicarbonate and brine, dried over anhydrous sodium sulfate, filtered and then concentrated under reduced pressure to afford a 3:1 mixture of 2-butyl-1-(2-{[tert-butyl(dimethyl)silyl]oxy}ethyl)-6,7,8,9-tetrahydro-1H-imidazo[4,5-c]quinolin-4-amine and 2-butyl-N-[tert-butyl(dimethyl)silyl]-1-(2-{[tert-butyl(dimethyl)silyl]oxy}ethyl)-6,7,8,9-tetrahydro-1H-imidazo[4,5-c]quinolin-4-amine (1.79 g) as a dark brown oil. The material was used without further purification.

Part B

A round bottom flask was charged with a magnetic stir bar, a 3:1 mixture of 2-butyl-1-(2-{[tert-butyl(dimethyl)silyl]oxy}ethyl)-6,7,8,9-tetrahydro-1H-imidazo[4,5-c]quinolin-4-amine and 2-butyl-N-[tert-butyl(dimethyl)silyl]-1-(2-{[tert-butyl(dimethyl)silyl]oxy}ethyl)-6,7,8,9-tetrahydro-1H-imidazo[4,5-c]quinolin-4-amine (1.6 g) and a 1 M solution of acetic acid in dichloromethane (85 mL) to provide a homogenous solution. The reaction was judged to be complete after stirring at ambient temperature for 30 minutes. The solution was partitioned between chloroform and brine. The layers were separated and the organic layer was washed with aqueous saturated sodium bicarbonate and brine, dried over anhydrous sodium sulfate, filtered and then concentrated under reduced pressure to afford a dark brown oil. The material was purified by chromatography over silica gel (95/4/1 dichloromethane/methanol/ammonium hydroxide [14.8 M in water]) to provide 2-butyl-1-(2-{[tert-butyl(dimethyl)silyl]oxy}ethyl)-6,7,8,9-tetrahydro-1H-imidazo[4,5-c]quinolin-4-amine (1.24 g, 3.10 mmol) as a colorless oil.

Part C

A round bottom flask was charged with a magnetic stir bar, 2-butyl-1-(2-{[tert-butyl(dimethyl)silyl]oxy}ethyl)-6,7,8,9-tetrahydro-1H-imidazo[4,5-c]quinolin-4-amine (0.83 g, 2.06 mmol), di-tert-butyl dicarbonate (1.79 g; 8.24 mmol), triethylamine (0.52 g, 5.15 mmol), 4-dimethylaminopyridine (0.1 g), and anhydrous tetrahydrofuran (21 mL) under a nitrogen atmosphere. The reaction mixture was heated to 60° C. to give a homogeneous solution that was maintained at 60° C. for 2.5 hours at which time the reaction was judged to be complete. The solution was cooled to ambient temperature and a 1 M solution of tetrabutylammonium fluoride in tetrahydrofuran (2.27 mL, 2.27 mmol) was added. The reaction was judged to be complete after stirring at ambient temperature for 30 minutes. The solution was partitioned between ethyl acetate and saturated aqueous ammonium chloride. The layers were separated. The organic layer was washed with saturated aqueous sodium bicarbonate and brine, dried over anhydrous sodium sulfate, filtered and then concentrated under reduced pressure to afford a light yellow solid. The material was purified by chromatography over silica gel (95/5 dichloromethane/methanol) to provide di(tert-butyl) 2-butyl-1-(2-hydroxyethyl)-6,7,8,9-tetrahydro-1H-imidazo[4,5-c]quinolin-4-ylimidodicarbonate (0.55 g, 1.13 mmol) as a clear gum.

Part D

A round bottom flask was charged with a magnetic stir bar, di(tert-butyl) 2-butyl-1-(2-hydroxyethyl)-6,7,8,9-tetrahydro-1H-imidazo[4,5-c]quinolin-4-ylimidodicarbonate (0.55 g, 1.13 mmol) and anhydrous dichloromethane (11 mL) under a nitrogen atmosphere. The resulting homogeneous solution was cooled to −10° C. in a methanol/ice bath. To the cooled solution was added triethylamine (0.23 g, 2.26 mmol) and methanesulfonyl chloride (0.19 g, 1.70 mmol). The reaction was judged to be complete after stirring at −10° C. for 15 minutes and was then partitioned between ethyl acetate and saturated aqueous ammonium chloride. The layers were separated. The organic layer was washed with saturated aqueous sodium bicarbonate and brine, dried over anhydrous sodium sulfate, filtered and then concentrated under reduced pressure to afford 2-{4-[bis(tert-butoxycarbonyl)amino]-2-butyl-6,7,8,9-tetrahydro-1H-imidazo[4,5-c]quinolin-1-yl}ethyl methanesulfonate (0.61 g, 1.08 mmol) as a gummy yellow solid. The material was used without further purification. MS (CI) for $C_{27}H_{42}N_4O_7S$ m/z 567 (MH$^+$), 467, 367, 271.

Part E

A round bottom flask was charged with a magnetic stir bar, 2-{4-[bis(tert-butoxycarbonyl)amino]-2-butyl-6,7,8,9-tetrahydro-1H-imidazo[4,5-c]quinolin-1-yl}ethyl methanesulfonate (0.61 g, 1.08 mmol), benzenethiol (0.21 g, 1.88 mmol), triethylamine (0.25 g, 2.43 mmol) and anhydrous dimethyl formamide (11 mL) under a nitrogen atmosphere. The reaction mixture was heated to 80° C. to give a dark yellow, homogeneous solution that was maintained at 80° C. for 2.5 hours at which time the reaction was judged to be complete. The solution was cooled and then partitioned between ethyl acetate and saturated aqueous sodium bicarbonate. The layers were separated. The organic layer was washed with saturated aqueous sodium bicarbonate and brine, dried over anhydrous sodium sulfate, filtered and then concentrated under reduced pressure to afford a yellow oil. The material was purified by chromatography over silica gel (95/5 dichloromethane/methanol) to provide di(tert-butyl) 2-butyl-1-[2-(phenylthio)ethyl]-6,7,8,9-tetrahydro-1H-imidazo[4,5-c]quinolin-4-ylimidodicarbonate (0.54 g, 0.93 mmol) as a light yellow oil. MS (CI) for $C_{32}H_{44}N_4O_4S$ m/z 581 (MH$^+$), 481, 381, 245.

Part F

A round bottom flask was charged with a magnetic stir bar, di(tert-butyl) 2-butyl-1-[2-(phenylthio)ethyl]-6,7,8,9-tetrahydro-1H-imidazo[4,5-c]quinolin-4-ylimidodicarbonate (0.50 g, 0.86 mmol), a 4 M solution of hydrochloric acid in dioxane (5 mL), and dichloromethane (5 mL). The reaction was judged to be complete after stirring at ambient temperature for 2 hours. The volatiles were removed under reduced pressure to afford an off white solid. The material was recrystallized from acetonitrile to provide 2-butyl-1-[2-(phenylthio)ethyl]-6,7,8,9-tetrahydro-1H-imidazo[4,5-c]quinolin-4-amine hydrochloride (0.17 g, 1.30 mmol) as fluffy white needles, m.p. 237–238° C. Analysis. Calculated for $C_{22}H_{28}N_4S \cdot (H_2O)_{1/4} \cdot (HCl)_2$: % C 57.70; % H, 6.71; % N, 12.23. Found % C 57.62; % H, 6.57; % N, 12.41. $^1$H-NMR (300 MHz, DMSO) δ 7.81 (bs, 2H), δ 7.22–7.39 (m, 5H), δ 4.64 (t, J=6.8 Hz, 2H), δ 3.40 (t, J=6.8 Hz, 2H), δ 2.75 (m, 6H), δ 1.71 (m, 6H), δ 1.34 (sextet, J=7.3 Hz, 2H), δ 0.89 (t, J=7.3 Hz, 3H). MS (CI) for $C_{22}H_{28}N_4S$ $(H_2O)_{1/4}$ $(HCl)_2$ m/z 381 (MH$^+$), 245, 137.

EXAMPLE 3

2-butyl-1-[4-(phenylsulfonyl)butyl]-1H-imidazo[4,5-c]quinolin-4-amine

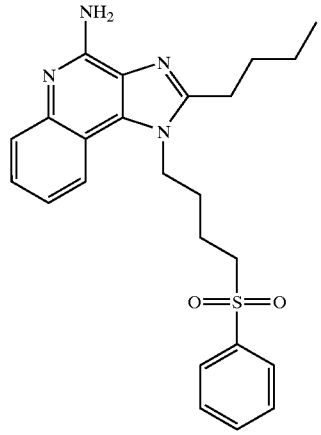

Part A

Using the general method of Example 1 Part E, 2-butyl-1-(4-{[tert-butyl(dimethyl)silyl]oxy}butyl)-1H-imidazo[4,5-c]quinoline (16.0 g, 38.87 mmol) was oxidized to 2-butyl-1-(4-{[tert-butyl(dimethyl)silyl]oxy}butyl)-1H-imidazo[4,5-c]quinoline-5N-oxide (16.61 g, 38.87 mmol) which was isolated without purification as a tan solid.

Part B

A round bottom flask was charged with a magnetic stir bar, 2-butyl-1-(4-{[tert-butyl(dimethyl)silyl]oxy}butyl)-1H-imidazo[4,5-c]quinoline-5N-oxide (16.61 g, 38.87 mmol), a 14.8 M solution of ammonium hydroxide in water (75 mL) and chloroform (200 mL). To the rapidly stirring solution was added p-toluenesulfonyl chloride (8.15 g, 42.76 mmol) in a portion wise fashion resulting in a mild exotherm. The reaction was judged to be complete after stirring at ambient temperature for 10 minutes. The solution was partitioned between chloroform and aqueous saturated sodium bicarbonate. The layers were separated. The organic layer was washed with saturated aqueous sodium bicarbonate and brine, dried over anhydrous sodium sulfate, filtered and then concentrated under reduced pressure to afford an off-white solid. The material was triturated with ethyl ether and collected by filtration to provide 2-butyl-1-(4-{[tert-butyl (dimethyl)silyl]oxy}butyl)-1H-imidazo[4,5-c]quinolin-4-amine (9.3 g, 21.80 mmol) as a fine white powder. The material was used without further purification.

Part C

A round bottom flask was charged with a magnetic stir bar, 2-butyl-1-(4-{[tert-butyl(dimethyl)silyl]oxy}butyl)-1H-imidazo[4,5-c]quinolin-4-amine (9.2 g, 21.56 mmol), a 1M solution of tetrabutylammonium fluoride in tetrahydrofuran (23.72 mL, 23.72 mmol), and anhydrous tetrahydrofuran (100 mL) to give a homogeneous, light orange solution. The reaction was judged to be complete after stirring at ambient temperature for 1 hour. While stirring, water (100 mL) was added and resulted in a mild exotherm. The volatiles were removed under reduced pressure until a solid precipitated out of solution. The solid was collected by filtration and washed with water (20 mL) and acetone (20 mL) to afford a white solid. The material was triturated with ethyl ether (50 mL) and collected by filtration to provide 4-(4-amino-2-butyl-1H-imidazo[4,5-c]quinolin-1-yl)butan-1-ol (6.12 g, 19.59 mmol) as a fine white solid, m.p. 184–186° C.

Analysis. Calculated for $C_{18}H_{24}N_4O$: % C 69.20; % H, 7.74; % N, 17.93. Found % C 69.05; % H, 8.02; % N, 18.03. MS (CI) for $C_{18}H_{24}N_4O$ m/z 313 (MH$^+$).

Part D

A round bottom flask was charged with a magnetic stir bar, 4-(4-amino-2-butyl-1H-imidazo[4,5-c]quinolin-1-yl)butan-1-ol (7.3 g, 23.37 mmol), triethylamine (3.55 g, 35.06 mmol), and anhydrous dimethyl formamide (93 mL) under a nitrogen atmosphere. To the stirred solution was added phosphorus oxychloride (3.94 g, 25.70 mmol) in a drop wise fashion resulting in an exotherm to give a dark yellow heterogeneous reaction mixture. The reaction mixture was heated to 60° C. to give a homogeneous solution that was maintained at 60° C. for 5 hours at which time the starting material was completely consumed. The volatiles were removed under reduced pressure to give a dark brown oil. The material was partitioned between chloroform and saturated aqueous sodium bicarbonate. The layers were separated and the aqueous layer was extracted with chloroform (1×). The organic layers were combined and the volatiles removed under reduced pressure to afford a 2:1 mixture of N'-[2-butyl-1-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (7.70 g) as an off-white solid. The material was used without further purification.

Part E

A round bottom flask was charged with a magnetic stir bar, a 2:1 mixture of N'-[2-butyl-1-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (1.3 g), benzenesulfinic acid sodium salt (1.67 g, 10.11 mmol), and anhydrous dimethyl formamide (15 mL) under a nitrogen atmosphere. The resulting solution was heated to 100° C. to give a homogeneous solution that was maintained at 100° C. for 90 hours at which time the starting materials were completely consumed. The solution was cooled and then partitioned between chloroform and water. The layers were separated. The organic layer was washed with saturated aqueous sodium bicarbonate and brine, dried over anhydrous sodium sulfate, filtered and then concentrated under reduced pressure to afford a dark yellow gum. The material was dissolved in methanol (20 mL) and a 4 M solution of hydrochloric acid in dioxane (3.02 mL, 12.1 mmol). The light orange solution was stirred at ambient temperature for 12 hours at which time the reaction was judged to be complete. The volatiles were removed under reduced pressure to give a light yellow gum. The material was partitioned between chloroform and saturated aqueous sodium bicarbonate. The layers were separated and the aqueous layer was extracted with chloroform (1×). The organic layers were combined, washed with brine, dried over anhydrous sodium sulfate, filtered and then concentrated under reduced pressure to afford a light yellow solid. The material was purified by chromatography over silica gel (95/5 dichloromethane/methanol) to give an off-white solid. The solid (0.63 g) was dissolved in ethyl acetate (50 mL) and brought to reflux. Activated charcoal (0.6 g) was added and the resulting mixture was heated at reflux for 5 minutes. The charcoal was removed by filtration through fluted paper to provide a colorless solution. The solution was concentrated under reduced pressure to give a solid that was recrystallized from ethyl acetate and hexanes to provide 2-butyl-1-[4-(phenylsulfonyl)butyl]-H-imidazo[4,5-c]quinolin-4-amine (0.37 g, 0.85 mmol) as a white fluffy solid, m.p. 179–180° C. Analysis. Calculated for $C_{24}H_{28}N_4O_2S$: % C 66.03; % H, 6.46; % N, 12.83. Found % C 65.88; % H, 6.49; % N, 12.76.

$^1$H-NMR (300 MHz, DMSO) δ 7.98 (d, J=8.3 Hz, 1H), δ 7.82 (m, 2H) δ 7.73 (d, J=7.3 Hz, 1H), δ 7.62 (m, 3H) δ 7.41 (t, J=7.6 Hz, 1H), δ 7.22 (t, J=7.6 Hz, 1H), δ 6.45 (bs, 2H), δ 4.51 (t, J=7.3 Hz, 2H), δ 3.90 (t, J=7.8 Hz, 2H), δ 2.86 (t, J=7.6 Hz, 3H), δ 1.69–1.90 (m, 6H), δ 1.43 (sextet, J=7.3 Hz, 2H), δ 0.95 (t, J=7.3 Hz, 3H) MS (CI) for $C_{24}H_{28}N_4O_2S$ m/z 437 (MH$^+$), 295.

EXAMPLE 4

2-butyl-1-[4-(methylthio)butyl]-1H-imidazo[4,5-c]quinolin-4-amine

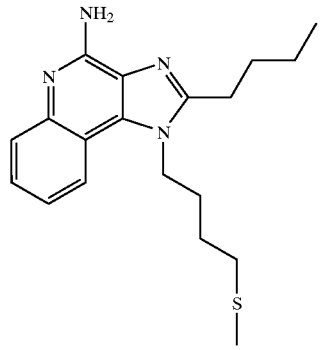

Part A

A round bottom flask was charged with a magnetic stir bar, a 2:1 mixture of N'-[2-butyl-1-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (6.17 g), a 4 M solution of hydrochloric acid in dioxane (21.15 mL, 84.56 mmol), and methanol (200 mL) to provide a light orange solution. The reaction was judged to be complete after stirring at ambient temperature for 43 hours. The volatiles were removed under reduced pressure and the resulting light yellow solid was partitioned between chloroform and saturated aqueous sodium bicarbonate. The layers were separated and the aqueous layer was extracted with chloroform (1×). The organic layers were combined, dried over anhydrous sodium sulfate, filtered and then concentrated under reduced pressure to afford 2-butyl-1-(4-chlorobutyl)-1H-imidazo[4,5-c]quinolin-4-amine (4.65 g, 14.05 mmol) as an off-white solid. The material was used without further purification. MS (CI) for $C_{18}H_{23}ClN_4$ m/z 331 (MH$^+$), 295.

Part B

A round bottom flask was charged with a magnetic stir bar, 2-butyl-1-(4-chlorobutyl)-1H-imidazo[4,5-c]quinolin-4-amine (1.5 g, 4.53 mmol), sodium thiomethoxide (0.48 g, 6.80 mmol), and anhydrous dimethyl formamide (18 mL) under a nitrogen atmosphere. The reaction mixture was heated to 60° C. to give a homogeneous solution that was maintained at 60° C. for 16 hours at which time the starting material was completely consumed. The solution was cooled and then partitioned between chloroform and water. The layers were separated and the organic layer was washed with saturated aqueous sodium bicarbonate. The combined aqueous layers were extracted with chloroform (1×). The combined organic layers were washed with brine, dried over anhydrous sodium sulfate, filtered and then concentrated under reduced pressure to afford a dark brown oil. The material was purified by chromatography over silica gel (90/10 dichloromethane/methanol) to provide a light yellow solid. The solid was recrystallized from dimethyl formamide and water to give 2-butyl-1-[4-(methylthio)butyl]-1H-imidazo[4,5-c]quinolin-4-amine (0.83 g, 2.42 mmol) as light yellow needles, m.p. 127–130° C.

Analysis. Calculated for $C_{19}H_{26}N_4S$: % C 66.63; % H, 7.65; % N, 16.36. Found % C 66.68; % H, 7.53; % N, 16.35 $^1$H-NMR (500 MHz, DMSO) δ 8.04 (d, J=8.3 Hz, 1H), δ 7.61 (d, J=8.3 Hz, 1H), δ 7.41 (t, J=8.3 Hz, 1H), δ 7.25 (t, J=8.3 Hz, 1H), δ 6.43 (bs, 2H), δ 4.52 (t, J=7.6 Hz, 2H), δ 2.92 (t, J=7.8 Hz, 2H), δ 2.53 (t, J=7.3 Hz, 2H), δ 2.01 (s, 3H), δ 1.90 (m, 2H) δ 1.80 (p, J=7.8 Hz, 2H) δ 1.71 (p, J=7.3 Hz, 2H) δ 1.46 (sextet, J=7.3 Hz, 2H), δ 0.96 (t, J=7.3 Hz, 3H) MS (CI) for $C_{19}H_{26}N_4S$ m/z 343 (MH$^+$), 295, 241.

EXAMPLE 5

2-butyl-1-[4-(methylsulfonyl)butyl]-1H-imidazo[4,5-c]quinolin-4-amine

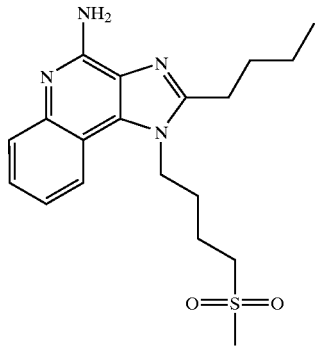

Part A

A round bottom flask was charged with a magnetic stir bar, 2-butyl-1-[4-(methylthio)butyl]-1H-imidazo[4,5-c]quinolin-4-amine (1.2 g, 3.50 mmol), and chloroform (18 mL). Solid 3-chloroperbenzoic acid (1.72 g, 7.71 mmol) was added to the resulting solution portion wise over 15 minutes. The reaction was judged to be complete after stirring at ambient temperature for 5 minutes. The solution was partitioned between chloroform and 1% aqueous sodium carbonate. The layers were separated and the organic layer was washed with brine, dried over anhydrous sodium sulfate, filtered and then concentrated under reduced pressure to afford a light brown solid. The material was purified by chromatography over silica gel (90/10 dichloromethane/methanol) to provide an off-white solid. The solid was recrystallized from acetonitrile and water to give 2-butyl-1-[4-(methylsulfonyl)butyl]-1H-imidazo[4,5-c]quinolin-4-amine (0.61 g, 1.63 mmol) as off-white needles, m.p. 164–165° C.

Analysis. Calculated for $C_{19}H_{26}N_4O_2S$: % C 60.94; % H, 7.00; % N, 14.96. Found % C 60.71; % H, 6.94; % N, 14.94. $^1$H-NMR (300 MHz, DMSO) δ 8.03 (d, J=8.3 Hz, 1H), δ 7.61 (d, J=8.3 Hz, 1H), δ 7.42 (t, J=8.3 Hz, 1H), δ 7.26 (t, J=8.3 Hz, 1H), δ 6.46 (bs, 2H), δ 4.56 (t, J=7.6 Hz, 2H), δ 3.21 (t, J=7.3 Hz, 2H), δ 2.96 (s, 3H), δ 2.93 (t, J=7.8Hz, 2H), δ 1.91 (m, 4H), δ 1.81 (p, J=7.3 Hz, 2H), δ 1.45 (sextet, J=7.3 Hz, 2H), δ 0.96 (t, J=7.3 Hz, 3H) MS (CI) for $C_{19}H_{26}N_4O_2S$ m/z 375 (MH$^+$), 295

EXAMPLE 6

1-[2-(phenylthio)ethyl]-1H-imidazo[4,5-c]quinolin-4-amine

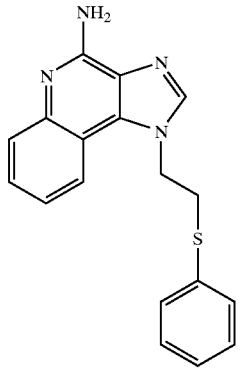

Part A

A round bottom flask was charged with a magnetic stir bar, 2-(4-amino-1H-imidazo[4,5-c]quinolin-1-yl)ethanol (8.46 g, 37.06 mmol), and thionyl chloride (68.99 g, 57.99 mmol) under a nitrogen atmosphere. The reaction mixture was heated to 80° C. to give a heterogeneous reaction mixture that was maintained at 80° C. for 2 hours at which time the starting material was completely consumed. The solution was cooled and quenched by the addition of water (400 mL). To the stirred solution was added solid sodium carbonate until the pH reached 10 at which time a solid precipitated out of solution. The solid was collected by filtration to afford 1-(2-chloroethyl)-1H-imidazo[4,5-c]quinolin-4-amine (7.86 g, 31.86 mmol) as an off-white solid. The material was used without further purification.

Part B

A round bottom flask was charged with a magnetic stir bar, 1-(2-chloroethyl)-1H-imidazo[4,5-c]quinolin-4-amine (2.0 g, 8.11 mmol), sodium benzenethiolate (1.79 g, 12.16 mmol), and anhydrous dimethyl sulfoxide (40 mL) under a nitrogen atmosphere. The reaction mixture was heated to 100° C. to give a homogeneous solution that was maintained at 100° C. for 30 minutes at which time the starting material was completely consumed. The hot solution was poured into rapidly stirred water (300 mL) which caused a solid to precipitate out of solution. The solid was collected by filtration to afford an off-white solid. The material was triturated with acetonitrile and collected by filtration to give 1-[2-(phenylthio)ethyl]-1H-imidazo[4,5-c]quinolin-4-amine (2.08 g, 6.49 mmol) as an off-white powder, m. p. 233–235° C.

Analysis. Calculated for $C_{18}H_{16}N_4S$: % C 67.47; % H, 5.03; % N, 17.49. Found: % C 67.20; % H, 4.95; % N, 17.52 $^1$H-NMR (300 MHz, DMSO) δ 8.14 (s, 1H), δ 7.76 (d, J=8.3 Hz, 1H), δ 7.60 (t, J=8.3 Hz, 1H), δ 7.28–7.44 (m, 6H), δ 7.12 (t, J=8.3 Hz, 1H), δ 6.58 (bs, 2H), δ 4.79 (t, J=6.8 Hz, 2H), δ 3.48 (t, J=6.8 Hz, 2H) MS (CI) for $C_{18}H_{16}N_4S$ m/z 321 (MH$^+$), 185, 137

EXAMPLE 7

1-[4-(phenylsulfonyl)butyl]-1H-imidazo[4,5-c]
quinolin-4-amine

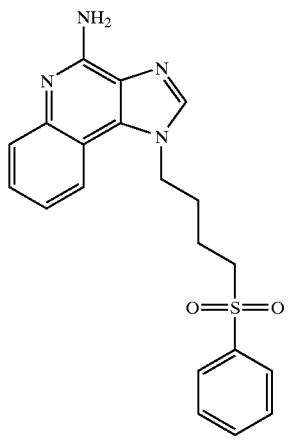

Part A

A round bottom flask was charged with a magnetic stir bar, N,N-dibenzyl-1H-imidazo[4,5-c]quinolin-4-amine (20.0 g, 55.04 mmol), sodium hydride (3.3 g, 60% dispersion, 82.56 mmol), and anhydrous dimethyl formamide (275 mL) under a nitrogen atmosphere. After the reaction mixture had stirred at ambient temperature for 2 hours, 4-chloro-1-iodobutane (19.23 g, 88.06 mmol) was added and the resulting homogeneous solution was stirred at ambient temperature for 48 hours at which time the starting material was consumed. The solution was partitioned between ethyl acetate and water. The layers were separated and the organic layer was washed with saturated aqueous sodium bicarbonate and brine, dried over anhydrous sodium sulfate, filtered and then concentrated under reduced pressure to afford a light yellow solid. The material was recrystallized from ethyl acetate and hexanes to give N,N-dibenzyl-1-(4-chlorobutyl)-1H-imidazo[4,5-c]quinolin-4-amine (20.7 g, 45.49 mmol) as white needles. MS (CI) for $C_{28}H_{27}ClN_4$ m/z 455 (MH$^+$), 365, 329, 239.

Part B

A round bottom flask was charged with a magnetic stir bar, N,N-dibenzyl-1-(4-chlorobutyl)-1H-imidazo[4,5-c]quinolin-4-amine (7.0 g, 15.38 mmol), sodium benzenethiolate (3.46 g, 26.15 mmol), and anhydrous dimethyl formamide (77 mL) under a nitrogen atmosphere. The reaction mixture was heated to 60° C. to give a heterogeneous mixture that was maintained at 60° C. for 4 hours at which time the starting material was completely consumed. The cooled solution was partitioned between ethyl acetate and water. The layers were separated. The organic layer was washed with saturated aqueous sodium bicarbonate and brine, dried over anhydrous sodium sulfate, filtered and then concentrated under reduced pressure to afford a colorless oil. The material was purified by chromatography over silica gel (80/20 hexanes/ethyl acetate) to provide N,N-dibenzyl-1-[4-(phenylthio)butyl]-1H-imidazo[4,5-c]quinolin-4-amine (7.5 g, 14.19 mmol) as a colorless oil. MS (CI) for $C_{34}H_{32}N_4S$ m/z 529 (MH$^+$), 439, 349.

Part C

A round bottom flask was charged with a magnetic stir bar, N,N-dibenzyl-1-[4-(phenylthio)butyl]-1H-imidazo[4,5-c]quinolin-4-amine (3.64 g, 6.88 mmol) and chloroform (34 mL). Solid 3-chloroperbenzoic acid (3.39 g, 15.14 mmol) was added portion wise to the resulting solution over 5 minutes. The reaction was judged to be complete after stirring at ambient temperature for 5 minutes. The solution was partitioned between chloroform and 1% aqueous sodium carbonate. The layers were separated. The organic layer was washed with brine, dried over anhydrous sodium sulfate, filtered and then concentrated under reduced pressure to afford a red gum. The material was purified by chromatography over silica gel (dichloromethane) to provide N,N-dibenzyl-1-[4-(phenylsulfonyl)butyl]-1H-imidazo[4,5-c]quinolin-4-amine (2.85 g, 5.08 mmol) as a light pink gum. MS (CI) for $C_{34}H_{32}N_4O_2S$ m/z 561 (MH$^+$), 471, 381.

Part D

A round bottom flask was charged with a magnetic stir bar, N,N-dibenzyl-1-[4-(phenylsulfonyl)butyl]-1H-imidazo[4,5-c]quinolin-4-amine (1.0 g, 1.78 mmol), triflic acid (2.68 g, 17.83 mmol), and anhydrous dichloromethane (14 mL) under a nitrogen atmosphere. The reaction was judged to be complete after stirring at ambient temperature for 24 hours. The solution was partitioned between chloroform and excess aqueous sodium hydroxide (20%). The layers were separated. The aqueous layer was extracted with chloroform (3×). The organic layers were combined and then concentrated under reduced pressure to afford a light brown solid. The material was purified by chromatography over silica gel (90/10 dichloromethane/methanol) to provide a fine white powder which was recrystallized from acetonitrile to give 1-[4-(phenylsulfonyl)butyl]-1H-imidazo[4,5-c]quinolin-4-amine (0.32 g, 0.84 mmol) as white needles, m. p. 175–177° C.

Analysis. Calculated for $C_{20}H_{20}N_4O_2S$: % C 63.14; % H, 5.30; % N, 14.73. Found: % C 63.14; % H, 5.24; % N, 14.77 $^1$H-NMR (300 MHz, DMSO) δ 8.15 (s, 1H), δ 8.01 (d, J=8.3 Hz, 1H), δ 7.80 (m, 2H), δ 7.71 (m, 1H), δ 7.60 (m, 3H), δ 7.44 (t, J=8.3 Hz, 1H), δ 7.24 (t, J=8.3 Hz, 1H), δ 6.59 (bs, 2H), δ 4.59 (t, J=6.8 Hz, 2H), δ 3.38 (t, J=7.8 Hz, 2H), δ 1.93 (m, 2H), δ 1.58 (m, 2H) MS (CI) for $C_{20}H_{20}N_4O_2S$ m/z 381 (MH$^+$), 239.

EXAMPLE 8

1-[4-(methylsulfonyl)butyl]-1H-imidazo[4,5-c]
quinolin-4-amine

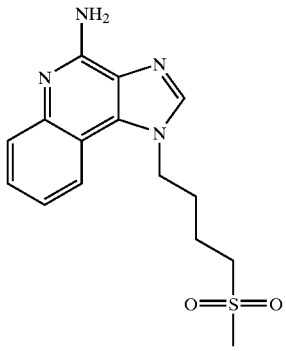

Part A

Using the general method of Example 7 Part B, N,N-dibenzyl-1-(4-chlorobutyl)-1H-imidazo[4,5-c]quinolin-4-amine (5.0 g, 10.99 mmol) was converted to N,N-dibenzyl-1-[4-(methylthio)butyl]-1H-imidazo[4,5-c]quinolin-4-amine using sodium thiomethoxide (1.16 g, 16.48 mmol). The material was purified by chromatography over silica gel (80/20 hexanes/ethyl acetate) to provide the product (4.91 g, 10.52 mmol) as a colorless oil. MS (CI) for $C_{29}H_{30}N_4S$ m/z 467 (MH$^+$), 377, 287, 185.

Part B

Using the general method of Example 7 Part C, N,N-dibenzyl-1-[4-(methylthio)butyl]-1H-imidazo[4,5-c]quinolin-4-amine (4.91 g, 15.52 mmol) was oxidized to N,N-dibenzyl-1-[4-(methylsulfonyl)butyl]-1H-imidazo[4,5-c]quinolin-4-amine which was purified by chromatography over silica gel (80/20 hexanes/ethyl acetate) to provide the product (4.53 g, 9.08 mmol) as a light orange solid. MS (CI) for $C_{29}H_{30}N_4O_2S$ m/z 499 (MH+), 409, 319.

Part C

Using the general method of Example 7 Part D, N,N-dibenzyl-1-[4-(methylsulfonyl)butyl]-1H-imidazo[4,5-c]quinolin-4-amine (4.53 g, 9.08 mmol) was converted to 1-[4-(methylsulfonyl)butyl]-1H-imidazo[4,5-c]quinolin-4-amine. The material was recrystallized from methanol and water to afford the title compound (1.33 g, 4.18 mmol) as white needles, m.p. 203–204° C.

Analysis. Calculated for $C_{15}H_{18}N_4O_2S$: % C 56.58; % H, 5.70; % N, 17.60. Found: % C 56.33; % H, 5.63; % N, 17.41 $^1$H-NMR (300 MHz, DMSO) δ 8.22 (s, 1H), δ 8.06 (d, J=8.3 Hz, 1H), δ 7.62 (d, J=8.3 Hz, 1H), δ 7.45 (t, J=8.3 Hz, 1H), δ 7.27 (t, J=8.3 Hz, 1H), δ 6.59 (bs, 2H), δ 4.65 (t, J=6.8 Hz, 2H), δ 3.19 (t, J=7.8 Hz, 2H), δ 2.93 (s, 3H), δ 1.99 (m, 2H), δ 1.74 (m, 2H) MS (CI) for $C_{15}H_{18}N_4O_2S$ m/z 319 (MH+), 239.

EXAMPLE 9

1-[4-(phenylthio)butyl]-1H-imidazo[4,5-c]quinolin-4-amine

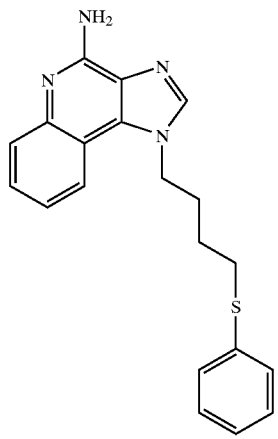

Part A

Using the general method of Example 1 Part D, N-(4-{[tert-butyl(dimethyl)silyl]oxy}butyl)quinoline-3,4-diamine (101.21 g, 292.90 mmol) was cyclized to 1-(4-{[tert-butyl(dimethyl)silyl]oxy}butyl)-1H-imidazo[4,5-c]quinoline using triethyl orthoformate (65.11 g, 439.35 mmol). The product (75.0 g, 210.93 mmol) was isolated as a brown oil and used without further purification.

Part B

Using the general method of Example 1 Part E, 1-(4-{[tert-butyl(dimethyl)silyl]oxy}butyl)-1H-imidazo[4,5-c]quinoline (42.2 g, 118.69 mmol) was oxidized to 1-(4-{[tert-butyl(dimethyl)silyl]oxy}butyl)-1H-imidazo[4,5-c]quinoline-5N-oxide (44.10 g, 118.69 mmol) which was isolated without further purification as a tan solid.

Part C

Using the general method of Example 3 Part B, 1-(4-{[tert-butyl(dimethyl)silyl]oxy}butyl)-1H-imidazo[4,5-c]quinoline-5N-oxide (44.10 g, 118.69 mmol) was aminated to provide 1-(4-{[tert-butyl(dimethyl)silyl]oxy}butyl)-1H-imidazo[4,5-c]quinolin-4-amine. The material was triturated with ethyl ether and collected by filtration to afford the product (21.54 g, 58.12 mmol) as a light brown solid which was used without further purification.

Part D

Using the general method of Example 3 Part C, 1-(4-{[tert-butyl(dimethyl)silyl]oxy}butyl)-1H-imidazo[4,5-c]quinolin-4-amine (21.5 g, 58.02 mmol) was converted to 4-(4-amino-1H-imidazo[4,5-c]quinolin-1-yl)butan-1-ol. The material was triturated with cold methanol (0° C.) and collected by filtration to afford the product (13.92 g, 54.30 mmol) which was used without further purification. MS (CI) for $C_{14}H_{16}N_4O$ m/z 257 (MH+), 185

Part E

Using the general method of Example 6 Part A, 4-(4-amino-1H-imidazo[4,5-c]quinolin-1-yl)butan-1-ol (5.0 g, 19.51 mmol) was chlorinated to provide 1-(4-chlorobutyl)-1H-imidazo[4,5-c]quinolin-4-amine (4.92 g, 17.91 mmol) which was isolated without further purification as an off-white solid.

Part F

Using the general method of Example 6 Part B, except that the reaction temperature was lowered to 80° C., 1-(4-chlorobutyl)-1H-imidazo[4,5-c]quinolin-4-amine (1.5 g, 5.46 mmol) was converted to 1-[4-(phenylthio)butyl]-1H-imidazo[4,5-c]quinolin-4-amine. The resulting solid (1.53 g) was dissolved in acetonitrile (90 mL) and brought to reflux. Activated charcoal (0.9 g) was added and the resulting mixture was heated at reflux for 5 minutes and then the charcoal was removed by filtration through fluted paper to provide a colorless solution. The title compound (0.86 g, 2.47 mmol) was isolated as white needles, m.p 158–160° C.

Analysis. Calculated for $C_{20}H_{20}N_4S$: % C 68.94; % H, 5.79; % N, 16.08. Found: % C 68.70; % H, 5.74; % N, 16.08 $^1$H-NMR (300 MHz, DMSO) δ 8.18 (s, 1H), δ 8.05 (d, J=8.3 Hz, 1H), δ 7.63 (d, J=8.3 Hz, 1H), δ 7.45 (t, J=8.3 Hz, 1H), δ 7.26 (m, 5H), δ 7.14–7.19 (m, 1H), δ 6.60 (bs, 2H), δ 4.62 (t, J=6.8 Hz, 2H), δ 3.00 (t, J=7.3 Hz, 2H), δ 2.00 (m, 2H), δ 1.61 (m, 2H) MS (CI) for $C_{20}H_{20}N_4S$ m/z 349 (MH+), 185.

EXAMPLE 10

1-[4-(methylthio)butyl]-1H-imidazo[4,5-c]quinolin-4-amine

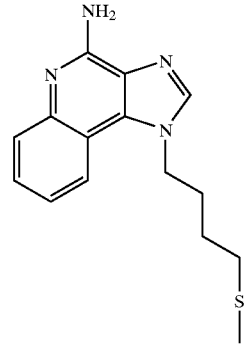

Part A

Using the general method of Example 6 Part B, except that the reaction temperature was lowered to 80° C., 1-(4-chlorobutyl)-1H-imidazo[4,5-c]quinolin-4-amine (1.5 g, 5.46 mmol) was converted to 1-[4-(methylthio)butyl]-1H-imidazo[4,5-c]quinolin-4-amine using sodium thiomethoxide (0.88 g, 12.56 mmol) in lieu of sodium benzenethiolate.

The resulting solid (1.26 g) was dissolved in acetonitrile (40 mL) and brought to reflux. Activated charcoal (0.7 g) was added, the resulting mixture was heated at reflux for 5 minutes and then the charcoal was removed by filtration through fluted paper to provide a colorless solution. The solution was concentrated under reduced pressure to give a solid that was recrystallized from acetonitrile. The title compound (0.66 g, 2.30 mmol) was isolated as white needles, m.p 163–164° C.

Analysis. Calculated for $C_{15}H_{18}N_4S$: % C 62.91; % H, 6.34; % N, 19.56. Found: % C 62.70; % H, 6.19; % N, 19.45 $^1$H-NMR (300 MHz, DMSO) δ 8.21 (s, 1H), δ 8.06 (d, J=8.3 Hz, 1H), δ 7.62 (d, J=8.3 Hz, 1H), δ 7.44 (t, J=8.3 Hz, 1H), δ 7.26 (t, J=8.3 Hz, 1H), δ 6.59 (bs, 2H), δ 4.62 (t, J=7.6 Hz, 2H), δ 2.50 (t, J=6.8 Hz, 2H), δ 1.99 (s, 3H), δ 1.95 (p, J=7.3 Hz, 2H), δ 1.59 (p, J=7.3 Hz, 2H) MS (CI) for $C_{15}H_{18}N_4S$ m/z 287 (MH$^+$), 185.

EXAMPLE 11

2-butyl-1-[5-(methylsulfonyl)pentyl]-1H-imidazo[4,5-c]quinolin-4-amine

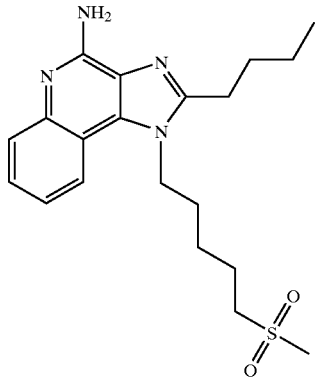

Part A

Using the general method of Example 1 Part A, 4-chloro-3-nitroquinoline (107.7 g, 525.87 mmol) was converted to 5-[(3-nitroquinolin-4-yl)amino]pentan-1-ol using 5-amino-1-pentanol (79.82 g, 788.81 mmol) in lieu of 4-aminobutanol. The product (117.22 g, 425.77 mmol) was used without further purification as a dark yellow solid. MS (CI) for $C_{14}H_{17}N_3O_3$ m/z 276 (MH$^+$), 224.

Part B

A round bottom flask was charged with a magnetic stir bar, 5-[(3-nitroquinolin-4-yl)amino]pentan-1-ol (5.0 g, 18.16 mmol), and thionyl chloride (40.78 g, 0.34 mmol) under a nitrogen atmosphere. The reaction mixture was heated to 80° C. to give a homogeneous solution that was maintained at 80° C. for 1 hour at which time the starting material was completely consumed. The volatiles were removed under reduced pressure and the resulting oil stirred in water made basic (pH 10) with solid sodium carbonate. The resulting solid was collected by filtration to afford N-(5-chloropentyl)-3-nitroquinolin-4-amine (4.80 g, 16.34 mmol) which was used without further purification.

Part C

Using the general method of Example 6 Part B, except that the reaction temperature was lowered to 80° C., N-(5-chloropentyl)-3-nitroquinolin-4-amine (4.75 g, 16.17 mmol) was converted to N-[5-(methylthio)pentyl]-3-nitroquinolin-4-amine using sodium thiomethoxide (1.43 g, 19.40 mmol) in lieu of sodium benzenethiolate. The product (3.28 g, 10.74 mmol) was isolated without further purification as a light yellow solid. MS (CI) for $C_{15}H_{19}N_3O_2S$ m/z 306 (MH$^+$), 272, 117.

Part D

Using the general method of Example 1 Part C, N-[5-(methylthio)pentyl]-3-nitroquinolin-4-amine (3.20 g, 10.48 mmol) was reduced to $N^4$-[5-(methylthio)pentyl]quinoline-3,4-diamine (2.89 g, 10.48 mmol) which was isolated without further purification as a brown oil.

Part E

Using the general method of Example 1 Part D, N'-[5-(methylthio)pentyl]quinoline-3,4-diamine (2.89 g, 10.48 mmol) was cyclized to provide 2-butyl-1-[5-(methylthio)pentyl]-1H-imidazo[4,5-c]quinoline. The material was purified by chromatography over silica gel (ethyl acetate) to afford the product (2.10 g, 6.15 mmol) as a light brown oil.

Part F

A round bottom flask was charged with a magnetic stir bar, 2-butyl-1-[5-(methylthio)pentyl]-1H-imidazo[4,5-c]quinoline (2.1 g, 6.15 mmol) and chloroform (31 mL). Solid 3-chloroperbenzoic acid (4.41 g, 19.68 mmol) was added portion wise to the solution over 10 minutes and the reaction was stirred at ambient temperature for 30 minutes at which time the starting material was completely consumed. The solution was partitioned between chloroform and saturated aqueous sodium bicarbonate. The layers were separated. The organic layer was washed with saturated aqueous sodium bicarbonate and brine, dried over anhydrous sodium sulfate, filtered and then concentrated under reduced pressure to afford 2-butyl-1-[5-(methylsulfonyl)pentyl]-1H-imidazo[4,5-c]quinoline-5N-oxide (2.40 g, 6.15 mmol) as a tan solid. The material was used without further purification.

Part G

Using the general method of Example 3 Part B, 2-butyl-1-[5-(methylsulfonyl)pentyl]-1H-imidazo[4,5-c]quinoline-5N-oxide (2.40 g, 6.15 mmol) was aminated to provide 2-butyl-1-[5-(methylsulfonyl)pentyl]-1H-imidazo[4,5-c]quinolin-4-amine. The resulting solid (2.24 g) was dissolved in acetonitrile (40 mL) and brought to reflux. Activated charcoal (1 g) was added and the resulting mixture was heated at reflux for 5 minutes and then the charcoal was removed by filtration through fluted paper to provide a light brown solution. Upon cooling 2-butyl-1-[5-(methylsulfonyl)pentyl]-1H-imidazo[4,5-c]quinolin-4-amine (0.90 g, 2.32 mmol) was isolated as white needles, m.p. 173–175° C.

Analysis. Calculated for $C_{20}H_{28}N_4O_2S$: % C 61.83; % H, 7.26; % N, 14.42. Found: % C 61.58; % H, 7.27; % N, 14.36 $^1$H-NMR (300 MHz, DMSO) δ 8.01 (d, J=8.3 Hz, 1H), δ 7.61 (d, J=8.3 Hz, 1H), δ 7.41 (t, J=8.3 Hz, 1H), δ 7.26 (t, J=8.3 Hz, 1H), δ 6.45 (bs, 2H), δ 4.51 (t, J=7.6 Hz, 2H), δ 3.10 (t, J=7.8 Hz, 2H), δ 2.92 (s, 3H), δ 2.92 (t, J=7.3 Hz, 2H), δ 1.76 (m, 6H), δ 1.54 (m, 2H), δ 1.46 (sextet, J=7.3 Hz, 2H), δ 0.99 (t, J=7.3 Hz, 3H) MS (CI) for $C_{20}H_{28}N_4O_2S$ m/z 389 (MH$^+$).

EXAMPLE 12

2-methyl-1-[5-(methylsulfonyl)pentyl]-1H-imidazo[4,5-c]quinolin-4-amine

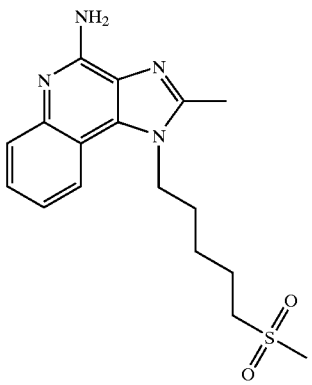

Part A

Using the general method of Example 1 Part D, N$^4$-[5-(methylthio)pentyl]quinoline-3,4-diamine (4.53 g, 16.37 mmol) was cyclized to provide 2-methyl-1-[5-(methylthio)pentyl]-1H-imidazo[4,5-c]quinoline using 1,1,1-trimethoxyethane (2.95 g, 24.6 mmol) and pyridine hydrochloride (0.1 g). The material was triturated with ethyl ether and collected by filtration to afford the product (3.78 g, 12.62 mmol) as a light brown solid which was used without further purification.

Part B

Using the general method of Example 11 Part F, 2-methyl-1-[5-(methylthio)pentyl]-1H-imidazo[4,5-c]quinoline (3.78 g, 12.62 mmol) was oxidized to 2-methyl-1-[5-(methylsulfonyl)pentyl]-1H-imidazo[4,5-c]quinoline-5N-oxide (4.38 g, 12.62 mmol) which was isolated as a tan solid and used without purification.

Part C

Using the general method of Example 3 Part B, 2-methyl-1-[5-(methylsulfonyl)pentyl]-1H-imidazo[4,5-c]quinoline-5N-oxide (4.38 g, 12.62 mmol) was aminated to provide 2-methyl-1-[5-(methylsulfonyl)pentyl]-1H-imidazo[4,5-c]quinolin-4-amine. The resulting solid was triturated with acetonitrile and collected by filtration to afford the title compound (0.8 g, 2.31 mmol) as an off-white solid, m.p. 235–240° C.

Analysis. Calculated for $C_{17}H_{22}N_4O_2S$: % C 58.94; % H, 6.40; % N, 16.17. Found: % C 58.77; % H, 6.34; % N, 16.39 $^1$H-NMR (300 MHz, DMSO) δ 8.02 (d, J=8.3 Hz, 1H), δ 7.60 (d, J=8.3 Hz, 1H), δ 7.41 (t, J=8.3 Hz, 1H), δ 7.25 (t, J=8.3 Hz, 1H), δ 6.49 (bs, 2H), δ 4.50 (t, J=7.3 Hz, 2H), δ 3.12 (t, J=7.8 Hz, 2H), δ 2.92 (s, 3H), δ 2.61 (s, 3H), δ 1.86 (m, 2H), δ 1.74 (m, 2H), δ 1.53 (m, 2H) MS (CI) for $C_{17}H_{22}N_4O_2S$ m/z 347 (MH$^+$), 267.

EXAMPLE 13

2-ethyl-1-[5-(methylsulfonyl)pentyl]-1H-imidazo[4,5-c]quinolin-4-amine

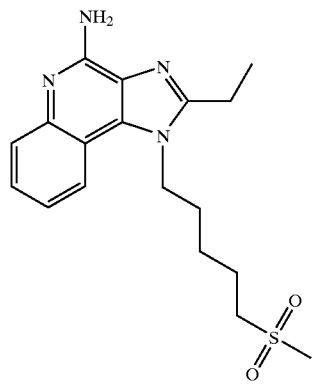

Part A

Using the general method of Example 1 Part D, N4-[5-(methylthio)pentyl]quinoline-3,4-diamine (4.53 g, 16.37 mmol) was cyclized to 2-ethyl-1-[5-(methylthio)pentyl]-1H-imidazo[4,5-c]quinoline using triethyl orthopropionate (4.3 g, 24.56 mmol) and pyridine hydrochloride (0.1 g). The material was triturated with ethyl ether and collected by filtration to afford the product (3.25 g, 10.37 mmol) as an off-white powder which was used without further purification.

Part B

Using the general method of Example 11 Part F, 2-ethyl-1-[5-(methylthio)pentyl]-1H-imidazo[4,5-c]quinoline (3.25 g, 10.37 mmol) was oxidized to 2-ethyl-1-[5-(methylsulfonyl)pentyl]-1H-imidazo[4,5-c]quinoline-5N-oxide (3.75 g, 10.37 mmol); which was isolated as a tan solid and used without purification.

Part C

Using the general method of Example 3 Part B, 2-ethyl-1-[5-(methylsulfonyl)pentyl]-1H-imidazo[4,5-c]quinoline-5N-oxide (3.75 g, 10.37 mmol) was aminated to provide 2-ethyl-1-[5-(methylsulfonyl)pentyl]-1H-imidazo[4,5-c]quinolin-4-amine. The resulting solid was recrystallized sequentially from ethanol and acetonitrile to afford the title compound (1.4 g, 3.88 mmol) as off-white needles, m.p. 189–191° C.

Analysis: Calculated for $C_{18}H_{24}N_4O_2S$: % C 59.98; % H, 6.71; % N, 15.54. Found: % C 59.71; % H, 6.68; % N, 15.64 $^1$H-NMR (300 MHz, DMSO) δ 8.01 (d, J=8.3 Hz, 1H), δ 7.61 (d, J=8.3 Hz, 1H), δ 7.42 (t, J=8.3 Hz, 1H), δ 7.26 (t, J=8.3 Hz, 1H), δ 6.45 (bs, 2H), δ 4.50 (t, J=7.6 Hz, 2H), δ 3.10 (t, J=7.8 Hz, 2H), δ 2.95 (q, J=7.3 Hz, 2H), δ 2.92 (s, 3H), δ 1.85 (m, 2H), δ1.74 (m, 2H), δ 1.55 (m, 2H), δ 1.38 (t, J=7.3 Hz, 3H) MS (CI) for $C_{18}H_{24}N_4O_2S$ m/z 361 (MH$^+$), 281.

EXAMPLE 14

1-[5-(methylsulfonyl)pentyl]-1H-imidazo[4,5-c]quinolin-4-amine

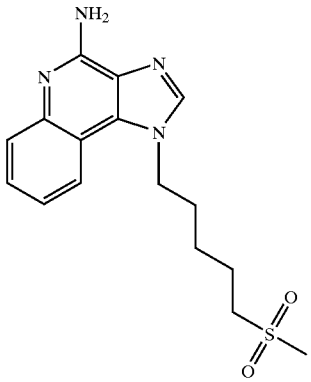

Part A

Using the general method of Example 1 Part D, $N^4$-[5-(methylthio)pentyl]quinoline-3,4-diamine (4.53 g, 16.37 mmol) was cyclized to 1-[5-(methylthio)pentyl]-1H-imidazo[4,5-c]quinoline using triethyl orthoformate (3.64 g, 24.56 mmol) and pyridine hydrochloride (0.1 g). The product (4.05 g, 14.19 mmol) was isolated as a brown oil and used without further purification.

Part B

Using the general method of Example 11 Part F, 1-[5-(methylthio)pentyl]-1H-imidazo[4,5-c]quinoline (4.05 g, 14.19 mmol) was oxidized to 1-[5-(methylsulfonyl)pentyl]-1H-imidazo[4,5-c]quinoline-5N-oxide (4.73 g, 14.19 mmol) which was isolated as a tan solid and used without further purification.

Part C

Using the general method of Example 3 Part B, 1-[5-(methylsulfonyl)pentyl]-1H-imidazo[4,5-c]quinoline-5N-oxide (4.73 g, 14.19 mmol) was aminated to provide 1-[5-(methylsulfonyl)pentyl]-1H-imidazo[4,5-c]quinolin-4-amine. The material was purified by chromatography over silica gel (95/5 dichloromethane/methanol) to afford a light yellow solid. The solid was recrystallized from dimethyl formamide to give the title compound (0.43 g, 1.29 mmol) as a light yellow, granular solid, m.p. 199–201° C.

Analysis. Calculated for $C_{16}H_{20}N_4O_2S$: % C 57.70; % H, 6.06; % N, 16.85. Found: % C 57.01; % H, 6.06; % N, 16.70 $^1$H-NMR (300 MHz, DMSO) δ 8.20 (S, 1H), δ 8.04 (d, J=8.3 Hz, 1H), δ 7.62 (d, J=8.3 Hz, 1H), δ 7.44 (t, J=8.3 Hz, 1H), δ 7.27 (t, J=8.3 Hz, 1H), δ 6.57 (bs, 2H), δ 4.61 (t, J=6.8 Hz, 2H), δ 3.09 (t, J=7.8 Hz, 2H), δ 2.92 (s, 3H), δ 1.91 (p, J=7.6 Hz, 2H), δ 1.73 (m, 2H), δ 1.45 (m, 2H) MS (CI) for $C_{16}H_{20}N_4O_2S$ m/z 333 (MH$^+$).

EXAMPLE 15

2-hexyl-1-[5-(methylsulfonyl)pentyl]-1H-imidazo[4,5-c]quinolin-4-amine

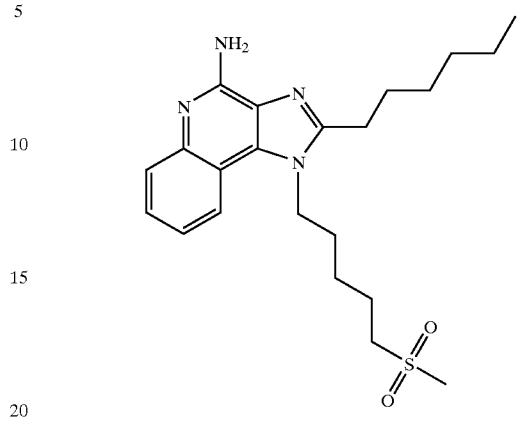

Part A

A round bottom flask was charged with a magnetic stir bar, $N^4$-[5-(methylthio)pentyl]quinoline-3,4-diamine (3.17 g, 11.46 mmol) and anhydrous pyridine (46 mL) under a nitrogen atmosphere. The resulting homogeneous solution was cooled to 0° C. in an ice-water bath. To the cooled solution was added neat heptanoyl chloride (1.87 g, 12.61 mmol). The reaction was judged to be complete after stirring at ambient temperature for 1 hour. The volatiles were removed under reduced pressure and the resulting oil was partitioned between chloroform and water. The layers were separated. The organic layer was washed with saturated aqueous sodium bicarbonate and brine, dried over anhydrous sodium sulfate, filtered and then concentrated under reduced pressure to afford N-(4-{[5-(methylthio)pentyl]amino}quinolin-3-yl)heptanamide (4.44 g, 11.46 mmol) which was isolated as a brown oil and used without further purification.

Part B

A round bottom flask was charged with a magnetic stir bar, N-(4-{[5-(methylthio)pentyl]amino}quinolin-3-yl)heptanamide (4.44 g, 11.46 mmol), pyridine hydrochloride (0.13 g, 1.15 mmol), and anhydrous pyridine (50 mL) under a nitrogen atmosphere. The reaction was judged to be complete after stirring at reflux for 1.5 hours. The solution was cooled and partitioned between ethyl acetate and water. The layers were separated. The organic layer was washed with saturated aqueous sodium bicarbonate and brine, dried over anhydrous sodium sulfate, filtered and then concentrated under reduced pressure to afford 2-hexyl-1-[5-(methylthio)pentyl]-1H-imidazo[4,5-c]quinoline (4.0 g, 10.82 mmol) as a brown oil which was used without further purification.

Part C

Using the general method of Example 11 Part F, 2-hexyl-1-[5-(methylthio)pentyl]-1H-imidazo[4,5-c]quinoline (4.0 g, 10.82 mmol) was oxidized to 2-hexyl-1-[5-(methylsulfonyl)pentyl]-1H-imidazo[4,5-c]quinoline-5N-oxide (4.52 g, 10.82 mmol) which was isolated as a tan solid and used without further purification.

Part D

Using the general method of Example 3 Part B 2-hexyl-1-[5-(methylsulfonyl)pentyl]-1H-imidazo[4,5-c]quinoline-5N-oxide (4.0 g, 10.82 mmol) was aminated to provide 2-hexyl-1-[5-(methylsulfonyl)pentyl]-1H-imidazo[4,5-c]quinolin-4-amine. The material was recrystallized from acetonitrile to afford the title compound (2.25 g, 5.40 mmol) as off-white needles, m.p. 168–171° C.

Analysis. Calculated for $C_{22}H_{32}N_4O_2S$: % C 63.43; % H, 7.74; % N, 13.45. Found: % C 63.06; % H, 7.66; % N, 13.81 $^1$H-NMR (300 MHz, DMSO) δ 8.01 (d, J=8.3 Hz, 1H), δ 7.62 (d, J=8.3 Hz, 1H), δ 7.42 (t, J=8.3 Hz, 1H), δ 7.26 (t, J=8.3 Hz, 1H), δ 6.51 (bs, 2H), δ 4.51 (t, J=7.3 Hz, 2H), δ 3.10 (t, J=7.8 Hz, 2H), δ 2.93 (s, 3H), δ 2.93 (t, J=7.3 Hz, 2H), δ 1.71–1.87 (m, 6H), δ 1.54 (m, 2H), δ 1.44 (m, 2H), δ 1.33 (m, 4H), δ 0.89 (t, J=7.3 Hz, 3H) MS (CI) for $C_{22}H_{32}N_4O_2S$ m/z 417 (M$^+$), 337.

EXAMPLE 16

2-(2-methoxyethyl)-1-[5-(methylsulfonyl)pentyl]-1H-imidazo[4,5-c]quinolin-4-amine

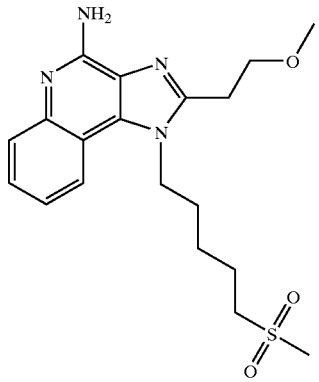

Part A

A round bottom flask was charged with a magnetic stir bar, $N^4$-[5-(methylthio)pentyl]quinoline-3,4-diamine (3.56 g, 12.93 mmol) and anhydrous pyridine (52 mL) under a nitrogen atmosphere. The resulting homogeneous solution was cooled to 0° C. in an ice-water bath. To the cooled solution was added neat 3-methoxypropionyl chloride (2.74 g, 22.36 mmol). After addition of the acid chloride, the reaction was heated to reflux for 14 hours at which time the acylated intermediate was completely consumed. The solution was cooled and then partitioned between chloroform and saturated aqueous ammonium chloride. The layers were separated. The organic layer was washed with saturated aqueous sodium bicarbonate, dried over anhydrous sodium sulfate, filtered and then concentrated under reduced pressure to afford 2-(2-methoxyethyl)-1-[5-(methylthio)pentyl]-1H-imidazo[4,5-c]quinoline (3.0 g, 8.73 mmol) which was isolated as a brown oil and used without further purification.

Part B

Using the general method of Example 11 Part F, 2-(2-methoxyethyl)-1-[5-(methylthio)pentyl]-1H-imidazo[4,5-c]quinoline (3.0 g, 8.73 mmol) was oxidized to 2-(2-methoxyethyl)-1-[5-(methylsulfonyl)pentyl]-1H-imidazo[4,5-c]quinoline-5N-oxide (3.41 g, 8.73 mmol) which was isolated as a tan solid and used without further purification.

Part C

Using the general method of Example 3 Part B, 2-(2-methoxyethyl)-1-[5-(methylsulfonyl)pentyl]-1H-imidazo[4,5-c]quinoline-5N-oxide (3.41 g, 8.73 mmol) was aminated to provide 2-(2-methoxyethyl)-1-[5-(methylsulfonyl)pentyl]-1H-imidazo[4,5-c]quinolin-4-amine. The resulting solid was purified by chromatography over silica gel (95/5 dichloromethane/methanol) to provide a gummy solid. The solid was recrystallized from acetonitrile to give the title compound (0.54 g, 1.38 mmol) as an off-white powder, m.p. 158–160° C.

Analysis. Calculated for $C_{19}H_{26}N_4O_3S$: % C 58.44; % H, 6.71; % N, 14.35. Found: % C 58.24; % H, 6.76; % N, 14.70 $^1$H-NMR (300 MHz, DMSO) δ 8.02 (d, J=8.3 Hz, 1H), δ 7.62 (d, J=8.3 Hz, 1H), δ 7.42 (t, J=8.3 Hz, 1H), δ 7.26 (t, J=8.3 Hz, 1H), δ 6.50 (bs, 2H), δ 4.53 (t, J=7.6 Hz, 2H), δ 3.83 (t, J=6.8 Hz, 2H), δ 3.30 (s, 3H), δ 3.19 (t, J6.8Hz, 2H), δ 3.11 (t, J=7.8 Hz, 2H), δ 2.93 (s, 3H), δ 1.85 (m, 2H), δ 1.76 (m, 2H), δ 1.57 (m, 2H) MS (CI) for $C_{19}H_{26}N_4O_3S$ m/z 391 (MH$^+$), 359.

EXAMPLE 17

2-butyl-1-[5-(methylthio)pentyl]-1H-imidazo[4,5-c]quinolin-4-amine

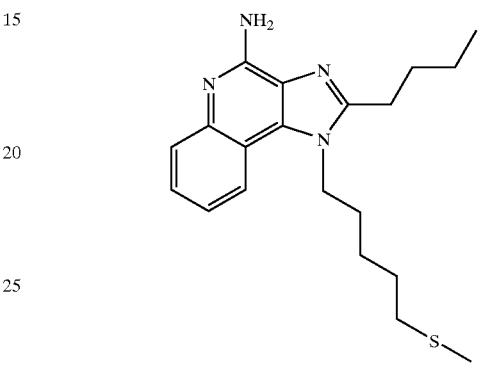

Part A

Using the general method of Example 1 Part C, N-(5-chloropentyl)-3-nitroquinolin-4-amine (2.0 g, 6.80 mmol) was reduced to provide N-(5-chloropentyl)quinoline-3,4-diamine (1.79 g, 6.80 mmol) which was isolated as a brown oil and used without further purification.

Part B

Using the general method of Example I Part D, $N^4$-(5-chloropentyl)quinoline-3,4-diamine (1.79 g, 6.80 mmol) was cyclized to 2-butyl-1-(5-chloropentyl)-1H-imidazo[4,5-c]quinoline using trimethyl orthovalerate (2.55 g, 15.72 mmol) and pyridine hydrochloride (0.079 g). The product (1.95 g, 5.91 mmol) was isolated as an off-white solid and used without further purification.

Part C

Using the general method of Example 1 Part E, 2-butyl-1-(5-chloropentyl)-1H-imidazo[4,5-c]quinoline (1.95 g, 5.91 mmol) was oxidized to 2-butyl-1-(5-chloropentyl)-1H-imidazo[4,5-c]quinoline-5N-oxide (2.04 g, 5.91 mmol) which was isolated as a tan solid and used without further purification.

Part D

Using the general method of Example 3 Part B, 2-butyl-1-(5-chloropentyl)-1H-imidazo[4,5-c]quinoline-5N-oxide (2.04 g, 5.91 mmol) was aminated to provide 2-butyl-1-(5-chloropentyl)-1H-imidazo[4,5-c]quinolin-4-amine. The resulting solid was recrystallized from ethanol to afford the product (0.85 g, 2.46 mmol) as a fine white powder, m.p. 144–146° C.

Analysis. Calculated for $C_{19}H_{25}ClN_4$: % C 66.17; % H, 7.31; % N, 16.24. Found: % C 66.44; % H, 7.55; % N, 16.29 MS (CI) for $C_{19}H_{25}ClN_4$ m/z 345 (MH$^+$), 309.

Part E

Using the general method of Example 6 Part B, except that the reaction temperature was lowered to 80° C., 2-butyl-1-(5-chloropentyl)-1H-imidazo[4,5-c]quinolin-4-amine (2.0 g, 5.80 mmol) was converted to 2-butyl-1-[5-(methylthio)pentyl]-1H-imidazo[4,5-c]quinolin-4-amine using sodium thiomethoxide (0.68 g, 8.70 mmol) in lieu of sodium benzenethiolate. The resulting solid was partitioned between chloroform and saturated aqueous sodium bicarbonate. The layers were separated. The organic layer was washed with brine, dried over anhydrous sodium sulfate, filtered and then concentrated under reduced pressure to afford a white solid. The material was recrystallized from acetonitrile to give the title compound (1.91 g, 5.36 mmol) as a fine white solid, m.p. 112–114° C.

Analysis. Calculated for $C_{20}H_{28}N_4S$: % C 67.38; % H, 7.92; % N, 15.71. Found: % C 67.26; % H, 8.08; % N, 15.74 $^1$H-NMR (300 MHz, DMSO) δ 8.01 (d, J=8.3 Hz, 1H), δ 7.61 (d, J=8.3 Hz, 1H), δ 7.41 (t, J=8.3 Hz, 1H), δ 7.25 (t, J=8.3 Hz, 1H), δ 6.45 (bs, 2H), δ 4.50 (t, J=7.8 Hz, 2H), δ 2.92 (t, J=7.6 Hz, 2H), δ 2.46 (t, J=7.3 Hz, 2H), δ 2.01 (s, 3H), δ 1.80 (m, 4H), δ 1.42–1.61 (m, 6H), δ 0.96 (t, J=7.3 Hz, 3H) MS (CI) for $C_{20}H_{28}N_4S$ m/z 357 (MH$^+$), 309.

EXAMPLE 18

2-butyl-1-[5-(methylsulfinyl)pentyl]-1H-imidazo[4,5-c]quinolin-4-amine

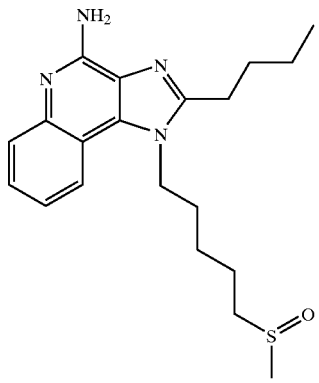

A round bottom flask was charged with a magnetic stir bar, 2-butyl-1-[5-(methylthio)pentyl]-1H-imidazo[4,5-c]quinolin-4-amine (1.0 g, 2.80 mmol) and chloroform (14 mL). Solid 3-chloroperbenzoic acid (0.69 g, 3.09 mmol) was added portion wise over 5 minutes and the reaction was stirred at ambient temperature for 20 minutes at which time the starting material was completely consumed. The solution was partitioned between chloroform and saturated aqueous sodium bicarbonate. The layers were separated. The organic layer was washed with saturated aqueous sodium bicarbonate and brine, dried over anhydrous sodium sulfate, filtered and then concentrated under reduced pressure to afford an off-white solid which was shown by $^1$H-NMR to be the 3-chlorobenzoic acid salt of the desired product. The solid was stirred in water and then made basic (pH 10) by addition of solid sodium carbonate. The resulting free base was collected by filtration to provide a white solid which was recrystallized from acetonitrile to give 2-butyl-1-[5-(methylsulfinyl)pentyl]-1H-imidazo[4,5-c]quinolin-4-amine (0.40 g, 1.07 mmol) as a white powder, m.p. 119–121° C.

Analysis. Calculated for $C_{20}H_{28}N_4OS$ $(H_2O)_1$: % C 61.51; % H, 7.74; % N, 14.35. Found: % C 61.64; % H, 7.82; % N, 14.32 $^1$H-NMR (300 MHz, DMSO) δ 8.01 (d, J=8.3 Hz, 1H), δ 7.60 (d, J=8.3 Hz, 1H), δ 7.41 (t, J=8.3 Hz, 1H), δ 7.26 (t, J=8.3 Hz, 1H), δ 6.44 (bs, 2H), δ 4.51 (t, J=7.6 Hz, 2H), δ 2.92 (t, J=7.8 Hz, 2H), δ 2.57–2.74 (m, 2H), δ 2.50 (s, 3H), δ 1.80 (m, 4H), 1.66 (m, 2H), δ 1.55 (m, 2H), δ 1.48 (m, 2H), δ 0.96 (t, J=7.3 Hz, 3H) MS (CI) for $C_{20}H_{28}N_4OS$ $(H_2O)_1$ m/z 373 (MH$^+$), 309, 253.

EXAMPLE 19

2-butyl-1-[3-(methylsulfonyl)propyl]-1H-imidazo[4,5-c]quinolin-4-amine

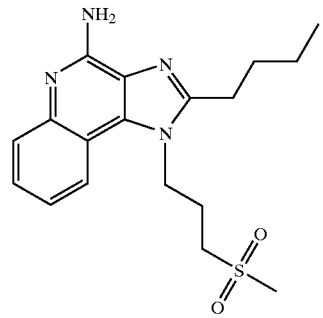

Part A

A round bottom flask was charged with a magnetic stir bar, 3-[(3-nitroquinolin-4-yl)amino]propan-1-ol (20.75 g, 83.93 mmol), thionyl chloride (15.0 g, 125.89 mmol), and dichloromethane (420 mL). The bright yellow, homogeneous solution was stirred at ambient temperature for 2 hours at which time the starting material was completely consumed. The volatiles were removed under reduced pressure and the resulting solid stirred in water (400 mL) made basic (pH 10) with solid sodium carbonate. A bright yellow solid was collected by filtration to afford N-(3-chloropropyl)-3-nitroquinolin-4-amine (21.63 g, 81.41 mmol) which was used without further purification.

Part B

Using the general method of Example 1 Part C, N-(3-chloropropyl)-3-nitroquinolin-4-amine (10.0 g, 37.63 mmol) was reduced to provide $N^4$-(3-chloropropyl)quinoline-3,4-diamine (8.87 g, 37.63 mmol) which was isolated as a brown oil and used without further purification.

Part C

Using the general method of Example 1 Part D, $N^4$-(3-chloropropyl)quinoline-3,4-diamine (8.87 g, 37.63 mmol) was cyclized to provide 2-butyl-1-(3-chloropropyl)-1H-imidazo[4,5-c]quinoline using trimethyl orthovalerate (7.33 g, 45.16 mmol) and pyridine hydrochloride (0.43 g). The resulting solid was triturated with ethyl ether and collected by filtration to afford the product (9.00 g, 29.82 mmol) as an off-white solid. The material was used without further purification.

Part D

Using the general method of Example 1 Part E, 2-butyl-1-(3-chloropropyl)-1H-imidazo[4,5-c]quinoline (9.0 g, 29.82 mmol) was oxidized to 2-butyl-1-(3-chloropropyl)-1H-imidazo[4,5-c]quinoline-5N-oxide (9.48 g, 29.82 mmol) which was isolated as a tan solid and used without purification.

Part E

Using the general method of Example 3 Part B, 2-butyl-1-(3-chloropropyl)-1H-imidazo[4,5-c]quinoline-5N-oxide (9.48 g, 29.82 mmol) was aminated to provide 2-butyl-1-(3-chloropropyl)-1H-imidazo[4,5-c]quinolin-4-amine. The resulting solid was purified by chromatography over silica gel (95/5 dichloromethane/methanol) to provide the product (6.4 g, 20.20 mmol) as a tan solid.

Part F

Using the general method of Example 6 Part B, except that the reaction temperature was lowered to 80° C., 2-butyl- 1-(3-chloropropyl)-1H-imidazo[4,5-c]quinolin-4-amine (2.0 g, 6.31 mmol) was converted to 2-butyl-1-[3-(methylthio)propyl]-1H-imidazo[4,5-c]quinolin-4-amine using sodium thiomethoxide (0.74 g, 9.47 mmol) in lieu of sodium benzenethiolate. The resulting solid was partitioned between chloroform and saturated aqueous sodium bicarbonate. The layers were separated. The organic layer was washed with brine, dried over anhydrous sodium sulfate, filtered and then concentrated under reduced pressure to afford the title compound (2.0 g, 6.09 mmol) as a white solid. The material was used without further purification.

Part G

Using the general method of Example 5 Part A, 2-butyl-1-[3-(methylthio)propyl]-1H-imidazo[4,5-c]quinolin-4-amine 2.0 g, 6.09 mmol) was oxidized to 2-butyl-1-[3-(methylsulfonyl)propyl]-1H-imidazo[4,5-c]quinolin-4-amine. The resulting solid was triturated with methanol and collected by filtration to afford the title compound (0.96 g, 2.66 mmol) as an off-white powder, m.p. 233–236° C.

Analysis. Calculated for $C_{18}H_{24}N_4O_2S$: % C 59.98; % H, 6.71; % N, 15.54. Found: % C 59.71; % H, 6.65; % N, 15.43 $^1$H-NMR (300 MHz, DMSO) δ 8.10 (d, J=8.3 Hz, 1H), δ 7.61 (d, J=8.3 Hz, 1H), δ 7.42 (t, J=8.3 Hz, 1H), δ 7.25 (t, J=8.3 Hz, 1H), δ 6.47 (bs, 2H), δ 4.66 (t, J=7.8 Hz, 2H), δ 3.40 (t, J=7.3 Hz, 2H), δ 3.01 (s, 3H), δ 2.94 (t, J=7.8 Hz, 2H), δ 2.22 (m, 2H), δ 1.80 (m, 2H), δ 1.46 (sextet, J=7.3 Hz, 2H), δ 0.96 (t, J=7.3 Hz, 3H) MS (CI) for $C_{18}H_{24}N_4O_2S$ m/z 361 (MH$^+$), 281, 235.

EXAMPLE 20

2-butyl-1-[3-(phenylsulfonyl)propyl]-1H-imidazo[4,5-c]quinolin-4-amine

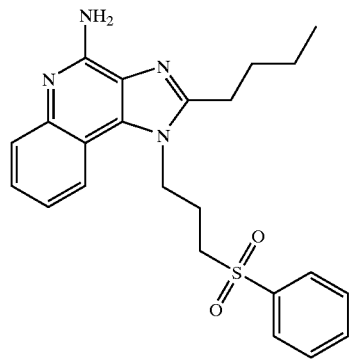

Part A

A round bottom flask was charged with a magnetic stir bar, benzenethiol (0.68 g, 6.21 mmol), sodium hydride (0.25 g, 60% dispersion, 6.21 mmol), and anhydrous dimethyl formamide (28 mL) under a nitrogen atmosphere. After the reaction mixture had stirred at ambient temperature for 30 minutes, 2-butyl-1-(3-chloropropyl)-1H-imidazo[4,5-c]quinolin-4-amine (1.64 g, 5.18 mmol) was added and the resulting cloudy solution was heated to 80° C. and maintained at 80° C. for 2.5 hours at which time the starting material was completely consumed. The hot solution was poured into rapidly stirred water (200 mL). The resulting mixture was extracted with chloroform (2×). The combined organic layers were washed with saturated aqueous sodium bicarbonate and brine, dried over anhydrous sodium sulfate, filtered and then concentrated under reduced pressure to afford a light yellow oil. The material was purified by chromatography over silica gel (95/5 dichloromethane/methanol) to provide 2-butyl-1-[3-(phenylthio)propyl]-1H-imidazo[4,5-c]quinolin-4-amine (1.38 g, 3.53 mmol) as a white solid.

Part B

Using the general method of Example 5 Part A, 2-butyl-1-[3-(phenylthio)propyl]-1H-imidazo[4,5-c]quinolin-4-amine (1.38 g, 3.53 mmol) was oxidized to 2-butyl-1-[3-(phenylsulfonyl)propyl]-1H-imidazo[4,5-c]quinolin-4-amine. The resulting solid was recrystallized from ethanol to provide the title compound (0.85 g, 2.01 mmol) as an off-white powder, m.p. 224–227° C.

Analysis. Calculated for $C_{23}H_{26}N_4O_2S$: % C 65.38; % H, 6.20; % N, 13.26. Found: % C 65.25; % H, 6.23; % N, 13.20 $^1$H-NMR (300 MHz, DMSO) δ 7.96 (d, J=8.3 Hz, 1H), δ 7.89 (m, 2H), δ 7.73 (m, 1H), δ 7.63 (m, 3H), δ 7.40 (t, J=8.3 Hz, 1H), δ 7.17 (t, J=8.3 Hz, 1H), δ 6.46 (bs, 2H), δ 4.60 (t, J=7.8 Hz, 2H), δ 3.66 (t, J=7.3 Hz, 2H), δ 2.86 (t, J=7.8 Hz, 2H), δ 2.04 (m, 2H), δ 1.73 (p, J=7.6 Hz, 2H), δ 1.39 (sextet, J=7.3 Hz, 2H), δ 0.92 (t, J=7.3 Hz, 3H) MS (CI) for $C_{23}H_{26}N_4O_2S$ m/z 423 (MH$^+$), 322, 281.

EXAMPLE 21

1-[5-(methylsulfonyl)pentyl]-2-propyl-1H-imidazo[4,5-c]quinolin-4-amine

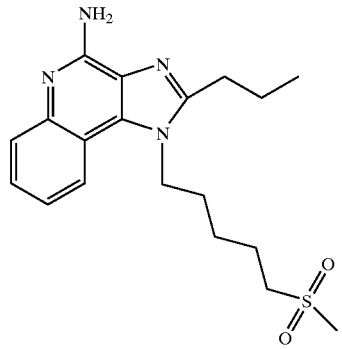

Part A

Using the general method of Example 1 Part D, $N^4$-(5-chloropentyl)quinoline-3,4-diamine (~20.4 mmol) was cyclized using trimethyl orthobutyrate (3.6 g, 24.5 mmol) in the presence of pyridine hydrochloride (~0.1 g). The crude product was purified by column chromatography (silica gel eluting with 95/5 dichloromethane/methanol) to provide 3.9 g of 1-(5-chloropentyl)-2-propyl-1H-imidazo[4,5-c]quinoline as a light green solid.

Part B

Using the general method of Example 1 Part E, 1-(5-chloropentyl)-2-propyl-1H-imidazo[4,5-c]quinoline (3.9 g, 12.36 mmol) was oxidized to provide 1-(5-chloropentyl)-2-propyl-1H-imidazo[4,5-c]quinoline-5N-oxide as a dark orange oil.

Part C

Using the general method of Example 3 Part B, the material from Part B was aminated to provide 1-(5-chloropentyl)-2-propyl-1H-imidazo[4,5-c]quinoline-4-amine. The crude product was slurried with diethyl ether, isolated by filtration, washed with diethyl ether and then dried to provide 3.42 g of the product as a white powder.

Part D

A suspension of 1-(5-chloropentyl)-2-propyl-1H-imidazo[4,5-c]quinoline-4-amine (2.5 g, 7.56 mmol) in anhydrous N,N-dimethylformamide (38 mL) was heated to 80° C. to provide a light yellow solution. Sodium thiomethoxide (0.67 g of 95%, 9.07 mmol) was added in a single portion and heating was continued for 110 minutes. The resulting light brown suspension was poured into water (300 mL) with rapid stirring. A white solid precipitated. After the suspension had cooled to ambient temperature, several scoops of solid sodium carbonate were added. The suspension was chilled in an ice water bath with stirring for 1 hour. The solid was isolated by filtration, washed with cold water and then dried to provide 2.3 g of 1-[5-(methylthio)pentyl]-2-propyl-1H-imidazo[4,5-c]quinoline-4-amine as a white powder.

Part E

Using the general method of Example 5, the material from Part D was oxidized and the crude product purified to provide 0.88 g of 1-[5-(methylsulfonyl)pentyl]-2-propyl-1H-imidazo[4,5-c]quinolin-4-amine as a white powder, m.p. 179–181° C.

Analysis: Calculated for $C_{19}H_{26}N_4O_2S$: % C, 60.94; % H, 7.00; % N, 14.96; Found: % C, 60.60; % H, 7.03; % N, 14.84. $^1$H NMR (300 MHz, DMSO-$d_6$) δ 8.0 (d, J=7.8 Hz, 1H), 7.61 (d, J=7.5 Hz, 1H), 7.41 (t, J=8.4, Hz, 1H), 7.25 (dt, J=8.1, 1.2 Hz, 1 H), 6.43 (s, 2 H), 4.50 (t, J=7.5 Hz, 2 H), 3.10 (t, J=8.1 Hz, 2 H), 2.92 (s, 3 H), 2.90 (m, 2 H), 1.84 (quintet, J=7.5 Hz, 4 H), 1.74 (m, 2 H), 1.54 (quintet, J=8.1 Hz, 2H), 1.04 (t, J=7.5 Hz, 3H); MS(CI) m/e 375 (M+H).

EXAMPLE 22

2-methyl-1-[3-(methylthio)propyl]-1H-imidazo[4,5-c]quinolin-4-amine

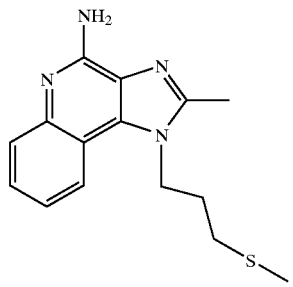

Part A

Using the general method of Example 1 Part D, $N^4$-(3-chloropropyl)quinoline-3,4-diamine (~37.6 mmol) was cyclized using 1,1,1-trimethoxyethane (5.43 g, 45.2 mmol) in the presence of pyridine hydrochloride (0.43 g) to provide 7.6 g of 1-(3-chloropropyl)-2-methyl-1H-imidazo[4,5-c]quinoline as a light yellow solid.

Part B

Using the general method of Example 1 Part E, 1-(3-chloropropyl)-2-methyl-1H-imidazo[4,5-c]quinoline (7.53 g, 29.0 mmol) was oxidized to provide 1-(3-chloropropyl)-2-methyl-1H-imidazo[4,5-c]quinoline-5N-oxide as a tan solid.

Part C

Using the general method of Example 3 Part B, the material from Part B was aminated. The crude product was slurried with diethyl ether and then recrystallized from isopropanol to provide 3.7 g of 1-(3-chloropropyl)-2-methyl-1H-imidazo[4,5-c]quinoline-4-amine as a light yellow powder.

Part D

Using the general method of Example 21 Part D, the material from Part C was reacted with sodium thiomethoxide. The crude product was recrystallized from acetonitrile and then triturated with diethyl ether to provide 3.07 g of 2-methyl-1-[3-(methylthio)propyl]-1H-imidazo[4,5-c]quinolin-4-amine as gold needles, m.p. 199–202° C.

Analysis: Calculated for $C_{15}H_{18}N_4S$: % C, 62.91; % H, 6.34; % N, 19.56; Found: % C, 62.74; % H, 6.20; % N, 19.47. $^1$H NMR (300 MHz, DMSO-$d_6$) δ 8.13 (d, J=7.5 Hz, 1 H), 7.61 (d, J=7.5 Hz, 1 H), 7.42 (t, J=7.2, Hz, 1 H), 7.24 (t, J=7.2, Hz, 1 H), 6.51 (s, 2 H), 4.58 (t, J=7.5 Hz, 2 H), 2.67–2.61 (m, 5 H), 2.09 (m, 5 H); MS(CI) m/e 287 (M+H).

EXAMPLE 23

2-methyl-1-[3-(methylsulfonyl)propyl]-1H-imidazo[4,5-c]quinolin-4-amine

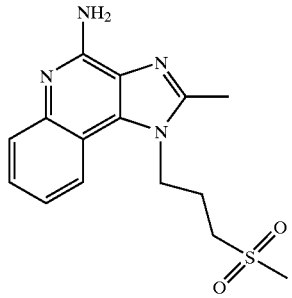

Using the general method of Example 5, 2-methyl-1-[3-(methylthio)propyl]-1H-imidazo[4,5-c]quinolin-4-amine (1.8 g, 6.28 mmol) was oxidized and the crude product purified to provide 0.91 g of 2-methyl-1-[3-(methylsulfonyl)propyl]-1H-imidazo[4,5-c]quinolin-4-amine as a white solid, m.p. 225–228° C.

Analysis: Calculated for $C_{15}H_{18}N_4O_2S$: % C, 56.59; % H, 5.70; % N, 17.60; Found: % C, 56.60; % H, 5.68; % N, 17.61. $^1$H NMR (300 MHz, DMSO-$d_6$) δ 8.04 (d, J=8.1 Hz, 1 H), 7.61 (d, J=8.1 Hz, 1 H), 7.43 (t, J=7.2, Hz, 1 H), 7.25 (dt, J=6.9, 1.2, Hz, 1 H), 6.56 (s, 2 H), 4.65 (t, J=7.8 Hz, 2 H), 3.38 (t, J=7.8 Hz, 2 H), 3.01 (s, 3 H), 2.62 (s, 3 H), 2.24 (quintet, J=7.5 Hz, 2 H); MS(CI) m/e 319 (M+H).

EXAMPLE 24

2-ethyl-1-[3-(methylthio)propyl]-1H-imidazo[4,5-c]quinolin-4-amine

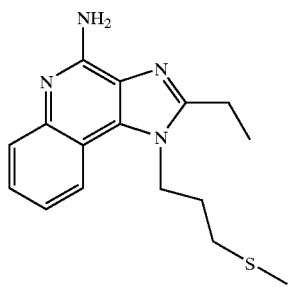

Part A

Using the general method of Example 1 Part D, $N^4$-(3-chloropropyl)quinoline-3,4-diamine (~37.6 mmol) was cyclized using triethyl orthopropionate (7.96 g, 45.2 mmol) in the presence of pyridine hydrochloride (0.43 g). The crude product was purified by chromatography (silica gel eluting with 95/5 dichloromethane/methanol) to provide 7.33 g of 1-(3-chloropropyl)-2-ethyl-1H-imidazo[4,5-c]quinoline as a white solid.

Part B

Using the general method of Example 1 Part E, 1-(3-chloropropyl)-2-ethyl-1H-imidazo[4,5-c]quinoline (7.33 g, 26.8 mmol) was oxidized to provide 1-(3-chloropropyl)-2-ethyl-1H-imidazo[4,5-c]quinoline-5N-oxide as a solid.

Part C

Using the general method of Example 3 Part B, the material from Part B was aminated. The crude product was slurried with diethyl ether to provide 6.2 g of 1-(3-chloropropyl)-2-ethyl-1H-imidazo[4,5-c]quinoline-4-amine as a white powder.

Part D

Using the general method of Example 21 Part D, 1-(3-chloropropyl)-2-ethyl-1H-imidazo[4,5-c]quinoline-4-amine (4.0 g, 13.85 mmol) was reacted with sodium thiomethoxide (1.53 g, 20.78 mmol). The crude product was triturated with diethyl ether to provide 3.65 g of a white powder. A portion (1.5 g) was purified by chromatography (silica gel eluting with 95/5 dichloromethane/methanol) to provide 1 g of 2-ethyl-1-[3-(methylthio)propyl]-1H-imidazo[4,5-c]quinolin-4-amine as a white powder, m.p. 210–212° C.

Analysis: Calculated for $C_{16}H_{20}N_4S$: % C, 63.97; % H, 6.71; % N, 18.65; Found: % C, 63.70; % H, 6.59; % N, 18.62. $^1$H NMR (300 MHz, DMSO-$d_6$) δ 8.14 (d, J=8.7 Hz, 1 H), 7.62 (dd, J=6.9, 1.2 Hz, 1 H), 7.42 (dt, J=7.2, 1.2 Hz, 1 H), 7.25 (dt, J=6.9, 1.2, Hz, 1 H), 6.48 (s, 2 H), 4.58 (t, J=7.5 Hz, 2 H), 2.97 (quartet, J=7.5 Hz, 2 H), 2.65 (t, J=6.9 Hz, 2 H), 2.12–2.02 (m, 5 H), 1.38 (t, J=7.5 Hz, 3H); MS(CI) m/e 301 (M+H).

EXAMPLE 25

2-ethyl-1-[3-(methylsulfonyl)propyl]-1H-imidazo[4, 5-c]quinolin-4-amine

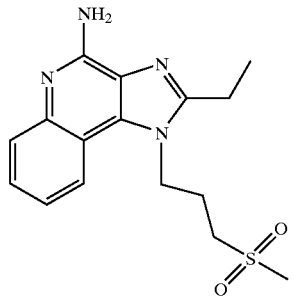

Using the general method of Example 5, 2-ethyl-1-[3-(methylthio)propyl]-1H-imidazo[4,5-c]quinolin-4-amine (2.1 g, 6.99 mmol) was oxidized to provide 1.7 g of 2-ethyl-1-[3-(methylsulfonyl)propyl]-1H-imidazo[4,5-c]quinolin-4-amine as a fine white powder, m.p. >250° C.

Analysis: Calculated for $C_{16}H_{20}N_4O_2S$: % C, 57.81; % H, 6.06; % N, 16.85; Found: % C, 57.81; % H, 5.88; % N, 16.78. $^1$H NMR (300 MHz, DMSO-$d_6$) δ 8.12 (d, J=8.1 Hz, 1 H), 7.62 (d, J=8.1 Hz, 1 H), 7.43 (t, J=8.1, Hz, 1 H), 7.25 (t, J=8.4, Hz, 1 H), 6.45 (s, 2 H), 4.65 (t, J=7.8 Hz, 2 H), 3.39 (t, J=7.8 Hz, 2 H), 3.00 (s, 3 H), 2.96 (quartet, J=7.2 Hz, 2 H), 2.22 (quintet, J=7.8 Hz, 2 H), 1.38 (t, J=7.2Hz, 3 H); MS(CI) m/e 333 (M+H)

EXAMPLE 26

2-methyl-1-[4-(methylthio)butyl]-1H-imidazo[4,5-c]quinolin-4-amine

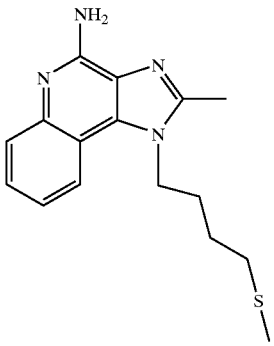

Part A

Using the general method of Example 19 Part A, 4-[(3-nitroquinolin-4-yl)amino]butan-1-ol (120 g, 0.459 mol) was chlorinated with thionyl chloride (109 g, 0.919 mol) to provide 127.9 g of N-(4-chlorobutyl)-3-nitroquinolin-4-amine as a yellow powder.

Part B

Using the general method of Example 1 Part C, N-(4-chlorobutyl)-3-nitroquinolin-4-amine (7.0 g, 25.0 mmol) was reduced to provide $N^4$-(4-chlorobutyl)quinoline-3,4-diamine as a dark brown oil.

Part C

Using the general method of Example 1 Part D, the material from Part B was cyclized using 1,1,1-trimethoxyethane (3.6 g, 30.12 mmol) in the presence of pyridine hydrochloride (0.29 g) to provide 7.6 g of 1-(4-chlorobutyl)-2-methyl-1H-imidazo[4,5-c]quinoline as a dark brown oil.

Part D

Using the general method of Example 1 Part E, 1-(4-chlorobutyl)-2-methyl-1H-imidazo[4,5-c]quinoline (5.8 g of the material from Part C) was oxidized to provide ~6.33 g of 1-(4-chlorobutyl)-2-methyl-1H-imidazo[4,5-c]quinoline-5N-oxide as an amber oil.

Part E

Using the general method of Example 3 Part B, the material from Part D was aminated and purified to provide 1.84 g of 1-(4-chlorobutyl)-2-methyl-1H-imidazo[4,5-c]quinolin-4-amine as an off-white fluffy powder.

Part F

Using the general method of Example 21 Part D, the material from Part E was reacted with sodium thiomethoxide. The crude product was recrystallized from 1,2-dichloroethane and then triturated with diethyl ether to provide 1.21 g of 2-methyl-1-[4-(methylthio)butyl]-1H-imidazo[4,5-c]quinolin-4-amine as a white powder, m.p. 190–193° C.

Analysis: Calculated for $C_{16}H_{20}N_4S$: % C, 63.97; % H, 6.71; % N, 18.65; Found: % C, 63.77; % H, 6.65; % N, 18.55. $^1$H NMR (300 MHz, DMSO-$d_6$) δ 8.05 (d, J=8.1 Hz, 1 H), 7.60 (d, J=9.3 Hz, 1 H), 7.41 (t, J=8.4 Hz, 1 H), 7.24 (t, J=8.4 Hz, 1 H), 6.48 (s, 2 H), 5.42 (t, J=7.4 Hz, 2 H), 2.60 (s, 3 H), 2.53 (m, 2 H), 2.02 (s, 3 H), 1.91 (quintet, J=7.5 Hz, 2 H), 1.69 (quintet, J=7.5 Hz, 2 H) MS(CI) m/e 301 (M+H).

EXAMPLE 27

2-methyl-1-[4-(methylsulfinyl)butyl]-1H-imidazo[4,5-c]quinolin-4-amine

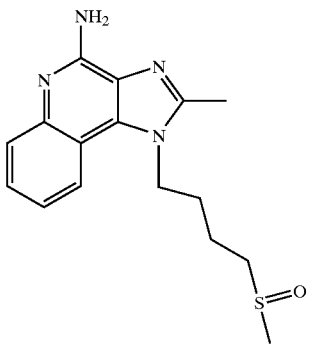

Using the general method of Example 18, 2-methyl-1-[4-(methylthio)butyl]-1H-imidazo[4,5-c]quinolin-4-amine (2.15 g, 7.16 mmol) was oxidized to provide the crude sulfoxide. This material was purified by sequentially recrystallizing from acetonitrile, chromatographing (silica gel eluting with 90/10 dichloromethane/methanol) and triturating with diethyl ether to provide 0.7 g of 2-methyl-1-[4-(methylsulfinyl)butyl]-1H-imidazo[4,5-c]quinolin-4-amine as a white powder, m.p. 184–187° C.

Analysis: Calculated for $C_{16}H_{20}N_4OS$: % C, 60.73: % H, 6.37; % N, 17.71; Found: % C, 60.37; % H, 6.38; % N, 17.52. $^1$H NMR (300 MHz, DMSO-$d_6$) δ 8.04 (d, J=8.1 Hz, 1 H), 7.61 (d, J=8.1 Hz, 1 H), 7.42 (dt, J=6.9, 1.3 Hz, 1 H), 7.26 (dt, J=6.9, 1.3, Hz, 1 H), 6.53 (s, 2 H), 4.55 (t, J=7.2 Hz, 2 H), 2.87–2.66 (m, 2 H), 2.67 (s, 3 H), 2.51 (s, 3 H), 1.95 (m, 2 H), 1.81 (quintet, J=7.5 Hz, 2 H) MS(CI) m/e 317 (M+H).

EXAMPLE 28

2-ethyl-1-[4-(methylthio)butyl]-1H-imidazo[4,5-c]quinolin-4-amine

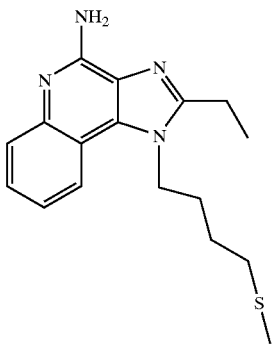

Part A

Using the general method of Example 1 Part D, $N^4$-(4-chlorobutyl)quinoline-3,4-diamine (~35.75 mmol) was cyclized using triethyl orthopropionate (7.56 g, 42.9 mmol) in the presence of pyridine hydrochloride (0.41 g). The crude product was purified by chromatography (silica gel eluting with 95/5 dichloromethane/methanol) to provide 7.5 g of 1-(4-chlorobutyl)-2-ethyl-1H-imidazo[4,5-c]quinoline as a white powder.

Part B

Using the general method of Example 1 Part E, the material from Part A was oxidized to provide 1-(4-chlorobutyl)-2-ethyl-1H-imidazo[4,5-c]quinoline-5N-oxide as a tan solid.

Part C

Using the general method of Example 3 Part B, the material from Part B was aminated and purified to provide 7.0 g of 1-(4-chlorobutyl)-2-ethyl-1H-imidazo[4,5-c]quinoline-4-amine as a white powder.

Part D

Using the general method of Example 21 Part D, the material from Part C was reacted with sodium thiomethoxide. The crude product was recrystallized from isopropanol and then triturated with diethyl ether to provide 1.55 g of 2-ethyl-1-[4-(methylthio)butyl]-1H-imidazo[4,5-c]quinolin-4-amine as a white powder, m.p. 183–186° C.

Analysis: Calculated for $C_{17}H_{22}N_4S$: % C, 64.93; % H, 7.05; % N, 17.82; Found: % C, 65.07; % H, 7.17; % N, 17.66. $^1$H NMR (300 MHz, DMSO-d6) δ 8.04 (d, J=7.5 Hz, 1 H), 7.61 (dd, J=9.3, 1.5 Hz, 1 H), 7.41 (dt, J=7.8, 1.4 Hz, 1 H), 7.25 (dt, J=7.5, 1.5 Hz, 1 H), 6.44 (s, 2 H), 4.52 (t, J=7.50 Hz, 2 H), 2.95 (quartet, J=7.5 Hz, 2 H), 2.55 (m, 2 H), 2.02 (s, 3 H), 1.90 (m, 2 H), 1.71 (m, 2 H), 1.38 (t, J=7.2Hz, 3 H) MS(CI) m/e 315 (M+H).

EXAMPLE 29

2-ethyl-1-[4-(methylsulfonyl)butyl]-1H-imidazo[4,5-c]quinolin-4-amine

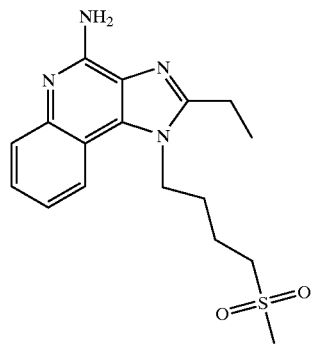

Using the general method of Example 5, 2-ethyl-1-[4-(methylthio)butyl]-1H-imidazo[4,5-c]quinolin-4-amine (2.3 g, 7.31 mmol) was oxidized. The crude product was sequentially triturated with diethyl ether, chromatographed (silica gel eluting with 90/10 dichloromethane/methanol), recrystallized from ethanol and triturated with diethyl ether to provide 1.18 g of 2-ethyl-1-[4-(methylsulfonyl)butyl]-1H-imidazo[4,5-c]quinolin-4-amine as a white powder, m.p. 182–185° C.

Analysis: Calculated for $C_{17}H_{22}N_4O_2S$: % C, 58.94; % H, 6.40; % N, 16.17; Found: % C, 58.89; % H, 6.51; % N, 16.13. $^1$H NMR (300 MHz, DMSO-$d_6$) δ 8.04 (d, J=8.1 Hz, 1 H), 7.62 (dd, J=8.1, 1.5 Hz, 1 H), 7.42 (dt, J=6.9, 1.2 Hz, 1 H), 7.26 (t, J=7.4 Hz, 1 H), 6.45 (s, 2 H), 4.55 (t, J=7.05 Hz, 2 H), 3.21 (t, J=7.2Hz, 2 H), 2.96 (m, 5 H), 1.91 (m, 4 H), 1.38 (t, J=7.2Hz, 3 H) MS(CI) m/e 347 (M+H).

EXAMPLE 30

1-[4-(methylsulfonyl)butyl]-2-propyl-1H-imidazo[4,5-c]quinolin-4-amine

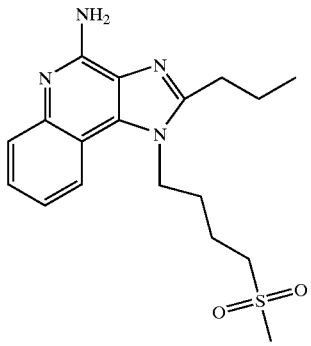

Part A

Using the general method of Example 1 Part D, $N^4$-(4-chlorobutyl)quinoline-3,4-diamine (~21.45 mmol) was cyclized using trimethyl orthobutyrate (3.8 g, 25.74 mmol) in the presence of pyridine hydrochloride (0.1 g). The crude product was purified by chromatography (silica gel eluting with 95/5 dichloromethane/methanol) to provide 3.6 g of 1-(4-chlorobutyl)-2-propyl-1H-imidazo[4,5-c]quinoline as a light green oil which slowly solidified.

Part B

Using the general method of Example 1 Part E, the material from Part A was oxidized to provide 1-(4-chlorobutyl)-2-propyl-1H-imidazo[4,5-c]quinoline-5N-oxide as a light orange oil.

Part C

Using the general method of Example 3 Part B, the material from Part B was aminated and purified to provide 3.0 g of 1-(4-chlorobutyl)-2-propyl-1H-imidazo[4,5-c]quinoline-4-amine as an off-white solid.

Part D

Using the general method of Example 21 Part D, the material from Part C was reacted with sodium thiomethoxide to provide 2.52 g of 1-[4-(methylthio)butyl]-2-propyl-1H-imidazo[4,5-c]quinolin-4-amine as a solid.

Part E

Using the general method of Example 5, the material from part D was oxidized. The crude product was sequentially chromatographed (silica gel eluting with 95/5 dichloromethane/methanol), recrystallized from ethanol and triturated with diethyl ether to provide 1.15 g of a solid. This material was dissolved in hot N,N-dimethylformamide (6 mL) and the solution was poured into water (100 mL). The resulting precipitate was isolated by filtration, washed with water and dried to obtain 1.0 g of 1-[4-(methylsulfonyl)butyl]-2-propyl-1H-imidazo[4,5-c]quinolin-4-amine as an off-white powder, m.p. 202–204° C.

Analysis: Calculated for $C_{18}H_{24}N_4O_2S$: % C, 59.98; % H, 6.71; % N, 15.54; Found: % C, 59.71; % H, 6.69; % N, 15.41. $^1$H NMR (300 MHz, DMSO-d6) δ 8.03 (d, J=8.1 Hz, 1 H), 7.61 (dd, J=8.1, 1.2 Hz, 1 H), 7.42 (dt, J=7.2, 1.2, Hz, 1 H), 7.26 (t, J=7.5, Hz, 1 H), 6.44 (s, 2 H), 4.55 (t, J=6.5 Hz, 2 H), 3.21 (t, J=7.2 Hz, 2 H), 2.96 (s, 3 H), 2.91 (t, J=7.5 Hz, 2 H), 1.92–1.79 (m, 6H), 1.04 (t, J=7.5Hz, 3 H); MS(CI) m/e 361 (M+H)

EXAMPLE 31

2-butyl-1-[4-(methylsulfinyl)butyl]-1H-imidazo[4,5-c]quinolin-4-amine

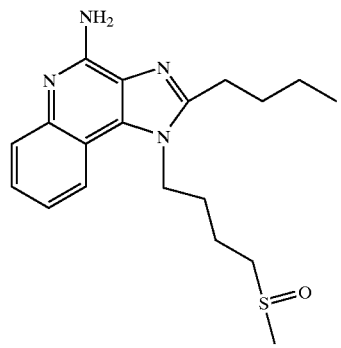

Using the general method of Example 18, 2-butyl-1-[4-(methylthio)butyl]-1H-imidazo[4,5-c]quinolin-4-amine (2.5 g, 7.30 mmol) was oxidized and purified to provide 1.5 g of 2-butyl-1-[4-(methylsulfinyl)butyl]-1H-imidazo[4,5-c]quinolin-4-amine as a white solid, m.p. 126–128° C.

Analysis: Calculated for $C_{19}H_{26}N_4OS.0.25\ H_2O$: % C, 62.87; % H, 7.36; % N, 15.43; Found: % C, 62.57; % H, 7.34; % N, 15.47. $^1$H NMR (300 MHz, DMSO-d6) δ 8.03 (d, J=8.1 Hz, 1 H), 7.61 (d, J=9.0 Hz, 1 H), 7.41 (t, J=6.9 Hz, 1 H), 7.25 (t, J=7.1, Hz, 1 H), 6.46 (s, 2 H), 4.56 (t, J=7.3 Hz, 2 H), 2.93 (t, J=7.8 Hz, 2 H), 2.87–2.66 (m, 2 H), 2.51 (s, 3 H), 1.93–1.75 (m, 6 H), 1.46 (sextet, J=7.5 Hz, 2 H), 0.96 (t, J=7.4 Hz, 3 H); MS(CI) m/e 359 (M+H).

EXAMPLE 32

2-methyl-1-[2-(methylthio)ethyl]-1H-imidazo[4,5-c]quinolin-4-amine

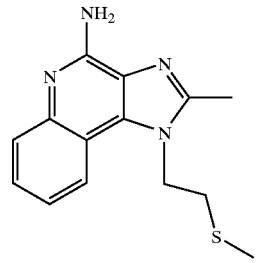

Part A

Using the general method of Example 6 Part A except that a solvent (55 mL of 1,2-dichloroethane) was included, 2-(4-amino-2-methyl-1H-imidazo[4,5-c]quinolin-1-yl)ethanol (4.0 g, 16.51 mol) was chlorinated using thionyl chloride (2.41 mL, 33.02 mmol) to provide 3.9 g of 1-(2-chloroethyl)-2-methyl-1H-imidazo[4,5-c]quinoline-4-amine as a fine, white powder.

Part B

Using the general method of Example 21 Part D, 1-(2-chloroethyl)-2-methyl-1H-imidazo[4,5-c]quinoline-4-amine (3.75 g, 14.38 mmol) was reacted with sodium thiomethoxide (1.6 g, 21.57 mmol) to provide 3.2 g of the thioether as an off-white solid. A portion (1.4 g) was recrystallized form ethanol and then triturated with diethyl ether to provide 0.9 g of 2-methyl-1-[2-(methylthio)ethyl]-1H-imidazo[4,5-c]quinolin-4-amine as a fine white powder, m.p. 193–195° C.

Analysis: Calculated for $C_{14}H_{16}N_4S$: % C, 61.74; % H, 5.92; % N, 20.57; Found: % C, 61.64; % H, 5.97; % N, 20.66. $^1$H NMR (300 MHz, DMSO-d6) δ 8.00 (dd, J=7.8, 1.5 Hz, 1 H), 7.61 (dd, J=8.1, 1.4 Hz, 1 H), 7.19 (dt, J=7.8, 1.2 Hz, 1 H), 7.25 (dt, J=7.5, 1.5 Hz, 1 H), 6.51 (s, 2 H), 4.72 (t, J=6.9 Hz, 2 H), 2.99 (t, J=6.8 Hz, 2 H), 2.66 (s, 3 H), 2.08 (s, 3 H); MS(CI) m/e 273 (M+H)

EXAMPLE 33

2-methyl-1-[2-(methylsulfonyl)ethyl]-1H-imidazo[4,5-c]quinolin-4-amine

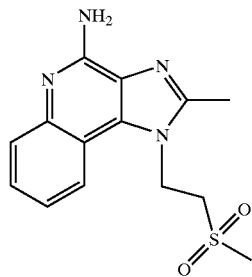

3-Chloroperbenzoic acid (3.35 g of 75%, 14:54 mmol) was added in portions to a suspension of 2-methyl-1-[2-(methylthio)ethyl]-1H-imidazo[4,5-c]quinolin-4-amine (1.8 g, 6.61 mmol) in chloroform (33 mL). After about 1 equivalent of the oxidant had been added, a precipitate formed. Additional chloroform was added along with the remaining oxidant. The reaction mixture was stirred at ambient temperature for 1 hour and then it was chilled in an ice bath. A white solid was isolated by filtration and then washed with cold dichloromethane. This solid was suspended in water (100 mL). Solid sodium carbonate was added until the pH reached 10. The suspension was stirred at ambient temperature for several hours then the solid was isolated by filtration and washed with water to provide ~1.5 g of an off-white solid. Analysis by H-NMR indicated that sulfoxide was present. This material was suspended in dichloromethane (23 mL) and 3-chloroperbenzoic acid (0.25 g) was added in portions. After about 15 minutes another portion of oxidant was added. The reaction mixture was concentrated under reduced pressure. The residue was stirred in water (100 mL) and solid sodium carbonate was added until the pH reached 10. A brown solid was isolated by filtration and washed with water. This material was purified by chromatography (silica gel eluting with 95/5 dichloromethane/methanol) to provide a white solid. This material was triturated with diethyl ether to provide 0.56 g of 2-methyl-1-[2-(methylsulfonyl)ethyl]-1H-imidazo[4,5-c]quinolin-4-amine as a fine white powder, m.p. 242–245° C.

Analysis: Calculated for $C_{14}H_{16}N_4O_2S$: % C, 55.25; % H, 5.30; % N, 18.41; Found: % C, 54.92; % H, 5.19; % N, 18.29. $^1$H NMR (300 MHz, DMSO-$d_6$) δ 8.05 (d, J=6.6 Hz, 1 H), 7.63 (d, J=6.6 Hz, 1 H), 7.43 (t, J=7.2 Hz, 1 H), 7.25 (t, J=6.9, Hz, 1 H), 6.31 (s, 2 H), 4.95 (t, J=7.2 Hz, 2 H), 3.77 (t, J=7.2 Hz, 2 H), 3.08 (s, 3 H), 2.66 (s, 3 H); MS(CI) m/e 305 (M+H).

EXAMPLE 34

2-methyl-1-[4-(methylsulfonyl)butyl]-1H-imidazo[4,5-c]quinolin-4-amine

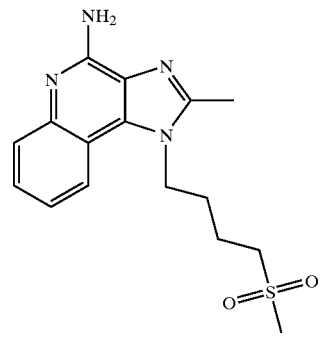

Part A

Sodium thiomethoxide (2.02 g of 95%, 27.40 mmol) was added in a single portion to a solution of 1-(4-chlorobutyl)-2-methyl-1H-imidazo[4,5-c]quinoline (5.0 g, 18.26 mmol) in anhydrous N,N-dimethylformamide (91 mL). After 30 minutes the reaction mixture was poured with rapid stirring into water (500 mL). The resulting solution was extracted with chloroform (2×200 mL). The organic layers were combined, washed with saturated aqueous sodium bicarbonate (100 mL) then with brine (100 mL), dried over sodium sulfate, filtered and then concentrated under reduced pressure to provide 5.0 g 2-methyl-1-[4-(methylthio)butyl]-1H-imidazo[4,5-c]quinoline as a light yellow oil.

Part B

Using the general method of Example 11 Part F, the material from Part A was oxidized to provide 2-methyl-1-[4-(methylsulfonyl)butyl]-1H-imidazo[4,5-c]quinoline-5N-oxide as a light orange solid.

Part C

Using the general method of Example 3 Part B except that dichloromethane was used as a solvent in place of chloroform, the material from Part B was aminated. The crude material was purified by chromatography (silica gel eluting with 90/10 dichloromethane/methanol) followed by trituration with diethyl ether to provide 1.67 g of 2-methyl-1-[4-(methylsulfonyl)butyl]-1H-imidazo[4,5-c]quinolin-4-amine as a fine white solid, m.p. 206–209° C.

Analysis: Calculated for $C_{16}H_{20}N_4O_2S$: % C, 57.81; % H, 6.06; % N, 16.85; Found: % C, 57.70; % H, 6.10; % N, 16.64. $^1$H NMR (300 MHz, DMSO-$d_6$) δ 8.05 (d, J=8.1 Hz, 1 H), 7.61 (d, J=8.7 Hz, 1 H), 7.42 (t, J=7.8 Hz, 1 H), 7.25 (t, J=7.6 Hz, 1 H), 6.51 (s, 2 H), 4.55 (t, J=7.2 Hz, 2 H), 3.20 (t, J=7.4Hz, 2 H), 2.96 (s, 3 H), 2.61 (s, 3 H), 1.91 (m, 4 H); MS(CI) m/e 333 (M+H).

EXAMPLE 35

2-ethyl-1-[2-(methylsulfonyl)ethyl]-1H-imidazo[4,5-c]quinolin-4-amine

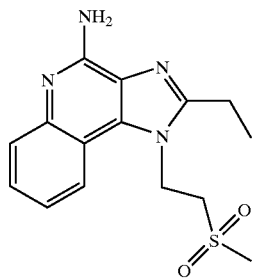

Part A

Using the general method of Example 1 Part A, 4-chloro-3-nitroquinoline (15.0 g, 71.90 mol) was reacted with 2-chloroethylamine monohydrochloride (8.3 g, 71.90 mmol). The crude product was suspended in water (300 mL) and solid sodium carbonate was added to adjust the pH to 10. The suspension was stirred overnight and then cooled in an ice bath. The solid was then isolated by filtration and washed with chilled water to provide 15.88 g of N-(2-chloroethyl)-3-nitroquinolin-4-amine as a bright yellow fluffy solid.

Part B

Using the general method of Example 21 Part D, N-(2-chloroethyl)-3-nitroquinolin-4-amine (6.0 g, 23.84 mmol) was reacted with sodium thiomethoxide (2.11 g of 95%, 28.61 mmol) to provide 4.95 g of N-[2-(methylthio)ethyl]-3-nitroquinolin-4-amine as a dull yellow solid.

Part C

Using the general method of Example 1 Part C, N-[2-(methylthio)ethyl]-3-nitroquinolin-4-amine (4.71 g, 17.89 mmol) was reduced to provide $N^4$-[2-(methylthio)ethyl]quinoline-3,4-diamine as a light brown oil.

Part D

Using the general method of Example 1 Part D, the material from Part C was cyclized using triethyl orthopropionate. The crude product was purified by chromatography (silica gel eluting with 95/5 dichloromethane/methanol) to provide 3.1 g of 2-ethyl-1-[2-(methylthio)ethyl]-1H-imidazo[4,5-c]quinoline as an off-white solid.

Part E

Using the general method of Example 11 Part F, the material from Part D was oxidized to provide 3.3 g of 2-ethyl-1-[2-(methylsulfonyl)ethyl]-1H-imidazo[4,5-c]quinoline-5N-oxide as an off-white solid.

Part F

Using the general method of Example 3 Part B, the material from Part E was aminated and purified to provide 0.2 g of 2-ethyl-1-[2-(methylsulfonyl)ethyl]-1H-imidazo[4,5-c]quinolin-4-amine as a solid, m.p. 222–225° C.

Analysis: Calculated for $C_{15}H_{18}N_4O_2S$: % C, 56.59; % H 5.70; % N, 17.60; Found: % C, 56.37; % H, 5.59; % N, 17.34. $^1$H NMR (300 MHz, DMSO-$d_6$) δ 8.06 (d, J=8.7 Hz, 1 H), 7.63 (d, J=8.7 Hz, 1 H), 7.44 (t, J=8.1, Hz, 1 H), 7.26 (t, J=8.1, Hz, 1 H), 6.50 (s, 2 H), 4.95 (t, J=7.2Hz, 2 H), 3.78 (t, J=7.2 Hz, 2 H), 3.12 (s, 3 H), 3.02 (quartet, J=7.5 Hz, 2 H), 1.39 (t, J=7.2 Hz, 3 H); MS(CI) m/e 319 (M+H).

EXAMPLE 36

1-[2-(methylsulfonyl)ethyl]-2-propyl-1H-imidazo[4,5-c]quinolin-4-amine

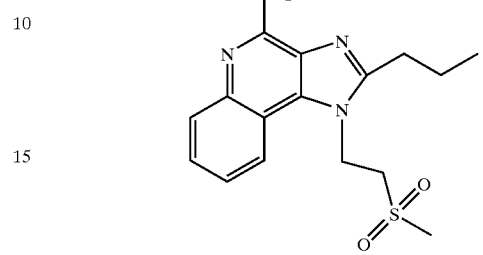

Part A $N^4$-[2-(Methylthio)ethyl]quinoline-3,4-diamine (4.2 g, 19.2 mmol), trimethyl orthobutyrate (2.86 g, 19.2 mmol), pyridine hydrochloride (catalytic amount) and toluene were combined in a pressure vessel and heated at 140° C. for 1 hour. The reaction mixture was allowed to cool and then it was concentrated under reduced pressure to provide 4.9 g of 1-[2-(methylthio)ethyl]-2-propyl-1H-imidazo[4,5-c]quinoline.

Part B

3-Chloroperbenzoic acid (14.12 g of 65%, 53.2 mmol) was added in portions to a solution of the material from Part A in chloroform (100 mL). After about 30 minutes the reaction mixture was washed with aqueous sodium carbonate, water and then with brine. The organic layer was combined with excess ammonium hydroxide. p-Toluenesulfonyl chloride (3.6 g, 18.9 mmol) was added in portions accompanied by vigorous stirring. After 1 hour the reaction mixture was diluted with chloroform (100 mL) and water (100 mL). The organic layer was separated, washed with water and then concentrated under reduced pressure. The resulting oil was purified by chromatography (silica gel eluting with 98/2 dichloromethane/methanol). The material crystallized from dichloromethane and was isolated by filtration to provide 0.9 g of 1-[2-(methylsulfonyl)ethyl]-2-propyl-1H-imidazo[4,5-c]quinolin-4-amine as a solid, m.p. 212–214° C.

Analysis: Calculated for $C_{16}H_{20}N_4O_2S \cdot 0.08\ CH_2Cl_2$: % C, 56.94; % H, 5.99; % N, 16.52 Found: % C, 56.95; % H, 5.91; % N, 16.59. $^1$H NMR (300 MHz, DMSO-$d_6$) δ 8.06 (d, J=7.5 Hz, 1 H), 7.64 (d, J=7.2 Hz, 1 H), 7.43 (t, J=7.2 Hz, 1 H), 7.25 (t, J=6.9 Hz, 1 H), 6.47 (s, 2 H), 4.94 (t, J=7.2 Hz, 2 H), 3.76 (t, J=7.2 Hz, 2 H), 3.11 (s, 3 H), 2.97 (t, J=7.5 Hz, 2 H), 1.87 (sextet, J=7.2 Hz, 2 H), 1.04 (t, J=7.2Hz, 3 H); MS (CI) m/e 333 (M+H)

EXAMPLE 37

2-butyl-1-{4-[(2,4-difluorophenyl)thio]butyl}-1H-imidazo[4,5-c]quinolin-4-amine

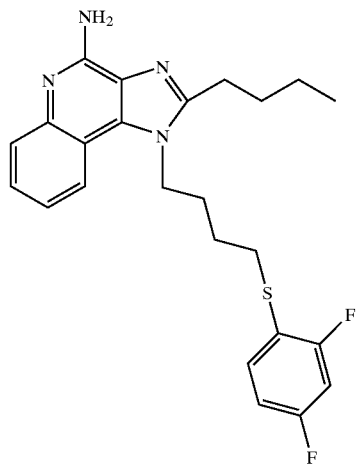

Part A

Using the general method of Example 1 Part D, $N^4$-(4-chlorobutyl)quinoline-3,4-diamine (119.1 g, 0.48 mole) was cyclized using trimethyl orthovalerate (93 g, 0.57 mol) in the presence of pyridine hydrochloride (1.1 g, 0.0095 mol) to provide 120 g of 2-butyl-1-(4-chlorobutyl)-1H-imidazo[4,5-c]quinoline as an ivory powder.

Part B

3-Chloroperbenzoic acid (110 g of 77%, 0.45 mol) was added in portions over a period of 30 minutes to a solution of 2-butyl-1-(4-chlorobutyl)-1H-imidazo[4,5-c]quinoline (118 g, 0.037 mol) in dichloromethane (1700 mL). After about 90 minutes the reaction mixture was diluted with additional dichloromethane, washed with 10% sodium hydroxide (×3) and brine, and then dried to provide 2-butyl-1-(4-chlorobutyl)-1H-imidazo[4,5-c]quinoline-5N-oxide.

Part C

Concentrated ammonium hydroxide (1100 mL) was added to the dichloromethane solution of 2-butyl-1-(4-chlorobutyl)-1H-imidazo[4,5-c]quinoline-5N-oxide from Part B. Tosyl chloride (68 g, 0.36 mol) was added in portions accompanied by vigorous stirring. After 30 minutes the layers were separated. The organic layer was diluted with dichloromethane, washed with 10% sodium hydroxide (×2) and brine, dried and then concentrated under reduced pressure to provide a tan solid. This material was recrystallized from acetonitrile (30 mL/g) to provide 91.6 g of 2-butyl-1-(4-chlorobutyl)-1H-imidazo[4,5-c]quinoline-4-amine as tan needles.

Analysis: Calculated for $C_{18}H_{23}ClN_4$: % C, 65.34; % H, 7.01; % N, 16.93; Found: % C, 65.32; % H, 7.09; % N, 16.94.

Part D 2,4-Difluorobenzenethiol (2 g, 13.7 mmol) was added to a suspension of sodium hydride (0.65 g of 60%, 16.5 mmol) in anhydrous N,N-dimethylformamide (30 mL). After the addition was complete the reaction mixture was allowed to stir at ambient temperature for about 30 minutes. 2-Butyl-1-(4-chlorobutyl)-1H-imidazo[4,5-c]quinoline-4-amine (4.5 g, 13.6 mmol) was added in a single portion. The reaction mixture was allowed to stir at ambient temperature for about 30 minutes; then it was poured into ice water and stirred. The aqueous layer was extracted with dichloromethane (5×75 mL). The combined organics were washed with water (3×100 mL) and brine, and then concentrated under reduced pressure to provide 6.7 g of a solid. This material was recrystallized from ethanol. A portion (1.1 g) was dried in a heated vacuum oven to provide 2-butyl-1-{4-[(2,4-difluorophenyl)thio]butyl}-1H-imidazo[4,5-c]quinolin as a solid, m.p. 122–126° C.

Analysis: Calculated for $C_{24}H_{26}F_2N_4S$: % C, 65.43; % H, 5.95; % N, 12.72; Found: % C, 65.41; % H, 5.98; % N, 12.80. $^1$H NMR (300 MHz, DMSO-$d_6$) δ 8.02 (d, J=7.5 Hz, 1 H), 7.62 (d, J=7.2 Hz, 1 H), 7.42 (m, 2 H), 7.25 (m, 2 H), 7.05 (t, J=6 Hz, 1 H), 6.46 (s, 2 H), 4.50 (t, J=7.5 Hz, 2 H), 2.97 (t, J=6.6 Hz, 2 H), 2.87 (t, J=7.2 Hz, 2 H), 1.92 (quintet, J=7.8 Hz, 2 H), 1.76 (quintet, J=7.8 Hz, 2 H), 1.64 (quintet, J=7.5 Hz, 2 H), 1.42 (sextet, J=7.5 Hz, 2 H), 0.94 (t, J=7.2 Hz, 3 H); MS (CI) m/e 441 (M+H)

EXAMPLE 38

2-butyl-1-{4-[(2,4-difluorophenyl)sulfonyl]butyl}-1H-imidazo[4,5-c]quinolin-4-amine

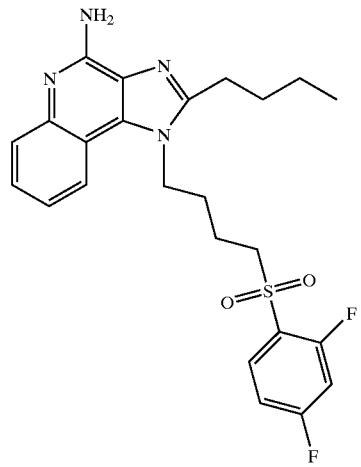

3-Chloroperbenzoic acid (6.025 g of 65%, 22.6 mmol) was added in portions to a solution of 2-butyl-1-{4-[(2,4-difluorophenyl)thio]butyl}-1H-imidazo[4,5-c]quinolin-4-amine (5.0 g, 11.3 mmol) in dichloromethane (50 mL). After the addition was completed the reaction mixture was allowed to stir for about 30 minutes. The reaction mixture was partitioned between dichloromethane and aqueous sodium carbonate. The aqueous layer was extracted with dichloromethane (3×500 mL). The combined organics were washed with water (5×100 mL) and brine and then concentrated under reduced pressure. The residue (6.1 g) was recrystallized from ethanol to provide 2-butyl-1-{4-[(2,4-difluorophenyl)sulfonyl]butyl}-1H-imidazo[4,5-c]quinolin-4-amine as a solid, m.p. 190–193° C.

Analysis: Calculated for $C_{24}H_{26}F_2N_4O_2S$: % C, 61.00; % H, 5.55; % N, 11.86; Found: % C, 61.33; % H, 5.38; % N, 11.70. $^1$H NMR (300 MHz, DMSO-$d_6$) δ 8.00 (d, J=8.1 Hz, 1 H), 7.83 (q, J=8.7 Hz, 1 H), 7.62 (m, 2 H), 7.41 (m, 2 H), 7.22 (t, J=6.9 Hz, 1 H), 6.46 (s, 2 H), 4.51 (t, J=6.9 Hz, 2 H), 3.49 (t, J=7.5 Hz, 2H), 2.87 (t, J=7.5 Hz,2 H), 1.90(m, 2 H), 1.77 (m,4H), 1.43 (sextet, J=7.5 Hz, 2 H), 0.95 (t, J=7.5 Hz, 3 H); MS (CI) m/e 473 (M+H)

EXAMPLES 39–42

The thioethers shown in the table below were prepared by reacting 2-butyl-1-(4-chlorobutyl)-1H-imidazo[4,5-c] quinoline-4-amine with the appropriate thiol using the method of Example 37 Part D. The sulfones were prepared by oxidizing the appropriate thioether using the method of Example 38.

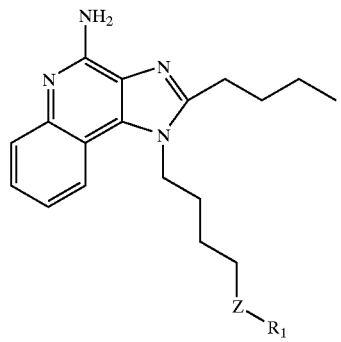

| Example | Z | $R_1$ | m.p. (° C.) | Elemental Analysis |
|---|---|---|---|---|
| 39 | $SO_2$ | ethyl | 141–143 | Calc'd for $C_{20}H_{28}N_4O_2S \cdot 0.18$ EtOH<br>% C, 61.63; % H, 7.39; % N, 14.12<br>Fd: % C, 61.73; % H, 7.14; % N, 14.48 |
| 40 | S | 1,1-dimethylethyl | 185–187 | Calc'd for $C_{22}H_{32}N_4S$<br>% C, 68.71; % H, 8.39; % N, 14.57<br>Fd: % C, 68.82; % H, 8.31; % N, 14.76 |
| 41 | S | 4-fluorophenyl | 122–125 | Calc'd for $C_{24}H_{27}FN_4S \cdot 0.5$ EtOH<br>% C, 68.22; % H, 6.44; % N 13.26<br>Fd: % C, 68.32; % H, 6.53; % N, 13.32 |
| 42 | $SO_2$ | 4-fluorophenyl | 173–174 | Calc'd for $C_{24}H_{27}FN_4O_2S \cdot 0.04$ EtOH<br>% C, 63.37; % H, 6.02; % N 12.28<br>Fd: % C, 63.58; % H, 5.95; % N, 12.68 |

NMR and mass spectroscopy data are given in the table below.

| Example | Mass Spectroscopy | NMR |
|---|---|---|
| 39 | MS(CI) m/e 389 (M + H) | $^1$H NMR(300MHz, DMSO-$d_6$) δ 8.05(d, J=8.1Hz, 1 H), 7.62(d, J=6.9Hz, 1H), 7.42(t, J=8.1Hz, 1H), 7.25(t, J=6.9Hz, 1H), 6.46(s, 2H), 4.56(t, J=7.5Hz, 2H), 3.17(t, J=7.5Hz, 2H), 3.07(q, J=7.5Hz, 2 H), 2.93(t, J=7.5Hz, 2H), 1.85(m, 6H), 1.46(sextet, J=7.5Hz, 2H), 1.20(t, J=7.5Hz, 3H), 0.96(t, J=7.5Hz, 3H); |
| 40 | MS(CI) m/e 385 (M + H) | $^1$H NMR(300MHz, DMSO-$d_6$) δ 8.05(d, J=7.2Hz, 1 H), 7.61(d, J=7.5Hz, 1H), 7.41(t, J=6.6Hz, 1H), 7.24(t, J=6.9Hz, 1H), 6.44(s, 2H), 4.51(t, J=7.5Hz, 2H), 2.92(t, J=7.5Hz, 2H), 2.57(t, J=6.6Hz, 2 H), 1.90(m, 2H), 1.80(m, 2H), 1.65(quintet, J=8.4Hz, 2H), 1.45(sextet, J=7.5Hz, 2H), 1.24(s, 9H), 0.96(t, J=6.6Hz, 3H); |
| 41 | MS(CI) m/e 423 (M + H) | $^1$H NMR(300MHz, DMSO-$d_6$) δ 8.02(d, J=7.5Hz, 1 H), 7.62(d, J=6.9Hz, 1H), 7.41(t, J=7.2Hz, 1H), 7.31(m, 2H), 7.22(t, J=6.6Hz, 1H), 7.13(m, 2H), 6.44(s, 2H), 4.51(t, J=7.5Hz, 2H), 2.98(t, J=6.6Hz, 2H), 2.87(t, J=7.5Hz, 2H), 1.92(quintet, J=6.6Hz, 2H), 1.72(m, 4H), 1.42(sextet, J=7.2Hz, 2H), 0.94(t, J=6.9Hz, 3H); |
| 42 | MS(CI) m/e 455 (M + H) | $^1$H NMR(300MHz, DMSO-$d_6$) δ 8.00(d, J=8.1Hz, 1 H), 7.88(m, 2H), 7.61(m, 1H), 7.46(m, 3H), 7.22(t, J=6.9Hz, 1H), 6.45(s, 2H), 4.51(t, J=6.9Hz, 2H), 3.41(t, J=7.8Hz, 2H), 2.86(t, J=7.2Hz, 2H), 1.77 (m, 6H), 1.43(sextet, J=8.1Hz, 2H), 0.94(t, J=7.5Hz, 3H); |

EXAMPLES 43–55

Part A

Using the general method of Example 1 Part D, $N^4$-(4-chlorobutyl)quinoline-3,4-diamine (30 g, 0.12 mole) was cyclized using trimethyl orthopropionate (23.3 g, 0.13 mol) in the presence of a catalytic amount of pyridine hydrochloride to provide 25.1 g of 1-(4-chlorobutyl)-2-ethyl-1H-imidazo[4,5-c]quinoline as solid.

Part B

3-Chloroperbenzoic acid (20.1 g of 60%, 0.117 mole) was added in portions to a solution of 1-(4-chlorobutyl)-2-ethyl-1H-imidazo[4,5-c]quinoline (24 g, 0.084 mol) in dichloromethane. The reaction mixture was diluted with enough 5% sodium carbonate to maintain the aqueous layer at pH 9–10. The layers were separated. The organic layer was washed sequentially with additional sodium carbonate, water (250 mL) and brine and then concentrated under reduced pressure. The resulting residue was dissolved in chloroform (350 mL). Ammonium hydroxide (250 mL) was added with vigorous stirring to form an emulsion. Tosyl chloride (19.2 g, 0.10 mol) was added in portions with stirring. The reaction mixture was washed with water (2×100 mL), 5% sodium carbonate (2×200 mL), and brine; dried over sodium carbonate and then concentrated under reduced pressure. The residue was combined with diethyl ether and stirred overnight. The resulting solid was isolated by filtration and air dried to provide 19.3 g of 1-(4-chlorobutyl)-2-ethyl-1H-imidazo[4,5-c]quinoline-4-amine.

Part C

The thioethers shown in the table below were prepared by reacting 1-(4-chlorobutyl)-2-ethyl-1H-imidazo[4,5-c]quinoline-4-amine with the appropriate thiol using the method of Example 37 Part D. The sulfones were prepared by oxidizing the appropriate thioether using the method of Example 38.

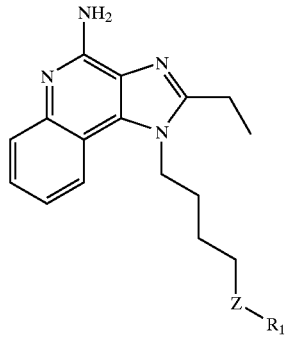

| Example | Z | $R_1$ | m.p. (° C.) | Elemental Analysis |
|---|---|---|---|---|
| 43 | S | 1-methylethyl | 138–142 | Calc'd for: $C_{19}H_{26}N_4S$<br>% C, 66.63; % H, 7.65; % N, 16.36<br>Fd: % C, 66.92; % H, 7.64; % N, 16.46 |
| 44 | S | 3,5-dichlorophenyl | 172–175 | Calc'd for: $C_{22}H_{22}Cl_2N_4S$:<br>% C, 59.33; % H, 4.98: % N, 12.58<br>Fd: % C, 59.21; % H, 4.97; % N, 12.56 |
| 45 | $SO_2$ | cyclopentyl | 163 (dec.) | Calc'd for: $C_{21}H_{28}N_4O_2S$<br>% C, 62.97; % H, 7.05; % N, 13.99<br>Fd: % C, 62.83; % H, 6.91; % N, 14.02 |
| 46 | $SO_2$ | 3,5-dichlorophenyl | 199–202 | Calc'd for: $C_{22}H_{22}Cl_2N_4O_2S \cdot 0.04$ EtOH<br>% C, 55.34; % H, 4.68: % N, 11.69<br>Fd: % C, 55.44; % H, 4.81; % N,[]11.74 |
| 47 | S | cyclohexyl | 139–143 | Calc'd for: $C_{22}H_{30}N_4S$<br>% C, 69.07; % H, 7.90; % N, 14.64<br>Fd: % C, 68.88; % H, 7.83; % N, 14.42 |
| 48 | S | butyl | 122 (dec.) | Calc'd for: $C_{20}H_{28}N_4S \cdot 0.40$ $H_2O$<br>% C, 66.04; % H, 7.98; % N, 15.40<br>Fd: % C, 66.10; % H, 7.91; % N, 15.16 |
| 49 | S | 4-chlorophenyl | 163–166 | Calc'd for: $C_{22}H_{23}ClN_4S \cdot 0.25$ EtOH<br>% C, 63.97; % H, 5.85; % N, 13.26<br>Fd: % C, 63.75; % H, 5.70; % N, 13.29 |
| 50 | $SO_2$ | butyl | 164–168 | Calc'd for: $C_{20}H_{28}N_4O_2S \cdot 0.05$ $CH_2Cl_2$<br>% C, 61.31; % H, 7.21; % N, 14.26<br>Fd: % C, 61.34; % H, 7.25; % N, 14.01 |
| 51 | S | 4-fluorophenyl | 156 (dec.) | Calc'd for: $C_{22}H_{23}FN_4S$<br>% C, 66.98; % H, 5.88; % N, 14.20<br>Fd: % C, 66.61; % H, 5.84; % N, 14.17 |
| 52 | $SO_2$ | 1-methylethyl | 200–202 | Calc'd for: $C_{19}H_{26}N_4O_2S \cdot 0.21$ $CH_3CN$<br>% C, 60.88; % H, 7.01; % N, 15.39<br>Fd: % C, 60.61; % H, 7.24; % N, 15.04 |
| 53 | S | ethyl | 141–143 | Calc'd for: $C_{18}H_{24}N_4S$<br>% C, 65.82; % H, 7.36; % N, 17.06<br>Fd: % C, 65.54; % H, 7.22; % N, 16.86 |
| 54 | $SO_2$ | ethyl | 170–174 | Calc'd for: $C_{18}H_{24}N_4O_2S \cdot 0.21$ $CH_3CN$<br>% C, 59.94; % H, 6.73; % N, 15.98<br>Fd: % C, 59.93; % H, 6.87; % N, 15.71 |

-continued

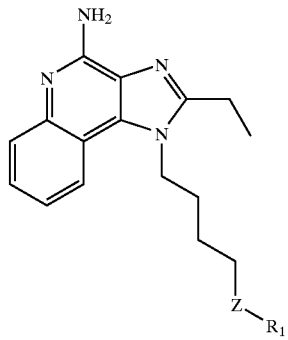

| Example | Z | R₁ | m.p. (° C.) | Elemental Analysis |
|---|---|---|---|---|
| 55 | SO₂ | cyclohexyl | 203–205 | Calc'd for: $C_{22}H_{30}N_4O_2S$<br>% C, 63.74; % H, 7.29; % N, 13.51<br>Fd: % C, 63.42; % H, 7.25; % N, 13.86 |

NMR and mass spectroscopy data are shown in the table below.

| Example | Mass Spectroscopy | NMR |
|---|---|---|
| 43 | MS(CI) m/e 343 (M + H) | $^1$H NMR(300MHz, DMSO-$d_6$) δ 8.05(d, J=8.1Hz, 1 H), 7.61(d, J=6.6Hz, 1H), 7.41(t, J=7.8Hz, 1H), 7.24(t, J=6.9Hz, 1H), 6.45(s, 2H), 4.51(t, J=7.5Hz, 2H), 2.93(m, 3H), 2.56(t, J=7.8Hz, 2H), 1.89 (quintet, J=8.4Hz, 2H), 1.66(quintet, J=7.5Hz, 2H), 1.37(t, J=7.5Hz, 3H), 1.16(d, 6H, J=6.7Hz); |
| 44 | MS(CI) m/e 445 (M + H) | $^1$H NMR(300MHz, DMSO-$d_6$) δ 8.02(d, J=7.2Hz, 1 H), 7.63(d, J=7.8Hz, 1H), 7.40(t, J=6.9Hz, 1H), 7.34(t, J=1.8Hz, 1H), 7.32(d, J=1.8Hz, 2H), 7.21(t, J=7.2Hz, 1H), 6.26(s, 2H), 4.51(t, J=7.5Hz, 2H), 3.12(t, J=7.2Hz, 2H), 2.92(q, J=7.2Hz, 2H), 1.94 (quintet, J=8.4Hz, 2H), 1.75(quintet, J=7.2Hz, 2H), 1.37(t, J=7.5Hz, 3H); |
| 45 | MS(CI) m/e 401 (M + H) | $^1$H NMR(300MHz, DMSO-$d_6$) δ 8.06(d, J=7.2Hz, 1 H), 7.62(d, J=7.2Hz, 1H), 7.41(t, J=6.9Hz, 1H), 7.25(t, J=6.9Hz, 1H), 6.48(s, 2H), 4.55(t, J=6.6Hz, 2H), 3.51(quintet, J=8.4Hz, 1H), 3.13(t, J=7.8Hz, 2 H), 2.96(q, J=7.5Hz, 2H), 1.87(m, 8H), 1.61(m, 4 H), 1.37(t, J=7.5Hz, 3H); |
| 46 | MS(CI) m/e 477 (M + H) | $^1$H NMR(300MHz, DMSO-$d_6$) δ 8.08(t, J=1.8Hz, 1 H), 8.01(d, J=7.2Hz, 1H), 7.89(d, J=1.8Hz, 2H), 7.61(dd, J=8.4; 1.2Hz, 1H), 7.41(t, J=7.2Hz, 1H), 7.22(t, J=7.2Hz, 1H), 6.45(s, 2H), 4.52(t, J=6.9Hz, 2H), 3.57(t, J=7.5Hz, 2H), 2.90(q, J=7.5Hz, 2H), 1.88(m, 2H), 1.73(m, 2H), 1.35(t, J=6.9Hz, 3H); |
| 47 | MS(CI) m/e 383 (M + H) | $^1$H NMR(300MHz, DMSO-$d_6$) δ 8.06(d, J=7.5Hz, 1 H), 7.62(d, J=6.9Hz, 1H), 7.41(t, J=6.9Hz, 1H), 7.23(t, J=6.9Hz, 1H), 6.46(s, 2H), 4.51(t, J=7.2Hz, 2H), 2.94(q, J=7.5Hz, 2H), 2.55(m, 2H), 1.84(m, 4 H), 1.66(m, 5H), 1.37(t, J=6.9Hz, 3H), 1.19(m, 6H); |
| 48 | MS(CI) m/e 357 (M + H) | $^1$H NMR(300MHz, DMSO-$d_6$) δ 8.05(d, J=6.9Hz, 1 H), 7.62(d, J=6.6Hz, 1H), 7.41(t, J=6.9Hz, 1H), 7.24(t, J=7.5Hz, 1H), 6.46(s, 2H), 4.51(t, J=7.2Hz, 2H), 2.95(q, J=7.2Hz, 2H), 2.56(m, 2H), 2.44(t, J=6.6Hz, 2H), 1.89(quintet, J=7.5Hz, 2H), 1.66 (quintet, J=7.5Hz, 2H), 1.37(m, 7H), 0.84(t, J=7.8Hz, 3H); |
| 49 | MS(CI) m/e 411 (M + H) | $^1$H NMR(300MHz, DMSO-$d_6$) δ 8.02(d, J=7.5Hz, 1 H), 7.63(d, J=7.2Hz, 1H), 7.41(t, J=7.5Hz, 1H), 7.31(m, 4H), 7.22(t, J=6.9Hz, 1H), 6.48(s, 2H), 4.50 (t, J=7.5Hz, 2H), 3.02(t, J=6.9Hz, 2H), 2.91(q, J=7.5Hz, 2H), 1.93(quintet, J=6.9Hz, 2H), 1.69 (quintet, J=7.8Hz, 2H), 1.35(t, J=7.5Hz, 3H); |

| Example | Mass Spectroscopy | NMR |
|---|---|---|
| 50 | MS(CI) m/e 389 (M + H) | ¹H NMR(300MHz, DMSO-d₆) δ 8.06(d, J=7.8Hz, 1 H), 7.62(d, J=7.8Hz, 1H), 7.41(t, J=7.8Hz, 1H), 7.25(t, J=6.9Hz, 1H), 6.48(s, 2H), 4.55(t, J=6.9Hz, 2H), 3.16(t, J=8.1Hz, 2H), 3.05(m, 2H), 2.96(q, J=7.5Hz, 2H), 1.89(m, 4H), 1.63(m, 2H), 1.42(m, 2H), 1.35(t, J=7.5Hz, 3H), 0.88(t, J=7.5Hz, 3H); |
| 51 | MS(CI) m/e 395 (M + H) | ¹H NMR(300MHz, DMSO-d₆) δ 8.02(d, J=7.5Hz, 1 H), 7.63(d, J=6.9Hz, 1H), 7.42(t, J=6.9Hz, 1H), 7.31(m, 2H), 7.22(t, J=6.6Hz, 1H), 7.13(m, 2H), 6.49(s, 2H), 4.50(t, J=7.5Hz, 2H), 2.98(t, J=6.9Hz, 2H), 2.91(q, J=7.5Hz, 2H), 1.92(quintet, J=7.5Hz, 2 H), 1.65(quintet, J=8.1Hz, 2H), 1.35(t, J=7.5Hz, 3 H); |
| 52 | MS(CI) m/e 375 (M + H) | ¹H NMR(300MHz, DMSO-d₆) δ 8.06(d, J=8.1Hz, 1 H), 7.63(d, J=7.5Hz, 1H), 7.42(t, J=6.9Hz, 1H), 7.23(t, J=6.9Hz, 1H), 6.51(s, 2H), 4.56(t, J=6.6Hz, 2H), 3.22(q, J=6.9Hz, 1H), 3.14(t, J=6.9Hz, 2H), 2.96(q, J=7.5Hz, 2H), 1.90(m, 4H), 1.38(t, J=7.5Hz, 3H), 1.22(d, 6H, J=6.9Hz); |
| 53 | MS(CI) m/e 329 (M + H) | ¹H NMR(300MHz, DMSO-d₆) δ 8.05(d, J=8.1Hz, 1 H), 7.62(d, J=6.9Hz, 1H), 7.41(t, J=7.5Hz, 1H), 7.24(t, J=6.9Hz, 1H), 6.48(s, 2H), 4.51(t, J=7.5Hz, 2H), 2.94(q, J=7.5Hz, 2H), 2.55(t, J 7.2Hz, 2H), 2.47(q, J=7.5Hz, 2H), 1.89(quintet, J=8.1Hz, 2H), 1.67(quintet, J=7.5Hz, 2H), 1.37(t, J=7.5Hz, 3H), 1.14(t, J=7.5Hz, 3H); |
| 54 | MS(CI) m/e 361 (M + H) | ¹H NMR(300MHz, DMSO-d₆) δ 8.05(d, J=8.1Hz, 1 H), 7.62(d, J=7.5Hz, 1H), 7.41(t, J=6.6Hz, 1H), 7.25(t, J=7.5Hz, 1H), 6.48(s, 2H), 4.55(t, J=6.9Hz, 2H), 3.16(t, J=7.8Hz, 2H), 3.06(q, J=7.2Hz, 2H), 2.96(q, J=6.9Hz, 2H), 1.90(m, 4H), 1.38(t, J=7.5Hz, 3H), 1.20(t, J=7.5Hz, 3H); |
| 55 | MS(CI) m/e 415 (M + H) | ¹H NMR(300MHz, DMSO-d₆) δ 8.06(d, J=7.5Hz, 1 H), 7.62(d, J=7.2Hz, 1H), 7.41(t, J=6.9Hz, 1H), 7.25(t, J=6.9Hz, 1H), 6.46(s, 2H), 4.55(t, J=6.6Hz, 2H), 3.11(t, J=7.8Hz, 2H), 2.97(m, 3H), 1.99(m, 8 H), 1.64(d, J=11.7Hz, 1H), 1.37(t, J=7.5Hz, 4H), 1.27(m, 4H); |

EXAMPLES 56–66

Part A

Thionyl chloride (3.8 g, 32 mmol) was added to a solution of 2-butyl-1-(2-hydroxyethyl)-1H-imidazo[4,5-c]quinolin-4-amine (3.7 g, 13 mmol) in toluene containing a catalytic amount of N,N-dimethylformamide. The reaction mixture was heated to reflux and then capped. When analysis by high performance liquid chromatography indicated that the reaction was complete, the reaction mixture was concentrated under reduced pressure. The residue was dissolved in warm methanol and then combined with concentrated ammonium hydroxide (5 mL). The mixture was chilled. The resulting precipitate was isolated by filtration, washed with cold methanol and then dried under vacuum overnight to provide 3.01 g of 2-butyl-1-(2-chloroethyl)-1H-imidazo[4,5-c]quinolin-4-amine as a brown solid.

Part B

The thioethers shown in the table below were prepared by reacting 2-butyl-1-(2-chloroethyl)-1H-imidazo[4,5-c]quinoline-4-amine with the appropriate thiol using the method of Example 37 Part D. The sulfones were prepared by oxidizing the appropriate thioether using the method of Example 38.

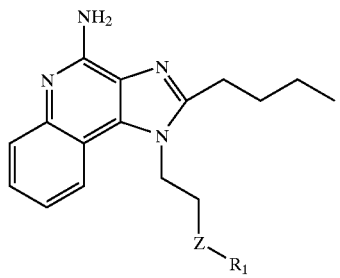

| Example | Z | R₁ | m.p. (° C.) | Elemental Analysis |
|---|---|---|---|---|
| 56 | SO$_2$ | 1-methylethyl | 177–179 | Calc'd for: C$_{19}$H$_{26}$N$_4$O$_2$S · 1.0 EtOH<br>% C, 60.94; % H, 7.00; % N, 14.96<br>Fd: % C, 60.97; % H, 6.93; % N, 15.11 |
| 57 | SO$_2$ | phenyl | 223–225 | Calc'd for: C$_{22}$H$_{24}$N$_4$O$_2$S<br>% C, 64.68; % H, 5.92; % N, 13.71<br>Fd: % C, 64.65; % H, 5.91; % N, 13.72 |
| 58 | SO$_2$ | 4-fluorophenyl | 244–247 | Calc'd for: C$_{22}$H$_{23}$FN$_4$O$_2$S<br>% C, 61.95; % H, 5.44; % N, 13.14<br>Fd: % C, 61.94; % H, 5.34; % N, 13.16 |
| 59 | S | 1,1-dimethylethyl | 159–160 | Calc'd for: C$_{20}$H$_{28}$N$_4$S<br>% C, 67.38; % H, 7.92; % N, 15.71<br>Fd: % C, 67.25; % H, 7.83; % N, 15.73 |
| 60 | SO$_2$ | 1,1-dimethylethyl | 201 (dec) | Calc'd for: C$_{20}$H$_{28}$N$_4$O$_2$S · 0.20 EtOH<br>% C, 61.60; % H, 7.40; % N, 14.09<br>Fd: % C, 61.86; % H, 7.34; % N, 14.16 |
| 61 | S | propyl | 117–119 | Calc'd for: C$_{19}$H$_{26}$N$_4$S<br>% C, 66.63; % H, 7.65; % N, 16.36<br>Fd: % C, 66.69; % H, 7.56; % N, 16.47 |
| 62 | SO$_2$ | propyl | 168–171 | Calc'd for: C$_{19}$H$_{26}$N$_4$O$_2$S<br>% C, 60.94; % H, 7.00; % N, 14.96<br>Fd: % C, 60.91; % H, 7.04; % N, 14.87 |
| 63 | S | 2-methylpropyl | 128–130 | Calc'd for: C$_{20}$H$_{28}$N$_4$S<br>% C, 67.38; % H, 7.92; % N, 15.71<br>Fd: % C, 67.58; % H, 7.75; % N, 15.84 |
| 64 | SO$_2$ | 2-methylpropyl | 170–171 | Calc'd for: C$_{20}$H$_{28}$N$_4$O$_2$S<br>% C, 61.83; % H, 7.26; % N, 14.42<br>Fd: % C, 61.92; % H, 7.19; % N, 14.53 |
| 65 | S | ethyl | 80–82 | Calc'd for: C$_{18}$H$_{24}$N$_4$S<br>% C, 65.82; % H, 7.36; % N, 17.06<br>Fd: % C, 65.67; % H, 7.07; % N, 17.03 |
| 66 | SO$_2$ | ethyl | 167–170 | Calc'd for: C$_{18}$H$_{24}$N$_4$O$_2$S<br>% C, 59.98; % H, 6.71; % N, 15.54<br>Fd: % C, 60.24; % H, 6.62; % N, 15.75 |

NMR and mass spectroscopy data are given in the table below.

| Example | Mass Spectroscopy | NMR |
|---|---|---|
| 56 | MS(CI) m/e 375 (M + H) | $^1$H NMR(300MHz, DMSO-d$_6$) δ 8.06(d, J=8.1Hz, 1 H), 7.64(d, J=8.1Hz, 1H), 7.43(t, J=6.9Hz, 1H), 7.25(t, J=6.9Hz, 1H), 6.49(s, 2H), 4.95(t, J=6.9Hz, 2H), 3.70(t, J=7.5Hz, 2H), 3.38(septet, J=6.9, 1H), 3.00(t, J=7.8Hz, 2H), 1.82(quintet, J=8.1Hz, 2H), 1.47(sextet, J=7.5Hz, 2H), 1.25(d, 6H, J=6.9Hz), 0.98(t, J=7.5Hz, 3H); |
| 57 | MS(CI) m/e 409 (M + H) | $^1$H NMR(300MHz, DMSO-d$_6$) δ 7.99(d, J=7.8Hz, 2 H), 7.83(t, J=7.5Hz, 1H), 7.71(t, J=7.5Hz, 2H), 7.59(d, J=9Hz, 2H), 7.38(t, J=7.5Hz, 1H), 7.05(t, J=6.9Hz, 1H), 6.46(s, 2H), 4.78(t, J=6.9Hz, 2H), 3.96(t, J=8.1Hz, 2H), 2.86(t, J=7.5Hz, 2H), 1.74 (quintet, J=7.5Hz, 2H), 1.41(sextet, J=7.5Hz, 2H), 0.94(t, J=6.9Hz, 3H); |
| 58 | MS(CI) m/e 427 (M + H) | $^1$H NMR(300MHz, DMSO-d$_6$) δ 8.02(m, 2H), 7.66 (d, J=6.9Hz, 1H), 7.57(m, 3H), 7.4(t, J=7.5Hz, 1 H), 7.09(t, J=6.9Hz, 1H), 6.45(s, 2H), 4.80(t, J=7.8Hz, 2H), 3.99(t, J=6.9Hz, 2H), 2.87(t, J=8.1Hz, |

-continued

| Example | Mass Spectroscopy | NMR |
|---|---|---|
| | | 2H), 1.75(quintet, J=7.5Hz, 2H), 1.39(sextet, J=7.5Hz, 2H), 0.94(t, J=7.5Hz, 3H); |
| 59 | MS(CI) m/e 357 (M + H) | $^1$H NMR(300MHz, DMSO-d$_6$) δ 8.19(d, J=9Hz, 1H), 7.82(d, J=7.5Hz, 1H), 7.62(t, J=6.9Hz, 1H), 7.45(t, J=6.9Hz, 1H), 6.69(s, 2H), 4.85(t, J=7.5Hz, 2H), 3.19(quintet, J=6.6Hz, 4H), 1.97(quintet, J=7.2Hz, 2H), 1.66(sextet, J=7.5Hz, 2H), 1.4(s, 9H), 1.16(t, J=7.8Hz, 3H); |
| 60 | MS(CI) m/e 389 (M + H) | $^1$H NMR(300MHz, DMSO-d$_6$) δ 8.06(d, J=8.1Hz, 1H), 7.65(d, J=7.8Hz, 1H), 7.43(t, J=6.9Hz, 1H), 7.24(t, J=6.9Hz, 1H), 6.51(s, 2H), 4.96(t, J=7.5Hz, 2H), 3.66(t, J=7.5Hz, 2H), 3.01(t, J=8.1Hz, 2H), 1.82(quintet, J=7.5Hz, 2H), 1.48(sextet, J=7.5Hz, 2H), 1.32(s, 9H), 0.97(t, J=7.2Hz, 3H); |
| 61 | MS(CI) m/e 343 (M + H) | $^1$H NMR(300MHz, DMSO-d$_6$) δ 7.99(d, J=7.8Hz, 1H), 7.62(d, J=7.5Hz, 1H), 7.41(t, J=7.8Hz, 1H), 7.24(t, J=6.6Hz, 1H), 6.46(s, 2H), 4.70(t, J=7.5Hz, 2H), 2.98(t, J=6.9Hz, 4H), 2.45(t, J=7.5Hz, 2H), 1.80(quintet, J=7.8Hz, 2H), 1.46(sextet, J=7.2Hz, 4H), 0.96(t, J=7.5Hz, 3H), 0.86(t, J=7.5Hz, 3H); |
| 62 | MS(CI) m/e 375 (M + H) | $^1$H NMR(300MHz, DMSO-d$_6$) δ 8.06(d, J=8.7Hz, 1H), 7.64(d, J=7.5Hz, 1H), 7.44(t, J=6.6Hz, 1H), 7.25(t, J=6.9Hz, 1H), 6.49(s, 2H), 4.95(t, J=7.5Hz, 2H), 3.72(t, J=7.2Hz, 2H), 3.18(m, 2H), 2.99(t, J=7.5Hz, 2H), 1.82(quintet, J=8.1Hz, 2H), 1.69(sextet, J=8.4Hz, 2H), 1.47(sextet, J=7.5Hz, 2H), 0.97(t, J=7.2Hz, 3H), 0.96(t, J=7.5Hz, 3H); |
| 63 | MS(CI) m/e 357 (M + H) | $^1$H NMR(300MHz, DMSO-d$_6$) δ 7.99(d, J=7.2Hz, 1H), 7.62(d, J=6.6Hz, 1H), 7.41(t, J=6.9Hz, 1H), 7.24(t, J=6.9Hz, 1H), 6.47(s, 2H), 4.70(t, J=6.9Hz, 2H), 2.97(t, J=8.4Hz, 4H), 2.35(d, J=6.6Hz, 2H), 1.81(quintet, J=7.5Hz, 2H), 1.63(septet, J=6.6Hz, 1H), 1.46(sextet, J=7.5Hz, 2H), 0.96(t, J=7.5Hz, 3H), 0.87(d, J=6.6Hz, 6H); |
| 64 | MS(CI) m/e 389 (M + H) | $^1$H NMR(300MHz, DMSO-d$_6$) δ 8.06(d, J=7.5Hz, 1H), 7.64(d, J=8.1Hz, 1H), 7.43(t, J=6.6Hz, 1H), 7.23(t, J=6.9Hz, 1H), 6.51(s, 2H), 4.94(t, J=6.6Hz, 2H), 3.72(t, J=7.8Hz, 2H), 3.13(d, J=6.6Hz, 2H), 2.99(t, J=7.5Hz, 2H), 2.21(septet, J=6Hz, 1H), 1.81(quintet, J=8.4Hz, 2H), 1.47(sextet, J=7.5Hz, 2H), 1.00(m, 9H); |
| 65 | MS(CI) m/e 329 (M + H) | $^1$H NMR(300MHz, DMSO-d$_6$) δ 8.00(d, J=8.4Hz, 1H), 7.62(d, J=8.4Hz, 1H), 7.42(t, J=8.4Hz, 1H), 7.25(t, J=8.4Hz, 1H), 6.47(s, 2H), 4.71(t, J=7.5Hz, 2H), 2.99(q, J=7.8Hz, 4H), 2.53(m, 2H), 1.81(quintet, J=7.8Hz, 2H), 1.46(sextet, J=7.2Hz, 2H), 1.12(t, J=7.2Hz, 3H), 0.97(t, J=7.2Hz, 3H); |
| 66 | MS(CI) m/e 361 (M + H) | $^1$H NMR(300MHz, DMSO-d$_6$) δ 8.06(d, J=6.9Hz, 1H), 7.63(d, J=6.9Hz, 1H), 7.43(t, J=6.9Hz, 1H), 7.25(t, J=6.9Hz, 1H), 6.48(s, 2H), 4.95(t, J=7.2Hz, 2H), 3.72(t, J=7.2Hz, 2H), 3.22(quartet, J=7.5, 2H), 2.99(t, J=7.5Hz, 2H), 1.81(quintet, J=7.2Hz, 2H), 1.44(sextet, J=6.9Hz, 2H), 1.21(t, J=7.5Hz, 3H), 0.97(t, J=7.5Hz, 3H); |

EXAMPLE 67

2-butyl-1-[2-(methylsulfonyl)ethyl]-1H-imidazo[4,5-c]quinolin-4-amine

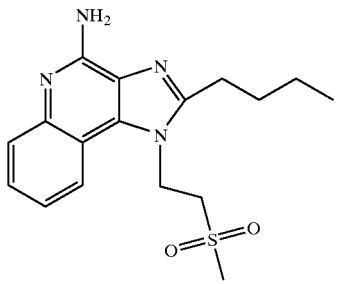

Part A

Using the general method of Example 21 Part D, 2-butyl-1-(2-chloroethyl)-1H-imidazo[4,5-c]quinoline-4-amine (1.44 g, 4.76 mmol) was reacted with sodium thiomethoxide (0.42 g of 95%, 5.71 mmol) to provide 1.4 g of 2-butyl-1-[2-(methylthio)ethyl]-1H-imidazo[4,5-c]quinolin-4-amine as an off-white powder.

Part B

Using the general method of Example 5, 2-butyl-1-[2-(methylthio)ethyl]-1H-imidazo[4,5-c]quinolin-4-amine (1.35 g, 4.29 mol) was oxidized. The crude product was purified by chromatography (silica gel eluting with 95/5 dichloromethane/methanol) then triturated with diethyl ether to provide 0.5 g of 2-butyl-1-[2-(methylsulfonyl)ethyl]-1H-imidazo[4,5-c]quinolin-4-amine as a white powder, m.p. 226–228° C.

Analysis: Calculated for $C_{17}H_{22}N_4O_2S$: % C, 58.94; % H, 6.40; % N, 16.17; Found: % C, 58.91; % H, 6.27; % N, 16.13. $^1$H NMR (300 MHz, DMSO-$d_6$) δ 8.05 (d, J=8.1 Hz, 1 H), 7.63 (d, J=8.1 Hz, 1 H), 7.44 (t, J=8.4, Hz, 1 H), 7.26 (t, J=8.1, Hz, 1 H), 6.48 (s, 2 H), 4.95 (t, J=7.2 Hz, 2 H), 3.77 (t, J=7.2 Hz, 2 H), 3.11 (s, 3 H), 2.99 (t, J=7.8 Hz, 2 H), 1.83 (quintet, J=7.6 Hz, 2 H), 1.48 (sextet, J=7.4 Hz, 2 H), 0.97 (t, J=7.5 Hz, 3 H); MS(CI) m/e 347 (M+H).

EXAMPLE 68

2-methyl-1-[6-(methylsulfonyl)hexyl]-1H-imidazo[4,5-c]quinolin-4-amine

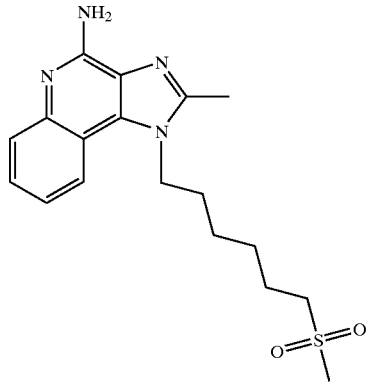

Part A

A solution of thionyl chloride (6.74 g, 56.6 mmol) in dichloromethane (50 mL) was slowly added to a solution of N-(6-hydroxyhexyl)-3-nitroquinolin-4-amine (14.9 g, 51.5 mmol) in dichloromethane (200 mL). After the addition was complete the reaction mixture was stirred for about an hour and then it was concentrated under reduced pressure. The residue was suspended in water, slurried for about an hour, isolated by filtration, washed with water and then dried to provide 14.0 g of N-(6-chlorohexyl)-3-nitroquinolin-4-amine as a solid.

Part B

Using the general method of Example 1 Part C, 4-(6-chlorohexyl)-3-nitroquinolin-4-amine (6 g, 19 mmol) was reduced to provide $N^4$-(6-chlorohexyl)quinoline-3,4-diamine.

Part C $N^4$-(6-Chlorohexyl)quinoline-3,4-diamine (5 g, 18 mmol), triethyl orthoacetate (2.92 g, 18 mmol), toluene (75 mL), and a catalytic amount of pyridine hydrochloride were combined in a pressure vessel and heated to 140° C. After about 1.5 hours the reaction mixture was allowed to cool and then it was concentrated under reduced pressure to provide 3.8 g of 1-(6-chlorohexyl)-2-methyl-1H-imidazo[4,5-c]quinoline as a dark orange oil.

Part D

Using the general method of Examples 43–55 Part B, 1-(6-chlorohexyl)-2-methyl-1H-imidazo[4,5-c]quinoline (3.8 g, 13 mol) was oxidized and then aminated to provide 2.5 g of 1-(6-chlorohexyl)-2-methyl-1H-imidazo[4,5-c]quinolin-4-amine.

Part E 1-(6-Chlorohexyl)-2-methyl-1H-imidazo[4,5-c]quinolin-4-amine (2.5 g, 8 mmol), sodium thiomethoxide (1.13 g, 15.5 mmol) and N,N-dimethylformamide (15 mL) were combined and heated at 160° C. for 3 hours. The reaction was quenched with water and the precipitate isolated to provide 1.5 g of 2-methyl-1-[6-(methylthio)hexyl]-1H-imidazo[4,5-c]quinolin-4-amine.

Part F

Using the general method of Example 38, the material from Part E was oxidized to provide 0.80 g of 2-methyl-1-[6-(methylsulfonyl)hexyl]-1H-imidazo[4,5-c]quinolin-4-amine, m.p. 202–206° C.

Analysis: Calculated for $C_{18}H_{24}N_4O_2S.0.02$ EtOH: % C, 59.96; % H, 6.73; % N, 15.50; Found: % C, 59.74; % H, 6.81; % N, 15.30. $^1$H NMR (300 MHz, DMSO-$d_6$) δ 8.02 (d, J=8.1 Hz, 1 H), 7.62 (d, J=7.2 Hz, 1 H), 7.41 (t, J=8.1 Hz, 1 H), 7.25 (t, J=7.2 Hz, 1 H), 6.48 (s, 2 H), 4.48 (t, J7.2 Hz, 2 H), 3.08 (t, J=8.4 Hz, 2 H), 2.92 (s, 3 H), 2.60 (s, 3 H), 1.82 (m, 2 H), 1.68 (m, 2 H) 1.44 (m, 4 H); MS (CI) m/e 361 (M+H).

EXAMPLE 69

1-[5-(phenylsulfonyl)pentyl]-1H-imidazo[4,5-c]quinolin-4-amine

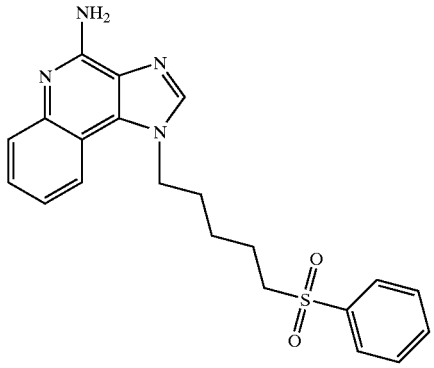

Part A

Using the general method of Example 37 Part D, N-(5-chloropentyl)-3-nitroquinolin-4-amine (10 g, 34 mmol) was reacted with benzenethiol (1.1 eq) to provide 12.6 g of 3-nitro-N-[5-(phenylthio)pentyl]quinolin-4-amine as a solid.

Part B

Using the general method of Example 1 Part C, the material from Part A was reduced to provide $N^4$-[5-(phenylthio)pentyl]quinoline-3,4-diamine as a brown crystalline solid.

Part C

Using the general method of Example 1 Part D, $N^4$-[5-(phenylthio)pentyl]quinoline-3,4-diamine (5.1 g, 15.1 mmol) was cyclized using triethyl orthoformate (2.46 g, 16.6 mmol) in the presence of a catalytic amount of pyridine hydrochloride to provide 1-[5-(phenylthio)pentyl]-1H-imidazo[4,5-c]quinoline as a yellow solid.

Part D

Using the general method of Example 11 Part F except that dichloromethane was used as a solvent instead of chloroform, 1-[5-(phenylthio)pentyl]-1H-imidazo[4,5-c]quinoline (5 g, 13.2 mmol) was oxidized to provide 4.7 g 1-[5-(phenylsulfonyl)pentyl]-1H-imidazo[4,5-c]quinoline 5N-oxide as an oil.

Part E

Trichloroacetyl isocyanate (1.91 g, 10 mmol) was added slowly to a solution of 1-[5-(phenylsulfonyl)pentyl]-1H-imidazo[4,5-c]quinoline 5N-oxide (3.6 g, 9.1 mmol) in dichloromethane (40 mL). The reaction mixture was concentrated under reduced pressure. The residue was dissolved in methanol then combined with about 2 equivalents of sodium methoxide. After several minutes a precipitate formed. The precipitate was isolated by filtration and then recrystallized from ethanol. This material was purified by chromatography (silica gel eluting with 4% methanol in dichloromethane) to provide 0.3 g of 1-[5-(phenylsulfonyl)pentyl]-1H-imidazo[4,5-c]quinoline-4-amine as a solid, m.p. 171–172° C.

Analysis: Calculated for $C_{21}H_{22}N_4O_2S$: % C, 63.94; % H, 5.62; % N, 14.20; Found: % C, 63.72; % H, 5.64; % N, 14.07. $^1$H NMR (300 MHz, DMSO-$d_6$) δ 8.15 (s, 1 H), 7.99(d, J=8.1 Hz, 1 H), 7.86 (m, 2 H), 7.71 (m, 1 H), 7.64 (m, 3 H), 7.43 (t, J=6.6 Hz, 1 H); 7.22 (t, J=6.9 Hz, 1 H), 6.57 (s, 2 H), 4.54 (t, J=7.5 Hz, 2 H), 3.30 (m, 2 H), 1.84 (quintet, J=7.5 Hz, 2 H), 1.57 (quintet, J=6.9 Hz, 2 H), 1.40 (quintet, J=6.9 Hz, 2 H); MS (CI) m/e 395 (M+H).

EXAMPLE 70

2-(2-methoxyethyl)-1-[5-(phenylsulfonyl)pentyl]-1H-imidazo[4,5-c]quinolin-4-amine

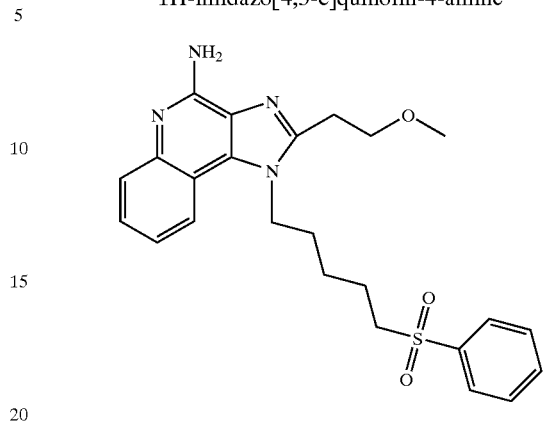

Part A

A solution of 3-methoxypropanoyl chloride (2.04 g, 16.6 mmol) in pyridine (20 mL) was slowly added to a chilled (0° C.) solution of $N^4$-[5-(phenylthio)pentyl]quinoline-3,4-diamine (5.1 g, 15.2 mmol) in pyridine. The reaction was allowed to warm to ambient temperature. More acid chloride (1 g) was added and the reaction was heated at reflux overnight. The reaction mixture was concentrated under reduced pressure to provide 6.7 g of 3-methoxy-N-(4-{[5-(phenylthio)pentyl]amino}quinolin-3-yl)propanamide as a sticky brown solid.

Part B

The material from Part A was combined with pyridine and then refluxed for several hours. The reaction mixture was concentrated under reduced pressure. The residue was partitioned between dichloromethane and water. The organic layer was washed with water (3×100 mL), filtered through a layer of Celite®D filter aid, and then concentrated under reduced pressure. The residue was purified by chromatography (silica gel eluting with 4/1 dichloromethane/methanol) to provide 3.7 g of 2-(2-methoxyethyl)-1-[5-(phenylsulfonyl)pentyl]-1H-imidazo[4,5-c]quinoline.

Part C

Using the general method of Example 37 Part B, the material from Part B was oxidized to provide 2.09 g of 2-(2-methoxyethyl)-1-[5-(phenylsulfonyl)pentyl]-1H-imidazo[4,5-c]quinoline-5N-oxide.

Part D

Using the general method of Example 37 Part C, the material from Part C was aminated. The crude product was recrystallized from ethanol to provide 0.26 g of 2-(2-methoxyethyl)-1-[5-(phenylsulfonyl)pentyl]-1H-imidazo[4,5-c]quinolin-4-amine, m.p. 172–175° C.

Analysis: Calculated for $C_{24}H_{28}N_4O_3S$: % C, 63.69; % H, 6.24; % N, 12.38; Found: % C, 63.40; % H, 5.95; % N, 12.08. $^1$H NMR (300 MHz, DMSO-$d_6$) δ 7.96 (d, J=6.6 Hz, 1 H), 7.87 (d, J=5.4 Hz, 2 H), 7.73 (m, 1 H), 7.63 (m, 3 H), 7.41 (t, J=7.8 Hz, 1 H), 7.22 (t, J=7.8 Hz, 1 H), 6.47 (s, 2 H), 4.46 (t, J=7.5Hz, 2 H), 3.80 (t, J=6.9Hz, 2 H), 3.27 (s, 3 H), 3.14 (t, J=6 Hz, 2 H), 1.76 (m, 2 H), 1.53 (m, 4 H); MS (CI) m/e 473 (M+H).

EXAMPLE 71

1-[5-(methylsulfonyl)pentyl]-2-(trifluoromethyl)-
1H-imidazo[4,5-c]quinolin-4-amine

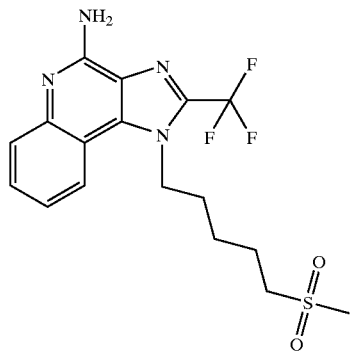

Part A

A cool solution of trifluoroacetyl chloride (3.5 g, 26.5 mmol) in toluene was slowly added to a solution of N4-[5-(methylthio)pentyl]quinoline-3,4-diamine (6 g, 23.1 mmol) in a mixture of toluene and pyridine. A heavy yellow precipitate formed. The reaction mixture was stirred over the weekend and then concentrated under reduced pressure to provide 13.2 g of crude 2,2,2-trifluoro-N-(4-{[5-(methylthio)pentyl]amino}quinolin-3-yl)acetamide.

Part B

The material from Part A was combined with toluene (150 mL) in a pressure vessel and then heated at 140° C. for about 30 minutes. The reaction mixture was concentrated under reduced pressure. The residue was partitioned between dichloromethane and 5% sodium carbonate. The organic layer was washed with water, dried over magnesium sulfate and then concentrated under reduced pressure to provide 7.9 g of 1-[5-(methylthio)pentyl]-2-(trifluoromethyl)-1H-imidazo[4,5-c]quinoline as a solid.

Part C

Using the general method of Example 11 Part F, the material from Part B was oxidized to provide 7.5 g of 1-[5-(methylsulfonyl)pentyl]-2-(trifluoromethyl)-1H-imidazo[4,5-c]quinoline-5N-oxide.

Part D

Using the general method of Example 37 Part C, the material from Part C was aminated to provide 2.5 g of 1-[5-(methylsulfonyl)pentyl]-2-(trifluoromethyl)-1H-imidazo[4,5-c]quinolin-4-amine as a solid, m.p. 192–195° C.

Analysis: Calculated for $C_{17}H_{19}F_3N_4O_2S$:.0.05 $CH_2Cl_2$: % C, 50.61; % H, 4.76; % N, 13.84; found: % C, 50.60; % H, 4.76; % N, 13.77. $^1$H NMR (300 MHz, DMSO-$d_6$) δ 8.08 (d, J=7.2 Hz, 1 H), 7.67 (d, J=7.5 Hz, 1 H), 7.54 (t, J=6.9 Hz, 1 H), 7.34 (t, J=7.8 Hz, 1 H), 6.91 (s, 2 H), 4.67 (t, J=8.4 Hz, 2 H), 3.11 (t, J=7.5 Hz, 2 H), 2.93 (s, 3 H), 1.91 (quintet, J=7.2 Hz, 2 H), 1.744 (quintet, J=8.1 Hz, 2 H), 1.58 (quintet, J=6.9 Hz, 2 H); MS (CI) m/e 401 (M+H).

EXAMPLE 72

2-ethyl-1-[4-(pyrimidin-2-ylthio)butyl]-1H-imidazo
[4,5-c]quinolin-4-amine

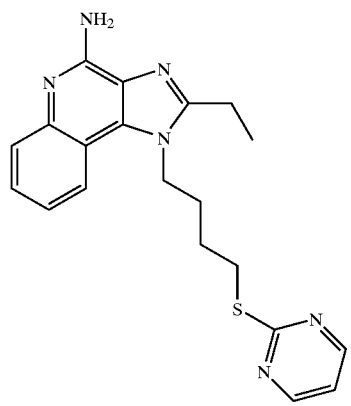

Using the general method of Example 20 Part A, 1-(4-chlorobutyl)-2-ethyl-1H-imidazo[4,5-c]quinolin-4-amine (1.0 g, 3.30 mmol) was reacted with 2-mercaptopyrimidine (0.59 g, 5.3 mmol) to provide 1.0 g of 2-ethyl-1-[4-(pyrimidin-2-ylthio)butyl]-1H-imidazo[4,5-c]quinolin-4-amine as an off white powder, m.p. 182–185° C.

Analysis: Calculated for $C_{20}H_{22}N_6S.0.25\ H_2O$: % C, 62.72; % H, 5.92; % N, 21.94; Found: % C, 63.00; % H, 5.88; % N, 22.21.

EXAMPLE 73

2-ethyl-1-[4-(pyrimidin-2-ylsulfonyl)butyl]-1H-
imidazo[4,5-c]quinolin-4-amine

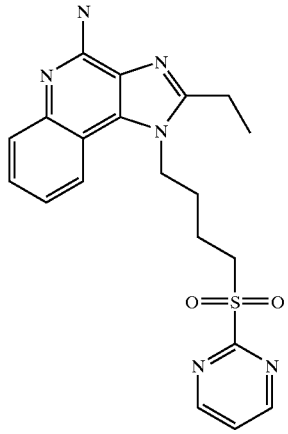

Using the general method of Example 5 Part A, 2-ethyl-1-[4-(pyrimidin-2-ylthio)butyl]-1H-imidazo[4,5-c]quinolin-4-amine (0.3 g) was oxidized to provide 10 mg of 2-ethyl-1-[4-(pyrimidin-2-ylsulfonyl)butyl]-1H-imidazo[4,5-c]quinolin-4-amine as a peach solid, m.p. 172–175° C.

Analysis: Calculated for $C_{20}H_{22}N_6O_2 \cdot 0.25\ H_2O$: % C, 57.88; % H, 5.46; % N, 20.25; Found: % C, 57.76; % H, 5.48; % N, 19.88.

EXAMPLE 74

2-methyl-1-[4-(methylsulfonyl)butyl]-6,7,8,9-tetrahydro-1H-imidazo[4,5-c]quinolin-4-amine

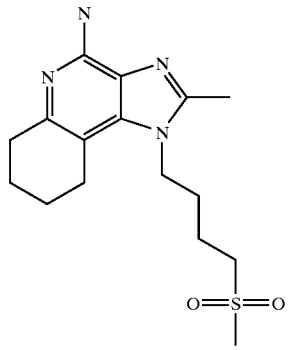

Catalyst (0.2 g of platinum oxide) was added to solution of 2-methyl-1-[4-(methylsulfonyl)butyl]-1H-imidazo[4,5-c]quinolin-4-amine (1.0 g) in trifluoroacetic acid (11 mL) in a Parr hydrogenation flask. The resulting mixture was placed under hydrogen pressure (50 psi, 3.5 Kg/cm$^2$) for about 90 hours. The reaction mixture was filtered through a layer of Celite® filter aid which had been prewashed with trifluoroacetic acid (~125 mL). The filter cake was washed with trifluoroacetic acid (~100 mL). The filtrate was concentrated under reduced pressure. The resulting oil was dissolved in 1 N hydrochloric acid (20 mL). After several minutes a white precipitate formed. The pH was brought to 14 with aqueous 50% sodium hydroxide. The precipitate dissolved to provide a yellow solution; shortly thereafter a precipitate formed. The resulting suspension was allowed to stir at ambient temperature overnight then it was cooled in an ice/water bath for 2 hours and then filtered to provide 1.0 g of a white powder. This material was purified by recrystallization from methanol followed by column chromatography (silica gel eluting with 9/1 dichloromethane/methanol) to provide 0.44 g of 2-methyl-1-[4-(methylsulfonyl)butyl]-6,7,8,9-tetrahydro-1H-imidazo[4,5-c]quinolin-4-amine as a white solid, m.p. 213–216° C.

Analysis: Calculated for $C_{16}H_{24}N_4O_2S$: % C, 57.12; % H, 7.19; % N, 16.65; Found: % C, 56.86; % H, 7.09; % N, 16.61.

EXAMPLE 75

2-methyl-1-[5-(methylsulfonyl)pentyl]-6,7,8,9-tetrahydro-1H-imidazo[4,5-c]quinolin-4-amine

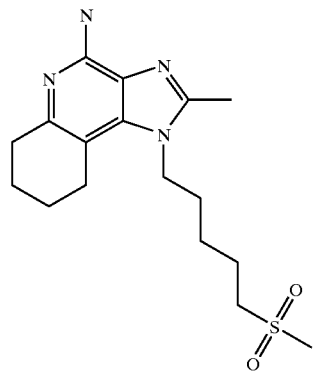

Using the general method of Example 74, 2-methyl-1-[4-(methylsulfonyl)pentyl]-1H-imidazo[4,5-c]quinolin-4-amine (1.3 g) was reduced and purified to provide 0.6 g of 2-methyl-1-[5-(methylsulfonyl)pentyl]-6,7,8,9-tetrahydro-1H-imidazo[4,5-c]quinolin-4-amine as white needles, m.p. 172–174° C.

Analysis: Calculated for $C_{17}H_{26}N_4O_2S$: % C, 58.26; % H, 7.48; % N, 15.99; Found: % C, 58.22; % H, 7.54; % N, 16.12.

EXAMPLE 76

2-methyl-1-{4-[(1-methylethyl)sulfonyl]butyl}-6,7,8,9-tetrahydro-1H-imidazo[4,5-c]quinolin-4-amine

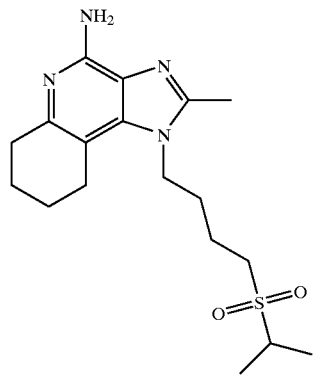

Part A

A suspension of 2,4-dihydroxy-3-nitro-6,7,8,9-tetrahydroquinoline (10.56 g, 50.3 mmol) in phosphorous oxychloride (60 mL) was heated at 50–60° C. for 48 hours. The reaction mixture was allowed to cool to ambient temperature then it was slowly added with vigorous stirring to an ice cooled biphasic mixture of dichloromethane (300 mL) and aqueous 20% sodium carbonate (500 mL). The mixture was made basic (pH 8) with solid sodium carbonate and the layers were separated. The aqueous layer was extracted with dichloromethane (2×125 mL). The combined organics were dried over magnesium sulfate and then concentrated under reduced pressure to provide 11.9 g of 2,4-dichloro-3-nitro-6,7,8,9-tetrahydroquinoline as a light brown solid.

Part B

Triethylamine (6.1 mL, 1.2 eq) was added to a solution of 2,4-dichloro-3-nitro-6,7,8,9-tetrahydroquinoline (9.0 g, 36.4 mmol, 1 eq) in N,N-dimethylformamide (60 mL). 4-Amino-1-butanol (3.7 mL, 1.1 eq) was added and the reaction mixture was heated at ~50° C. for 5 hours. The reaction mixture was allowed to cool to ambient temperature and then it was concentrated under reduced pressure to provide a red oil. The oil was diluted with chloroform (500 mL), washed with water (3×200 mL) and brine (1×200 mL) then dried over magnesium sulfate and concentrated under reduced pressure to provide 11.9 g of a red oil. The oil was triturated with diethyl ether (40 mL). The resulting solid was isolated by filtration then washed with diethyl ether (3×10 mL) to provide 5.76 g of 4-[(2-chloro-3-nitro-6,7,8,9-tetrahydroquinolin-4-yl)amino]butan-1-ol as a light yellow solid.

Part C

Phenol (2.71 g, 1.5 eq) was added in portions over a period of 15 minutes to a suspension of sodium hydride (1.15 g of 60%, 1.5 eq) in diglyme (34 mL). The reaction mixture was stirred for an additional 30 minutes and then 4-[(2-chloro-3-nitro-6,7,8,9-tetrahydroquinolin-4-yl)amino]butan-1-ol (5.75 g, 19.16 mmol, 1.0 eq) was added as a solid. The reaction mixture was heated at 85° C. for 24 hours and then allowed to cool to ambient temperature overnight. The reaction mixture was concentrated to a volume of ~10 mL under reduced pressure. The concentrate was diluted with chloroform (400 mL), washed with aqueous 5% sodium hydroxide (1×75 mL) and water (2×100 mL) then dried over magnesium sulfate and concentrated under reduced pressure. The residue was dissolved in acetonitrile (200 mL), washed with hexanes (2×100 mL) and concentrated under reduced pressure to provide 5.31 g of 4-[(3-nitro-2-phenoxy-6,7,8,9-tetrahydroquinolin-4-yl)amino]butan-1-ol as a dark oil.

Part D

N-Chlorosuccinimide (2.38 g, 1.2 eq) was added to a solution of triphenylphosphine (4.68 g, 1.2 eq) in tetrahydrofuran (30 mL). The reaction mixture was stirred for 20 minutes and then a solution of the material from Part C in tetrahydrofuran (30 mL) was added. The reaction mixture was stirred for 75 minutes and then concentrated under reduced pressure. The residue was diluted with chloroform (350 mL), washed with water (2×150 mL), dried over magnesium sulfate and then concentrated under reduced pressure. The residue was purified by chromatography (silica gel eluting with chloroform) to provide 4.88 g of N4-(4-chlorobutyl)-3-nitro-2-phenoxy-6,7,8,9-tetrahydroquinolin-4-amine as a yellow solid.

Part E

Nickel(II)chloride hexahydrate (303 mg, 0.1 eq) was added to a suspension of $N^4$-(4-chlorobutyl)-3-nitro-2-phenoxy-6,7,8,9-tetrahydroquinolin-4-amine (4.78 g, 12.71 mmol, 1.0 eq) in 1:1 methanol:chloroform (120mL). The mixture was cooled to 0° C. Sodium borohydride (1.92 g, 4 eq) was added in 4 equal portions over a period of 50 minutes. The reaction mixture was stirred for an additional 30 minutes and then it was concentrated under reduced pressure. The residue was dissolved in chloroform (300 mL), washed with water (3×100 mL), dried over magnesium sulfate and then concentrated under reduced pressure to provide 5.01 g of $N^4$-(4-chlorobutyl)-2-phenoxy-6,7,8,9-tetrahydroquinoline-3,4-diamine as a thick oil.

Part F

Trimethylorthoacetate (2.0 mL, 1.2 eq) was added to a solution of the material from Part E in toluene (40 mL). Pyridine hydrochloride (150 mg, 0.1 eq) was added and the reaction mixture was heated at 100° C. for 1 hour. The reaction mixture was cooled to ambient temperature and then concentrated under reduced pressure. The residue was dissolved in chloroform (300 mL), washed with water (2×75 mL), dried over magnesium sulfate, concentrated under reduced pressure, diluted with acetonitrile (40 mL) and then concentrated under reduced pressure to provide 4.5 g of a dark red semisolid. This material was purified on silica eluting with 2:98 methanol:chloroform to provide a red oil. The oil was diluted with isopropanol (50 mL), concentrated and then triturated with diethyl ether. The resulting solid was isolated by filtration and washed with diethyl ether to provide 2.77 g of 1-(4-chlorobutyl)-2-methyl-4-phenoxy-6,7,8,9-tetrahydro-1H-imidazo[4,5-c]quinoline as a white solid.

Part G

1-Methylethylthiol (57 μL, 1.2 eq) was added dropwise to a suspension of sodium hydride (25 mg of 60%, 1.2 eq) in N,N-dimethylformamide (1 mL). The reaction mixture was stirred for 30 minutes and then a solution of 1-(4-chlorobutyl)-2-methyl-4-phenoxy-6,7,8,9-tetrahydro-1H-imidazo[4,5-c]quinoline (189 mg, 0.51 mmol, 1.0 eq) in N,N-dimethylformamide (1.5 mL) was added. The reaction mixture was stirred for 3 hours then it was diluted with chloroform (50 mL), washed with aqueous 5% sodium hydroxide (1×50 mL) and water (1×25 mL), dried over magnesium sulfate and then concentrated under reduced pressure to provide 176 mg of 1-{[4-(1-methylethyl)thio]butyl}-2-methyl-4-phenoxy-6,7,8,9-tetrahydro-1H-imidazo[4,5-c]quinoline as a light brown oil.

Part H

3-Chloroperbenzoic acid (218 mg, 2.2 eq at 75% titer) was added to a chilled (0° C.) solution of the material from Part G in chloroform (2.2 mL). The reaction mixture was stirred at 0° C. for 20 minutes and then it was diluted with chloroform (50 mL), washed with aqueous saturated sodium carbonate (2×25 mL), dried over magnesium sulfate and then concentrated under reduced pressure to provide 202 mg of 1-{[4-(1-methylethyl)sulfonyl]butyl}-2-methyl-4-phenoxy-6,7,8,9-tetrahydro-1H-imidazo[4,5-c]quinoline as a yellow semisolid.

Part I

A mixture of 1-{[-(1-methylethyl)sulfonyl]butyl}-2-methyl-4-phenoxy-6,7,8,9-tetrahydro-1H-imidazo[4,5-c]quinoline (200 mg) and solid ammonium acetate (2.1 g) were heated at 145° C. in a sealed tube for 24 hours. The reaction was cooled to ambient temperature then it was diluted with chloroform (40 mL) and washed with aqueous 10% sodium hydroxide (2×20 mL). The aqueous layer was extracted with chloroform (2×20 mL). The combined organics were dried over magnesium sulfate and then concentrated under reduced pressure to provide 204 mg of a yellow oil. The oil was triturated with acetonitrile to provide 48 mg of an off white solid. The mother liquor was concentrated and the residue purified by chromatography (silica gel eluting with 10:90 methanol:chloroform) followed by trituration with acetonitrile to provide 18 mg of a solid. The two solids were combined, rechromatographed and then recystallised from ethanol. The resultant prisms were concentrated from methanol to provide 40 mg of 2-methyl-1-{4-[(1-methylethyl)sulfonyl]butyl}-6,7,8,9-tetrahydro-1H-imidazo[4,5-c]quinolin-4-amine as a white powder, m.p. 177–178° C.

Analysis: Calculated for $C_{18}H_{28}N_4O_2S$: % C, 59.31; % H, 7.74; % N, 15.37; Found: % C, 59.27; % H, 7.82; % N, 15.19. $^1$H NMR (300 MHz, DMSO-$d_6$): δ 5.64 (s, 2H); 4.21 (m, 2H); 3.21 (septet, 1H, J=6.9 Hz); 3.14 (m, 2H); 2.94 (m, 2H); 2.65 (m, 2H); 2.47 (s, 3H); 1.76 (br m, 8H); 1.23 (d, 6H, J=6.6 Hz). EIMS (m/z): 365 (M+1).

EXAMPLE 77

2-methyl-1-{4-[(4-fluorophenyl)sulfonyl]butyl}-6,7,8,9-tetrahydro-1H-imidazo[4,5-c]quinolin-4-amine

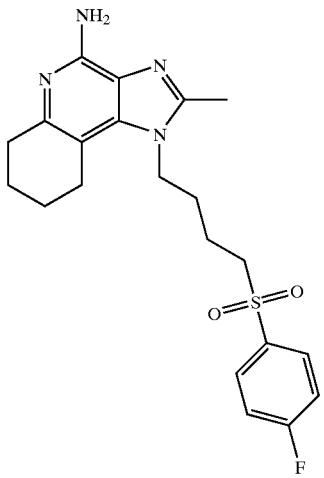

Part A

Using the general method of Example 76 Part G, 1-(4-chlorobutyl)-2-methyl-4-phenoxy-6,7,8,9-tetrahydro-1H-imidazo[4,5-c]quinoline (740 mg, 2.00 mmol, 1.0 eq) was reacted with 4-fluorobenzenethiol (260 FL, 1.2 eq) to provide 0.91 g of 1-{[4-(4-fluorophenyl)1thio]butyl}-2-methyl-4-phenoxy-6,7,8,9-tetrahydro-1H-imidazo[4,5-c]quinoline as a light yellow solid.

Part B

Using the general method of Example 76 Part H, the material from Part A was oxidized to provide 1.02 g of 1-{[4-(4-fluorophenyl)sulfonyl]butyl}-2-methyl-4-phenoxy-6,7,8,9-tetrahydro-1H-imidazo[4,5-c]quinoline as a white foam.

Part C

Using the general method of Example 76 Part I, the material from Part B was aminated to provide 148 mg of 2-methyl-1-{4-[(4-fluorophenyl)sulfonyl]butyl}-6,7,8,9-tetrahydro-1H-imidazo[4,5-c]quinolin-4-amine as a white solid, m.p. softened at 137–144° C. then melted at 159–162° C.

Analysis: Calculated for $C_{21}H_{25}FN_4O_2S \cdot H_2O$: % C, 58.05; % H, 6.26; % N, 12.98; Found: % C, 57.78; % H, 5.93; % N, 12.72. $^1$H NMR (300 MHz, DMSO-$d_6$): δ 7.93 (m, 2H); 7.50 (m, 2H); 5.67 (s, 2H); 4.15 (m, 2H); 3.41 (m, 2H), 2.87 (br m, 2H); 2.64 (br m, 2H); 2.41 (s, 3H); 1.74 (br m, 8H). EIMS (m/z): 417 (M+1).

EXAMPLE 78

2-methyl-1-{4-[(1,1-dimethylethyl)sulfonyl]butyl}-6,7,8,9-tetrahydro-1H-imidazo[4,5-c]quinolin-4-amine

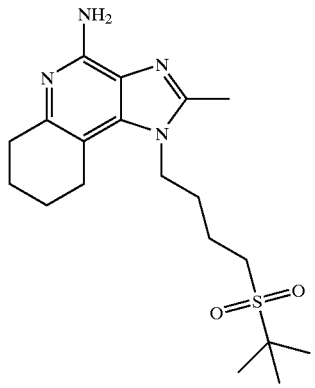

Part A

Using the general method of Example 76 Part G, 1-(4-chlorobutyl)-2-methyl-4-phenoxy-6,7,8,9-tetrahydro-1H-imidazo[4,5-c]quinoline (750 mg, 2.03 mmol, 1.0 eq) was reacted with 1,1-dimethylethylthiol (275 µL, 1.2 eq) to provide 0.91 g of 1-{[4-(1,1-dimethylethyl)1thio]butyl}-2-methyl-4-phenoxy-6,7,8,9-tetrahydro-1H-imidazo[4,5-c]quinoline as an oil which crystallized on standing.

Part B

Using the general method of Example 76 Part H, the material from Part A was oxidized to provide 1.0 g of 1-{[4-(1,1-dimethylethyl)sulfonyl]butyl}-2-methyl-4-phenoxy-6,7,8,9-tetrahydro-1H-imidazo[4,5-c]quinoline as a light yellow foam.

Part C

Using the general method of Example 76 Part I, the material from Part B was aminated to provide 460 mg of 2-methyl-1-{4-[(1,1-dimethylethyl)sulfonyl]butyl}-6,7,8,9-tetrahydro-1H-imidazo[4,5-c]quinolin-4-amine as a white solid, m.p. 208–210° C.

Analysis: Calculated for $C_{19}H_{30}N_4O_2S$: % C, 60.29; % H, 7.99; % N, 14.80; Found: % C, 60.26; % H, 7.88; % N, 14.89. $^1$H NMR (300 MHz, DMSO-$d_6$): δ 5.65 (s, 2H); 4.23 (m, 2H); 3.13 (m, 2H); 2.95 (br m, 2H); 2.65 (br m, 2H); 2.47 (s, 3H); 1.75 (br m, 8H). EIMS (m/z): 379 (M+1).

EXAMPLE 79

2-ethoxymethyl-1-(4-methanesulfonyl-butyl)-6,7,8,9-tetrahydro-1H-imidazo[4,5-c]quinolin-4-amine

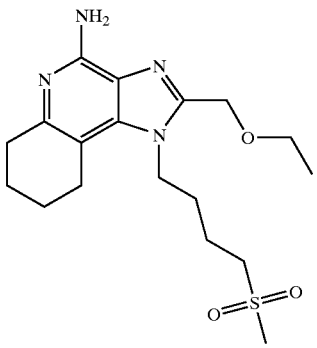

Part A

Sodium thiomethoxide (205 mg, 1.1 eq.) was added to a solution of 1-(4-chlorobutyl)-2-methyl-4-phenoxy-6,7,8,9- tetrahydro-1H-imidazo[4,5-c]quinoline (1.00 g, 2.66 mmol, 1.0 eq.) in DMF (13 mL). The reaction was stirred for 1 hour, then concentrated under reduced pressure. The residue was dissolved in methylene chloride (110 mL), washed with water (1×30 mL), dried over magnesium sulfate and concentrated under reduced pressure to provide 0.97 g of (4-methylsulfanyl-butyl)-(3-nitro-2-phenoxy-5,6,7,8-tetrahydro-quinolin-4-yl)-amine as a yellow solid.

Part B

Using the general method of Example 76 Part E, the material from Part A was reduced to provide 0.89 g of $N^4$-(4-methylsulfanyl-butyl)-2-phenoxy-5,6,7,8-tetrahydroquinoline-3,4-diamine as a clear colorless oil.

Part C

Ethoxyacetyl chloride was added to a solution of the material from Part B in pyridine (10 mL). After stirring at ambient temperature for 1 hour, the reaction was heated at 95° C. for 1 hour, then 105° C. for 4 hours. The reaction mixture was cooled to ambient temperature and concentrated under reduced pressure. The residue was dissolved in methylene chloride (100 mL), washed with saturated aqueous sodium bicarbonate (1×25 mL), dried over magnesium sulfate and concentrated under reduced pressure to provide 0.89 g of 2-ethoxymethyl-1-(4-methylsulfanyl-butyl)-4-phenoxy-6,7,8,9-tetrahydro-1H-imidazo[4,5-c]quinoline as a light yellow oil.

Part D

Using the general method of Example 76 Part H, the material from Part C was oxidized to provide 0.60 g of 2-ethoxymethyl-1-(4-methanesulfonyl-butyl)-4-phenoxy-6,7,8,9-tetrahydro-1H-imidazo[4,5-c]quinoline as a light brown foam.

Part E

Using the general method of Example 76 Part I, the material from Part D was aminated to provide 355 mg of 2-ethoxymethyl-1-(4-methanesulfonyl-butyl)-6,7,8,9-tetrahydro-1H-imidazo[4,5-c]quinolin-4-amine as an off white solid, m.p. 170–171° C.

Analysis: Calculated for $C_{24}H_{31}N_3O_4S$: % C, 56.82; % H, 7.42; % N, 14.72; Found: % C, 56.64; % H, 7.32; % N, 14.47. $^1$H NMR (300 MHz, DMSO-$d_6$): δ 5.89 (br s, 2H); 4.64 (s, 2H); 4.29 (m, 2H); 3.51 (q, 2H, J=7.0 Hz); 3.17 (m, 2H); 2.96 (br s, 5H); 2.67 (m, 2H); 1.80 (m, 8H); 1.15 (t, 3H) J=7.0 Hz). EIMS (m/z): 381 (M+1).

Additional compounds that could be prepared using the methods described above include:

2-butyl-1-[4-(phenylthio)butyl]-1H-imidazo[4,5-c]quinolin-4-amine;
2-butyl-1-[2-(phenylthio)ethyl]-1H-imidazo[4,5-c]quinolin-4-amine;
2-butyl-1-[4-(phenylsulfonyl)butyl]-1H-imidazo[4,5-c]quinolin-4-amine;
2-butyl-1-[4-(methylthio)butyl]-1H-imidazo[4,5-c]quinolin-4-amine;
2-butyl-1-[4-(methylsulfonyl)butyl]-1H-imidazo[4,5-c]quinolin-4-amine;
1-[4-(phenylthio)butyl]-1H-imidazo[4,5-c]quinolin-4-amine;
1-[2-(phenylthio)ethyl]-1H-imidazo[4,5-c]quinolin-4-amine;
1-[4-(phenylsulfonyl)butyl]-1H-imidazo[4,5-c]quinolin-4-amine;
1-[4-(methylsulfonyl)butyl]-1H-imidazo[4,5-c]quinolin-4-amine;
1-[4-(methylthio)butyl]-1H-imidazo[4,5-c]quinolin-4-amine;
2-butyl-1-[5-(methylsulfonyl)pentyl]-1H-imidazo[4,5-c]quinolin-4-amine;
1-[5-(methylsulfonyl)pentyl]-1H-imidazo[4,5-c]quinolin-4-amine;
2-ethyl-1-[5-(methylsulfonyl)pentyl]-1H-imidazo[4,5-c]quinolin-4-amine;
2-methyl-1-[5-(methylsulfonyl)pentyl]-1H-imidazo[4,5-c]quinolin-4-amine;
2-hexyl-1-[5-(methylsulfonyl)pentyl]-1H-imidazo[4,5-c]quinolin-4-amine;
2-methoxyethyl-1-[5-(methylsulfonyl)pentyl]-1H-imidazo[4,5-c]quinolin-4-amine;
2-butyl-1-[5-(methylthio)pentyl]-1H-imidazo[4,5-c]quinolin-4-amine;
2-butyl-1-[5-(methylsulfinyl)pentyl]-1H-imidazo[4,5-c]quinolin-4-amine;
2-butyl-1-[3-(methylsulfonyl)propyl]-1H-imidazo[4,5-c]quinolin-4-amine;
2-butyl-1-[3-(phenylsulfonyl)propyl]-1H-imidazo[4,5-c]quinolin-4-amine;
2-propyl-1-[4-(methylsulfonyl)butyl]-1H-imidazo[4,5-c]quinolin-4-amine;
2-butyl-1-[5-(methylsulfonyl)pentyl]-1H-imidazo[4,5-c]quinolin-4-amine;
2-butyl-1-[3-(methylsulfonyl)propyl]-1H-imidazo[4,5-c]quinolin-4-amine;
2-methyl-1-[4-(methylsulfonyl)butyl]-1H-imidazo[4,5-c]quinolin-4-amine;
2-ethyl-1-[4-(methylsulfonyl)butyl]-1H-imidazo[4,5-c]quinolin-4-amine;
1-[5-(phenylsulfonyl)pentyl]-1H-imidazo[4,5-c]quinoline-4-amine;
2-methyl-1-[5-(phenylsulfonyl)pentyl]-1H-imidazo[4,5-c]quinoline-4-amine;
2-ethyl-1-[5-(phenylsulfonyl)pentyl]-1H-imidazo[4,5-c]quinoline-4-amine;
2-propyl-1-[5-(phenylsulfonyl)pentyl]-1H-imidazo[4,5-c]quinoline-4-amine;
2-butyl-1-[5-(phenylsulfonyl)pentyl]-1H-imidazo[4,5-c]quinoline-4-amine;
2-(2-cyclopropylethyl)-1-[5-(phenylsulfonyl)pentyl]-1H-imidazo[4,5-c]quinoline-4-amine;
2-(2-cyclopropylethyl)-1-[5-(methylsulfonyl)pentyl]-1H-imidazo[4,5-c]quinoline-4-amine;
2-cyclopropylmethyl-1-[5-(phenylsulfonyl)pentyl]-1H-imidazo[4,5-c]quinoline-4-amine;
2-cyclopropylmethyl-1-[5-(methylsulfonyl)pentyl]-1H-imidazo[4,5-c]quinoline-4-amine;
2-methoxyethyl-1-[5-(methylsulfonyl)pentyl]-1H-imidazo[4,5-c]quinoline-4-amine;
2-methoxyethyl-1-[5-(phenylsulfonyl)pentyl]-1H-imidazo[4,5-c]quinoline-4-amine;
2-ethoxymethyl-1-[5-(methylsulfonyl)pentyl]-1H-imidazo[4,5-c]quinoline-4-amine;
2-propyl-1-[5-(methylsulfonyl)pentyl]-1H-imidazo[4,5-c]quinoline-4-amine;
2-methyl-1-[3-(methylthio)propyl]-1H-imidazo[4,5-c]quinoline-4-amine;
2-methyl-1-[3-(methylsulfonyl)propyl]-1H-imidazo[4,5-c]quinoline-4-amine;
2-ethyl-1-[3-(methylthio)propyl]-1H-imidazo[4,5-c]quinoline-4-amine;
2-methyl-1-[4-(methylthio)butyl]-1H-imidazo[4,5-c]quinolin-4-amine;
2-methyl-1-[4-(methylsulfinyl)butyl]-1H-imidazo[4,5-c]quinolin-4-amine;
2-ethyl-1-[4-(methylthio)butyl]-1H-imidazo[4,5-c]quinolin-4-amine;
2-propyl-1-[4-(methylthio)butyl]-1H-imidazo[4,5-c]quinolin-4-amine;

2-butyl-1-[4-(methylsulfinyl)butyl]-1H-imidazo[4,5-c]quinolin-4-amine;
2-methyl-1-[(2-methylthio)ethyl]-1H-imidazo[4,5-c]quinoline-4-amine;
2-ethyl-1-[(2-methylthio)ethyl]-1H-imidazo[4,5-c]quinoline-4-amine;
2-propyl-1-[(2-methysulfonyl)ethyl]-1H-imidazo[4,5-c]quinoline-4-amine;
2-butyl-1-{4-[(2,4-difluorophenyl)thio]butyl}-1H-imidazo[4,5-c]quinolin-4-amine;
2-butyl-1-{4-[(2,4-difluorophenyl)sulfonyl]butyl}-1H-imidazo[4,5-c]quinolin-4-amine;
2-butyl-1-[4-(ethylsulfonyl)butyl]-1H-imidazo[4,5-c]quinoline-4-amine;
2-butyl-1-[4-(tert-butylsulfonyl)butyl]-1H-imidazo[4,5-c]quinoline-4-amine;
2-butyl-1-{4-[(4-fluorophenyl)thio]butyl}-1H-imidazo[4,5-c]quinolin-4-amine;
2-butyl-1-{4-[(4-fluorophenyl)sulfonyl]butyl}-1H-imidazo[4,5-c]quinolin-4-amine;
4-amino-2-methyl-1-[4-(methylthio)butyl]-1H-imidazo[4,5-c]quinolin-8-ol;
2-ethyl-1-{4-[(1-methylethyl)thio]butyl}1H-imidazo[4,5-c]quinoline-4-amine;
2-ethyl-1-{4-[(3,5-dichlorophenyl)thio]butyl}1H-imidazo[4,5-c]quinoline-4-amine;
2-ethyl-1-[4-(cyclopentylsulfonyl)butyl]1H-imidazo[4,5-c]quinoline-4-amine;
2-ethyl-1-{4-[(3,5-dichlorophenyl)sulfonyl]butyl}1H-imidazo[4,5-c]quinoline-4-amine;
2-ethyl-1-[4-(propylthio)butyl]1H-imidazo[4,5-c]quinoline-4-amine;
2-ethyl-1-{4-[(4-chlorophenyl)thio]butyl}1H-imidazo[4,5-c]quinoline-4-amine;
2-ethyl-1-[4-(butylthio)butyl]1H-imidazo[4,5-c]quinoline-4-amine;
2-ethyl-1-{4-[(4-fluorophenyl)thio]butyl}1H-imidazo[4,5-c]quinoline-4-amine;
2-ethyl-1-{4-[(4-chlorophenyl)sulfonyl]butyl}1H-imidazo[4,5-c]quinoline-4-amine;
2-ethyl-1-[4-(ethylthio)butyl]1H-imidazo[4,5-c]quinoline-4-amine;
2-ethyl-1-[4-(ethylsulfonyl)butyl]1H-imidazo[4,5-c]quinoline-4-amine;
2-ethyl-1-[4-(cyclohexylsulfonyl)butyl]1H-imidazo[4,5-c]quinoline-4-amine;
2-butyl-1-{2-[(1-methylethyl)sulfonyl]ethyl}1H-imidazo[4,5-c]quinoline-4-amine;
2-butyl-1-{2-[(4-fluorophenyl)sulfonyl]ethyl}1H-imidazo[4,5-c]quinoline-4-amine;
2-butyl-1-{2-[(1,1-dimethylethyl)sulfonyl]ethyl}1H-imidazo[4,5-c]quinoline-4-amine;
2-butyl-1-{2-[(1,1-dimethylethyl)thio]ethyl}1H-imidazo[4,5-c]quinoline-4-amine;
2-butyl-1-[2-(propylthio)ethyl]1H-imidazo[4,5-c]quinoline-4-amine;
2-butyl-1-{2-[(2-methylpropyl)sulfonyl]ethyl}1H-imidazo[4,5-c]quinoline-4-amine;
2-butyl-1-[2-(ethylsulfonyl)ethyl]1H-imidazo[4,5-c]quinoline-4-amine;
2-butyl-1-[2-(ethylthio)ethyl]1H-imidazo[4,5-c]quinoline-4-amine;
2-butyl-1-[2-(methylsulfonyl)ethyl]1H-imidazo[4,5-c]quinoline-4-amine;
2-methyl-1-[6-(methylsulfonyl)hexyl]1H-imidazo[4,5-c]quinoline-4-amine;
1-[5-(phenylsulfonyl)pentyl]1H-imidazo[4,5-c]quinoline-4-amine;
2-trifluoromethyl-1-[5-(methylsulfonyl)pentyl]1H-imidazo[4,5-c]quinoline-4-amine;
2-methoxyethyl-1-[5-(phenylsulfonyl)pentyl]1H-imidazo[4,5-c]quinoline-4-amine;
2-ethyl-1-[4-(pyrimidin-2-ylthio)butyl]-1H-imidazo[4,5-c]quinolin-4-amine;
2-ethyl-1-[4-(pyrimidin-2-ylsulfonyl)butyl]-1H-imidazo[4,5-c]quinolin-4-amine;
2-methyl-1-[4-(methylsulfonyl)butyl]-6,7,8,9-tetrahydro-1H-imidazo[4,5-c]quinolin-4-amine;
2-methyl-1-[5-(methylsulfonyl)pentyl]-6,7,8,9-tetrahydro-1H-imidazo[4,5-c]quinolin-4-amine;
2-methyl-1-{5-[(1-methylethyl)sulfonyl]pentyl}-6,7,8,9-tetrahydro-1H-imidazo[4,5-c]quinolin-4-amine;
2-methyl-1-{4-[(4-fluorophenyl)sulfonyl]butyl}-6,7,8,9-tetrahydro-1H-imidazo[4,5-c]quinolin-4-amine;
2-methyl-1-{4-[(1,1-dimethylethyl)sulfonyl]butyl}-6,7,8,9-tetrahydro-1H-imidazo[4,5-c]quinolin-4-amine;
2-ethoxymethyl-1-[4-(pyrimidin-2-ylsulfonyl)butyl]-1H-imidazo[4,5-c]quinolin-4-amine;
2-propyl-1-[4-(pyrimidin-2-ylsulfonyl)butyl]-1H-imidazo[4,5-c]quinolin-4-amine;
2-propyl-1-[3-(pyrimidin-2-ylsulfonyl)propyl]-1H-imidazo[4,5-c]quinolin-4-amine;
2-propyl-1-[5-(pyrimidin-2-ylsulfonyl)pentyl]-1H-imidazo[4,5-c]quinolin-4-amine;
2-ethoxymethyl-1-[3-(pyrimidin-2-ylsulfonyl)propyl]-1H-imidazo[4,5-c]quinolin-4-amine; and
2-ethoxymethyl-1-[5-(pyrimidin-2-ylsulfonyl)pentyl]-1H-imidazo[4,5-c]quinolin-4-amine, and their pharmaceutically acceptable salts.

Cytokine Induction in Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque®-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30–0.014

μM). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by Origen® M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The table below lists the lowest concentration found to induce interferon and the lowest concentration found to induce tumor necrosis factor for each compound. A "*" indicates that no induction was seen at any of the tested concentrations.

Cytokine Induction in Human Cells

| Example Number | Lowest Effective Concentration (μM) | |
|---|---|---|
| | Interferon | Tumor Necrosis Factor |
| 1 | 0.12 | 0.12 |
| 2 | 0.12 | 0.37 |
| 3 | 0.04 | 0.12 |
| 4 | 0.01 | 0.01 |
| 5 | 0.01 | 0.04 |
| 6 | 3.33 | 10 |
| 7 | 3.33 | 10 |
| 8 | 10 | * |
| 9 | 3.33 | 3.33 |
| 10 | 1.11 | 1.11 |
| 11 | 0.01 | 0.12 |
| 12 | 0.12 | 10 |
| 13 | 0.12 | 3.33 |
| 14 | 3.33 | 10 |
| 15 | 0.04 | * |
| 16 | 0.01 | 0.04 |
| 17 | 0.01 | 0.04 |
| 18 | 0.01 | 0.12 |
| 19 | 0.04 | 0.37 |
| 20 | 0.04 | 0.37 |
| 21 | 0.12 | 0.37 |
| 22 | 0.37 | 1.11 |
| 23 | 3.33 | 10 |
| 24 | 0.12 | 0.37 |
| 25 | 0.37 | 3.33 |
| 26 | 0.04 | 0.37 |
| 27 | 3.33 | 10 |
| 28 | 0.01 | 0.37 |
| 29 | 0.12 | 3.33 |
| 30 | 0.37 | 3.33 |
| 31 | 0.04 | 0.12 |
| 32 | 0.12 | 0.12 |
| 33 | 3.33 | 10 |
| 34 | 0.37 | 3.33 |
| 35 | 1.11 | 3.33 |
| 36 | 1.11 | 1.11 |
| 37 | 0.37 | 1.11 |
| 38 | 0.37 | 1.11 |
| 39 | 0.04 | 0.04 |
| 40 | 0.01 | 0.01 |
| 41 | 0.37 | 0.37 |
| 42 | 0.12 | 0.12 |
| 43 | 0.014 | 0.37 |
| 44 | 1.11 | 10 |
| 45 | 0.37 | 1.11 |
| 46 | 0.12 | 0.37 |
| 47 | 0.37 | 3.33 |
| 48 | 0.014 | 0.12 |
| 49 | 0.37 | 1.11 |
| 50 | 0.37 | 1.11 |
| 51 | 0.12 | 1.11 |
| 52 | 0.37 | 1.11 |
| 53 | 0.04 | 0.37 |
| 54 | 0.37 | 1.11 |
| 55 | 0.12 | 1.11 |
| 56 | 0.37 | 0.37 |
| 57 | 1.11 | 1.11 |
| 58 | 1.11 | 1.11 |
| 59 | 0.01 | 0.04 |
| 60 | 0.37 | 0.37 |
| 61 | 0.04 | 0.12 |
| 62 | 0.12 | 0.37 |
| 63 | 0.04 | 0.04 |
| 64 | 0.12 | 0.12 |
| 65 | 0.01 | 0.04 |
| 66 | 0.12 | 0.12 |
| 67 | 0.01 | 0.04 |
| 68 | 0.014 | 0.12 |
| 69 | 1.11 | 1.11 |
| 70 | 0.01 | 0.01 |
| 71 | 30 | * |

What is claimed is:

1. A compound selected from the group consisting of 2-ethyl-1-[2-(methylsulfonyl)ethyl]-1H-imidazo[4,5-c]quinolin-4-amine;

2-butyl-1-[2-(propylsulfonyl)ethyl]-1H-imidazo[4,5-c]quinolin-4-amine;

2-butyl-1-[2-(ethylsulfonyl)ethyl]-1H-imidazo[4,5-c]quinolin-4-amine;

2-methyl-1-[5-(methylsulfonyl)pentyl]-6,7,8,9-tetrahydro-1H-imidazo[4,5-c]quinolin-4-amine;

or a pharmaceutically acceptable salt thereof.

* * * * *

UNITED STATES PATENT AND TRADEMARK OFFICE
CERTIFICATE OF CORRECTION

PATENT NO. : 6,949,649 B2  Page 1 of 4
APPLICATION NO. : 10/696477
DATED : September 27, 2005
INVENTOR(S) : Bonk et al.

It is certified that error appears in the above-identified patent and that said Letters Patent is hereby corrected as shown below:

<u>Title page, page 2,</u> Item (56), References Cited,
Other Publications, column 1, line 20, After "Chemistry," insert -- 11, --;

<u>Column 7-8,</u>

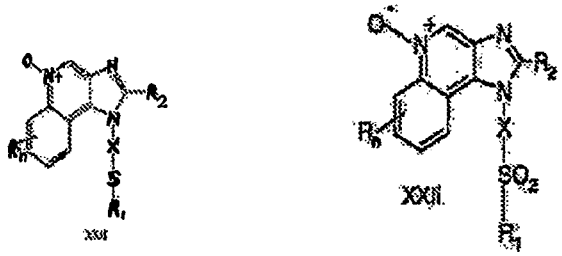

Structure XXII, Delete "            ", and insert --              -- therefore;

<u>Column 10,</u>
Line 6, Delete "XXVII" and insert -- XXVIII --, therefore;

<u>Column 21,</u>
Line 26, Delete "subsuituents" and insert -- substituents --, therefore;

<u>Column 28,</u>
Line 40, After "1.79 g" delete ";" and insert -- , --, therefore;

<u>Column 31,</u>
Line 61, After "butyl]" delete "-H-" and insert -- -1H- --, therefore;

<u>Column 40,</u>
Line 16, Delete "N" and insert --$N^4$--, therefore;

<u>Column 42,</u>
Line 28, Delete "N4" and insert -- $N^4$ --, therefore;
Line 44, After "10.37 mmol)" delete ";";
Line 59, After "Analysis" delete ":" and insert -- . --, therefore;

UNITED STATES PATENT AND TRADEMARK OFFICE
CERTIFICATE OF CORRECTION

PATENT NO. : 6,949,649 B2
APPLICATION NO. : 10/696477
DATED : September 27, 2005
INVENTOR(S) : Bonk et al.

It is certified that error appears in the above-identified patent and that said Letters Patent is hereby corrected as shown below:

Column 46,
Line 6, Delete "J6.8Hz," and insert -- J=6.8 Hz, --, therefore;
Line 33, Delete "N" and insert -- $N^4$ --, therefore;
Line 59, Delete "ClN$_4$" and insert --ClN$_4$ --, therefore;

Column 47,
Line 67, After "(m, 4H)," insert -- δ -- ;

Column 49,
Line 14, After "amine" insert -- ( --;

Column 54,
Line 67, After "J=7.5 Hz, 2H)" insert -- ; --;

Column 55,
Line 36, After "J=7.5 Hz, 2H)" insert -- ; --;

Column 56,
Line 28, After "J=7.2 Hz, 3H)" insert -- ; --;
Line 67, After "(t, J=7.2 Hz, 3H)" insert -- ; --;

Column 57,
Line 62, After "DMSO-" delete "d6)" and insert -- $d_6$) --, therefore;

Column 59,
Line 3, After "DMSO-" delete "d6)" and insert -- $d_6$) --, therefore;
Line 29, Delete "14:54 mmol" and insert -- 14.54 mmol --, therefore;

Column 62,
Line 60, After "16.52" insert -- ; -- ;

Column 64,
Line 5, After "[4,5-c]quinolin" insert -- -4-amine --;

Column 67-68,
Example 46, Line 4, After "N," delete "[]";

Column 71,
Example 53, Line 4, Delete "J. 7.2Hz," and insert -- J=7.2Hz, --, therefore;

UNITED STATES PATENT AND TRADEMARK OFFICE
CERTIFICATE OF CORRECTION

PATENT NO. : 6,949,649 B2
APPLICATION NO. : 10/696477
DATED : September 27, 2005
INVENTOR(S) : Bonk et al.

It is certified that error appears in the above-identified patent and that said Letters Patent is hereby corrected as shown below:

Column 73,
Example 61, Line 1, Delete "$C_{19}H_{26}N_{45}$" and insert -- $C_{19}H_{26}N_4S$ --, therefore;

Column 78,
Line 60, After "$C_{18}H_{24}N_4O_2S$" delete "." And insert -- • --, therefore;
Line 64, Delete "J7.2 Hz" and insert -- J=7.2 Hz, --, therefore;
Line 66, After "1.68 (m, 2 H)" insert - -, - -;

Column 79,
Line 64, After "(t, J=6.6 Hz, 1 H)" delete ";" and insert -- , --, therefore;

Column 80,
Line 41, Delete "Celite®D" and insert -- Celite® --, therefore;

Column 82,
Line 36, After "$C_{20}H_{22}N_6S$" delete "." and insert -- • --, therefore;

Column 83,
Line 9, After "$C_{20}H_{22}N_6O_2$" delete "." And insert -- • --, therefore;

Column 84,
Line 28, Delete "$C_{17}H_26N_4O_2S$" and insert -- $C_{17}H_{26}N_4O_2S$ --, therefore;

Column 87,
Line 41, Delete "260 FL" and insert -- 260 µL --, therefore;
Line 62, After "$C_{21}H_{25}FN_4O_2S$" delete "." and insert -- • --, therefore;

UNITED STATES PATENT AND TRADEMARK OFFICE
CERTIFICATE OF CORRECTION

PATENT NO.        : 6,949,649 B2
APPLICATION NO. : 10/696477
DATED             : September 27, 2005
INVENTOR(S)       : Bonk et al.

It is certified that error appears in the above-identified patent and that said Letters Patent is hereby corrected as shown below:

<u>Column 89,</u>
Line 41, After "(t, 3 H* delete ")" and insert -- , -- , therefore.

Signed and Sealed this

Twenty-first Day of November, 2006

JON W. DUDAS
*Director of the United States Patent and Trademark Office*